United States Patent
Annoura et al.

(10) Patent No.: US 6,998,401 B2
(45) Date of Patent: Feb. 14, 2006

(54) AMINOPHENOXYACETIC ACID DERIVATIVES AND PHARMACEUTICAL COMPOSITION CONTAINING THEREOF

(75) Inventors: Hirokazu Annoura, Kyoto (JP); Naohiro Takemoto, Osaka (JP); Hiroshi Uramoto, Osaka (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 10/394,221

(22) Filed: Mar. 24, 2003

(65) Prior Publication Data

US 2004/0063748 A1    Apr. 1, 2004

Related U.S. Application Data

(63) Continuation of application No. 09/581,756, filed as application No. PCT/JP99/05658 on Oct. 14, 1999, now Pat. No. 6,559,146.

(30) Foreign Application Priority Data

Oct. 16, 1998 (JP) ................... 10-294886

(51) Int. Cl.
*A61K 31/445* (2006.01)
*A61K 31/535* (2006.01)
*C07D 211/80* (2006.01)
*C07D 401/00* (2006.01)
*C07D 217/02* (2006.01)

(52) U.S. Cl. .................. 514/237.2; 514/307; 514/314; 514/318; 514/321; 514/323; 546/141; 546/144; 546/192; 546/193; 546/201

(58) Field of Classification Search ........... 546/193, 546/192, 201, 141, 144; 514/316, 323, 331, 514/307, 257.2, 314
See application file for complete search history.

(56) References Cited

U.S. PATENT DOCUMENTS 5,214,147 A    5/1993    Kazmierczak et al.

6,060,485 A    5/2000    Kaihoh et al.

FOREIGN PATENT DOCUMENTS

| EP | 0318029 | 5/1989 |
|---|---|---|
| EP | 0481299 | 4/1992 |
| EP | 0913393 | 5/1999 |
| WO | 93/25528 | 12/1993 |

OTHER PUBLICATIONS

E.M. Grasbon-Frodl et al, *Neuroscience*, 73(1):171-183 (1996).
F. Liu et al, *The Journal of Neuroscience*, 12(11):4281-4297 (1992).
M.P. Mattson et al, *Neuron*, 6(1):41-51 (1991).
J. Hugon et al, *Brain Res.*, 707(2):288-292 (1996).

*Primary Examiner*—Cecillia J. Tsang
*Assistant Examiner*—Raymond Covington
(74) *Attorney, Agent, or Firm*—Drinker, Biddle & Reath; Ronald L. Grudziecki

(57) ABSTRACT

There is provided an aminophenoxyacetic acid derivative of the following formula (I):

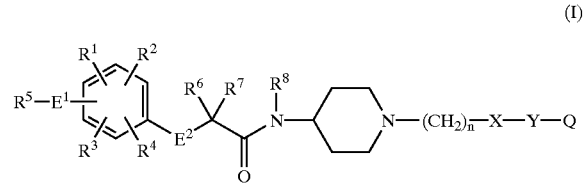

wherein, $R^1$, $R^2$, $R^3$ and $R^4$ are, independent from each other, alkoxy group, alkyl group or aryl group, etc.; $E^1$ and $E^2$ are oxygen atom, sulfur atom, etc.; n is 0 to 5; X and Y are alkylene group, cycloalkylen group, or alkenylen group; Q is pheny group which may be substituted or benzoyl group, etc,
or a pharmaceutically acceptable salt thereof.

These compounds have neuroprotective effects by inducing calbindin D28Kd, one of $Ca^{2+}$-binding proteins.

6 Claims, No Drawings

AMINOPHENOXYACETIC ACID DERIVATIVES AND PHARMACEUTICAL COMPOSITION CONTAINING THEREOF

This application is a continuation of U.S. application Ser. No. 09/581,756, filed on Nov. 1, 2000, now U.S. Pat. No. 6,559,146 which was a national stage filing under 35 U.S.C. § 371 of International Application No. PCT/JP99/05658 filed on Oct. 14, 1999.

TECHNICAL FIELD

The present invention relates to novel aminophenoxyacetic acid derivatives and pharmaceutically acceptable salt thereof, which have neuroprotective effects by inducing or increasing calbindin D28Kd, one of $Ca^{2+}$-binding proteins, and which are useful in ameliorating and treating functional and organic disorders in the brain. More specifically, the present invention relates to therapeutic and improving agents for the alleviation or treatment of symptoms due to various ischemic disorders in the brain such as sequelae of cerebral infarction, sequelae of intracerebral hemorrhage, sequelae of cerebral arteriosclerosis and so on, and symptoms of organic brain disorder such as senile dementia, sequelae of head trauma, sequelae of surgical brain operation, Alzheimer's disease, Parkinson's disease, amyotrophic lateral sclerosis and so on.

BACKGROUND ART

It is generally considered that the pathogenesis of progressive, delayed death of nerve cells, observed in cerebral injury and cerebrovascular disease such as intracerebral hemorrhage, transient ischemia attack, and cerebral infarction, is mainly caused by a rise in intracellular $Ca^{2+}$ concentration due to various factors related to signal transductions. Such factors related to signal transduction include, for example, abnormal activation of glutamate receptors due to excessive release glutamate, that is, an excitatory neurotransmitter, abnormal activation of ion channels, and excessive production of reactive oxygen species/free radicals. [F. B. Meyer, *Bras Res. Rev.*, 14, 227 (1989); E. Boddeke et al., *Trends Pharmacol. Sci.*, 10, 397 (1989); J. M. McCall et al., *Ann. Rep. Med. Chem.*, 27, 31 (1992)].

From these points of view, medicaments for preventing or suppressing the neuronal cell death, such as glutamate receptor antagonists, calcium channel blockers, antioxidants and so on have been developed. However, these clinically used medicaments suppress only a few pathways related to increase of the cellular $Ca^{2+}$ concentration, and are not sufficient for preventing or suppressing the neuronal cell death.

On the contrary, calbindin D28Kd, one of $Ca^{2+}$-binding proteins and mainly distributed in friable site of the brain against ischemic disease, is reported to possess buffering effects for a rise in cytotoxic intracellular $Ca^{2+}$ concentration. [A. M. Lacopino et al., *Neurodegeneration*, 3, 1 (1994); M. P. Mattson et al., *Neuron*, 6, 41 (1991)]

Accordingly, it is expected to achieve sufficient neuroprotective effects against the increase of intracellular $Ca^{2+}$ concentration caused by any kinds of pathways if calbindin D28Kd, one of the $Ca^{2+}$-binding proteins per se, can be supplied in a living body. That is, it is expected that medicaments containing calbindin D28Kd would be effective therapeutic and improving agents for the allevivation or treatment of symptoms due to various ischemic disorders in the brain such as sequelae of cerebral infarction, sequelae of intracerebral hemorrhage, sequelae of cerebral arteriosclerosis and so on, and symptoms of organic brain disorder such as senile dementia, sequelae of head trauma, sequelae of surgical brain operation, Alzheimer's disease, Parkinson's disease, amyotrophic lateral sclerosis and so on.

However, because calbindin D28Kd is unstable macromolecular protein having 28 Kd (kilo dalton) of molecular weight, it is difficult to be administered directly into a site in the central nervous system of a living body in view of pharmacological and pharmaceutical standpoints.

On the other hand, the lower molecular compounds having effect on induction of the calbindin D28Kd can be easily prepared into the various kinds of pharmaceutical compositions by the conventional techniques. Thus, these lower molecular compounds are expected to induce the calbindin D28Kd after administration in to a body, and to possess buffering action against the increase of the cellular $Ca^{2+}$ concentration. That is, these lower compounds can be effective compounds for improving and treating cerebral functional and organic disorders.

Under these circumstances, the objective of the present invention is to provide the lower molecular weight compounds having neuroprotective effect by inducing the calbindin D28Kd, one of $Ca^{2+}$-binding proteins, of low toxicity in suitable preparations of pharmaceutical compositions such as intravenous injectable solution.

The further purpose of the present invention is to provide the therapeutic and improving agents for the allevivation or treatment of symptoms due to various ischemic disorders in the brain such as sequelae of cerebral infarction, sequelae of intracerebral hemorrhage, sequelae of cerebral arteriosclerosis and so on, and symptoms of organic brain disorder such as senile dementia, sequelae of head trauma, sequelae of surgical brain operation, Alzheimer's disease, Parkinson's disease, amyotrophic lateral sclerosis and so on.

DISCLOSURE OF THE INVENTION

As one aspect of the present invention, it is provided aminophenoxyacetic acid derivatives represented by the following formula (I):

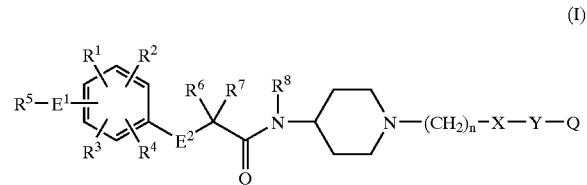

(I)

wherein:

$R_1$, $R_2$, $R_3$ and $R_4$ are, independent from each other, hydrogen atom; halogen atom; hydroxy group; alkoxy group which may be substituted; alkyl group which may be substituted; aryl group which may be substituted; or aralkyl group which may be substituted;

$R_5$, $R_6$, $R_7$ and $R_8$ are, independent from each other, hydrogen atom; alkyl group which may be substituted; aryl group which may be substituted; or aralkyl group which may be substituted;

$E_1$ is oxygen atom; sulfur atom; or group —$NR_9$— (in which, $R_9$ is hydrogen atom; alkyl group which may be substituted; aryl group which may be substituted; or aralkyl group which may be substituted);

$E_2$ is oxygen atom; sulfur atom; or group —$NR_{10}$— (in which, $R_{10}$ is hydrogen atom; alkyl group which may be substituted; aryl group which may be substituted; or aralkyl group which may be substituted);

n is 0 to 5;

X and Y are, independent from each other, connecting bond; alkylene group which may be substituted by hydroxyl group, carboxyl group, oxo group or morpholinyl group; cycloalkylene group; alkenylene group which may be substituted by lower alkyl group; —NHCO—; —CONH—; or —$SO_2$—; or —X—Y— represents —$CON(CH_3)$—;

Q is hydrogen atom; naphthyl group; phenyl group which may be substituted; phenoxy group which may be substituted; benzoyl group which may be substituted; pyridyl group which may be substituted; quinolyl group which may be substituted; isoquinolyl group which may be substituted; or benzimidazolyl group which may be substituted; (provided that one of $E_1$ and $E_2$ represent either oxygen atom or sulphur atom then the other one of $E_1$ and $E_2$ represent neither oxygen atom nor sulfur atom at the same time, and in the case of $E_1$ is nitrogen atom and $E_2$ is oxygen atom, or in the case of $E_1$ is oxygen atom and $E_2$ is nitrogen atom, all of the groups of $R_1$, $R_2$, $R_3$ and $R_4$ do not represent methyl group at the same time), or pharmaceutically acceptable salts thereof.

More specifically, the present invention provides the aminophenoxyacetic acid derivatives of the formula (I), in which;

1. $R^1$, $R^2$, $R^3$ and $R^4$ are, independent from each other, hydrogen atom; halogen atom; alkoxy group; or alkyl group which may be substituted; $R^5$ is hydrogen atom or alkyl group which may be substituted; $E^1$ is —NH—; and $E^2$ is oxygen atom,
2. $E^1$ is —NH—; $E^2$ is oxygen atom; either the case in which X is connecting bond and Y is group —CONH—, or the other in which X is the group —CONH— and Y is connecting bond; Q is phenyl group which may be substituted, and
3. $E^1$ and $E^2$ are —NH—; X and Y are connecting bond; Q is phenyl group which may be substituted, or pharmaceutically acceptable salts thereof.

According to the present inventor's investigations, it is confirmed that the aminophenoxyacetic acid in low concentration represented by the formula (I) effectively induced the calbindin D28Kd and possessed excellent neuroprotective effect accordingly. Further, these compounds are also confirmed to have high safety margin, and are suitable for preparation of various kinds of pharmaceutical compositions.

Therefore, the present invention provides the calbindin D28Kd, inducing agent containing aminophenoxyacetic acid derivatives represented by the formula (I) or pharmaceutically acceptable salts thereof as an active ingredient, as another embodiment.

As still a further embodiment, the present invention provides an improving and therapeutic agent for the cerebral functional and organic disorders containing aminophenoxyacetic acid derivatives represented by the formula (I) or pharmaceutically acceptable salt thereof, as an active ingredient.

Although lower molecular weight compounds, the aminophenoxyacetic acid derivatives of the formula (I) express the neuroprotective effect by inducing the calbindin D28Kd after administration into a living body.

Accordingly, as still another embodiment, the present invention provides a method for selecting a neuroprotective compound by measurement of inducing capability of calbindin D28Kd, which is $Ca^{2+}$-binding protein.

As still another embodiment, the present invention provides neuroprotective compounds to induce the calbindin D28Kd, one of $Ca^{2+}$-binding proteins.

As still a further embodiment, the present invention provides therapeutic and improving agents containing compounds having neuroprotective effect by inducing the calbindin D28Kd, against cerebral function disorders due to various ischemic disorders such as cerebral infarction, intracerebral hemorrhage and cerebral arteriosclerosis.

As still a further embodiment, the present invention provides therapeutic and improving agents containing compounds having neuroprotective effect by inducing calbindin D28Kd, for cerebral organic disorders such as senile dementia, cerebral injury, sequela of cerebral surgical operation, Alzheimer's disease, Parkinson's disease, and amyotrophic lateral sclerosis.

As a preferred embodiment, the present invention provides the aminophenoxyacetic acid derivatives represented by the formula (I) or pharmaceutically acceptable salt thereof is the pharmaceutical composition containing the compounds having neuroprotective effect by inducing the calbindin D28Kd.

BEST MODE FOR CARRYING OUT THE INVENTION

The aminophenoxyacetic acid derivatives of the present invention include aminophenoxyacetic acids, aminoanilinoacetic acids, aminothiophenoxyacetic acids, oxyanilinoacetic acids and thioanilinoacetic acids. Therefore, "aminophenoxyacetic acid derivatives" in this specification include all the derivatives stated above as long as not stated otherwise.

In the aminophenoxyacetic acid derivatives of the formula (I) provided by the present invention with reference to various substitution group of $R^1$ to $R^{10}$, "halogen atom" includes fluorine atom, chlorine atom and bromine atom.

The term "alkoxy group" stands for a straight-chained or branched-chained $C_1$–$C_5$ alkoxy group, and may include, for example, methoxy, ethoxy, n-propoxy, isopropoxy, n-butoxy, sec-butoxy, tert-butoxy and the like.

The term "alkyl group which may be substituted" stands for a straight-chained or branched-chained $C_1$–$C_5$ alkyl group which may be halogen-substituted, and may include, for example, methyl, ethyl, propyl, trifluoromethyl group, and the like.

The "aryl", a part of the term "aryl group which may be substituted", stands for $C_4$–$C_{14}$ aryl group or heteroaryl group which may contain one or more of hetero ring atom(s) such as nitrogen and oxygen atom(s). Examples of the preferred "aryl" include phenyl, pyridyl and naphthyl. The suitable substituents of said aryl group include halogen atom such as fluorine atom, chlorine atom and bromine atom; hydroxy group; a straight-chained or branched-chained $C_1$–$C_5$ alkoxy group such as methoxy and ethoxy group; and a straight-chained or branched-chained $C_1$–$C_5$ alkyl group which can be substituted by halogen atom such as methyl, ethyl, propyl and trifluoromethyl.

The "aralkyl", a part of the term "aralkyl group which may be substituted", stands for $C_5$–$C_{12}$ aralkyl group or heteroarylalkyl group, which may contain one or more of hetero ring atom such as nitrogen and oxygen atom(s). The examples include benzyl, phenethyl, pyridylmethyl, and pyridylethyl. The suitable substituents of said aralkyl group include halogen atoms such as fluorine atom, chlorine atom and bromine atom; hydroxy group; a straight-chained or branched-chained $C_1$–$C_5$ alkoxy group such as ethoxy group; and a straight-chained or branched-chained $C_1$–$C_5$ alkyl group which may be substituted by halogen atom such as methyl, ethyl, propyl and trifluoromethyl.

The "alkylene", a part of the term "alkylene group which may be substituted by hydroxyl group", refers to the substituents X and Y, and preferably represents a straight-chained or branched-chained $C_1$–$C_6$ alkylene group such as methylene, methylmethylene, ethylene, trimethylene, tetramethylene, cyclopropylmethylene and the like.

The term "cycloalkylene" preferably stands for $C_3$–$C_6$ cycloalkylene and may include 1,1-cyclopropylene, 1,2-cyclopropylene, 1,1-cyclobutylene, 1,1-cyclopentylene, 1,1-cyclo-hexylene and the like. Among them, 1,1-cyclopropylene and 1,2-cyclopropylene are more preferable.

The "alkenylene", a part of the term "alkenylene group which may be substituted by lower alkyl group", may include $C_2$–$C_4$ alkenylene such as vinylene, and butadiene and vinylene is preferably used. The lower alkyl group, which is substituent of alkylene group, may be methyl, ethyl, propyl, isopropyl and the like.

The suitable substituents represented as "Q" for "phenyl group which may be substituted", "phenoxy group which may be substituted", "benzoyl group which may be substituted", "pyridyl group which may be substituted", "quinolyl group which may be substituted", "isoquinolyl group which may be substituted" and "benzimidazolyl group which may be substituted", may include halogen atom such as fluorine atom, a chlorine atom and a bromine atom; a hydroxy group; a straight-chained or branched-chained $C_1$–$C_5$ alkoxy group such as methoxy, ethoxy group and so on. Furthermore, these substituents may also include a straight-chained or branched-chained $C_1$–$C_5$ alkyl group which may be substituted by halogen atom such as fluorine atom, chlorine atom and bromine atom. The examples include methyl, ethyl, propyl, trifluoromethyl and the like. Still further, these substituents include a carboxyl group, a carbamoyl group and an amino group.

The term "connecting bond" with reference to "X" and "Y" means direct bond. Therefore, if "X" and/or "Y" are connecting bond, two adjacent substituents of "X" and/or "Y" are connected directly, and these substituents do not exist as "X" and/or "Y".

It is understood that when the aminophenoxyacetic acid derivatives of the formula (I) of the present invention exist in the isomer forms, each isomers per se, as well as the isomeric mixture, shall be included in the compounds of the present invention. Namely, the structural isomers may exist due to the substituents on the benzene ring. Furthermore, optical isomers may exist due to the asymmetric carbon atom of the hydroxy substituted "X" or "Y" of alkylene group. These isomers shall be included within the scope of the compounds of the present invention.

The aminophenoxyacetic acid derivatives of the formula (I) include the compounds (Ia), (Ib) and (Ic) obtained by the synthetic process mentioned latter. For example, these compounds may be prepared by the following.

The compound (IV), obtained by the reaction of the compound (II) with the ester compound (III), is hydrolyzed to convert into carboxylic acid derivative (V). The obtained compound (V) is then converted into amide compound (VII) by the condensation reaction with the compound (VI). Further, the protecting group in the compound (VII) thus obtained is removed to obtain compound (Ia), the compound of formula (I) of the present invention, in which n is 0, X and Y are each a connecting bond and Q is a hydrogen atom (Process 1).

The compound (Ib) can be obtained by reacting the compound (Ia) with the compound (VIII) (Process 2).

Furthermore, the compound (Ic) can be obtained by reacting the compound (Ia) with the compound (IX) (Process 3).

Each process will be further illustrated by the following reaction scheme.

Process 1:

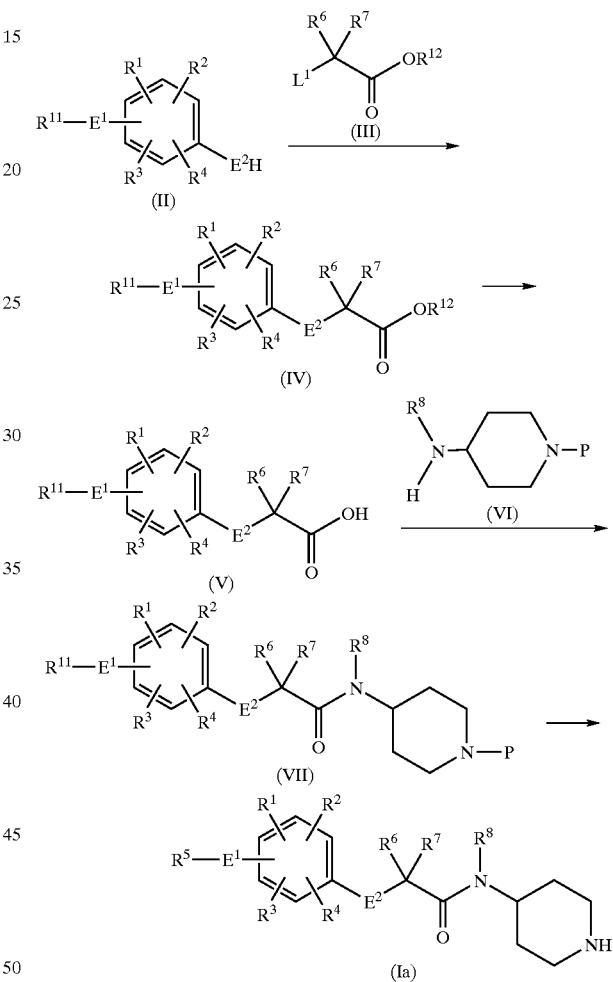

wherein $R^1$ to $R^8$, $E^1$ and $E^2$ have the same definitions as above, and $R^{11}$ is alkyl group which may be substituted, aryl group which may be substituted; aralkyl group which may be substituted; tert-butoxycarbonyl group; ethoxycarbonyl group; acetyl group; benzyloxycarbonyl group; p-methoxybenzyloxycarbonyl group; $R^{12}$ is a straight-chained or branched-chained $C_1$–$C_5$ alkyl group; $L^1$ is leaving group which can easily be replaced with amino, hydroxy and mercapto group; P is benzyl group, tert-butoxycarbonyl group, ethoxycarbonyl group; acetyl group; benzyloxycarbonyl group; p-methoxybenzyloxycarbonyl group.

According to this process-1, the compound (Ia) can be obtained from the known starting compound (II).

Namely, for the first step, the compound (II) is reacted with 1.0 to 1.5 mole equivalent of ester compound (III) in the inert solvent, and if necessary in the presence of the base, under stirring at −20° C. to 150° C., preferably at 0° C. to 100° C.

The inert solvent to be used in the reaction may be benzene, toluene, tetrahydrofuran, dioxane, dimethyformamide, dimethyl sulfoxide, acetonitrile, acetone, methanol, ethanol, isopropyl alcohol, tert-butyl alcohol, ethylene glycol and the like.

The base to be used in the above reaction may be an organic base such as triethylamine, diisopropylethylamine, pyridine and the like, or an inorganic base such as sodium, sodium hydride, potassium, potassium hydride, sodium ethoxide, potassium tert-butoxide, sodium carbonate, potassium carbonate, cesium carbonate, cesium fluoride, sodium bicarbonate, potassium bicarbonate and the like. These organic base and inorganic base may be used in combination, and sodium iodide or tetrabutylammonium iodide can be added in the reaction mixture.

The substituent "$L^1$" in the ester compound (III) may be the leaving group which can easily be replaced with amino, hydroxy and mercapto group, and examples include halogen atom such as chlorine atom, bromine atom, iodide atom; alkylsulfonyloxy group such as methanesulfonyloxy group; arylsulfonyloxy group such as p-toluenesulfonyloxy group, 3-nitrobenzenesulfonyloxy group and the like.

The compounds (II) and (III) to be used in this reaction are commercial available ones, or can easily prepared by the known methods.

The compound (II) and compound (III) to be used in this reaction can be commercially available and known compounds, or can be easily prepared from known compounds by using common methods.

Examples of the compound (II) include 4-(tert-butoxycarbonylamino)phenol, 4-(tert-butoxycarbonylamino)-2,3,5-trimethylphenol, 4-(tert-butoxycarbonylamino)-2-chloro-3,5,6-trimethylphenol, 4-(tert-butoxycarbonylamino)-2,3,6-trimethylphenol, 4-(tert-butoxycarbonylamino)-2,3-dimethylphenol, 4-(tert-butoxycarbonylamino)-2,5-dimethylphenol, 2-(tert-butoxycarbonylamino)-4,6-dimethylphenol, 5-(tert-butoxycarbonylamino)-2-methoxyphenol, 5-(tert-butoxycarbonylamino)-4-chloro-2-methoxyphenol, 4-(tert-butoxycarbonylamino)-2,6-dichlorophenol, 4-(tert-butoxycarbonylamino)-2,3,5,6-tetramethylaniline, 4-methoxy-2-methylaniline, 4-(tert-butoxycarbonylamino)-2,5-dimethylaniline, 2-(tert-butoxycarbonylamino)-4,5-dimethylaniline, 3-(tert-butoxycarbonylamino)-2,4,6-trimethylaniline, 4-(tert-butoxycarbonylamino)-2,5-dichloroaniline, 4-(tert-butoxycarbonylamino)-2,6-dichloroaniline, 2-(tert-butoxycarbonylamino)-3,4-dichloroaniline, 4-(tert-butoxycarbonylamino)-2-methoxy-5-methylaniline, 4-(tert-butoxycarbonylamino)-2,5-dimethoxyaniline, 4-(benzyloxycarbonylamino)phenol, 4-(benzyloxycarbonylamino)-2,3,5-trimethylphenol, 4-(benzyloxycarbonylamino)-2-chloro-3,5,6-trimethylphenol, 4-(benzyloxycarbonylamino)-2,3,6-trimethylphenol, 4-(benzyloxycarbonylamino)-2,3-dimethylphenol, 4-(benzyloxycarbonylamino)-2,5-dimethylphenol, 2-(benzyloxycarbonylamino)-4,6-dimethylphenol, 5-(benzyloxycarbonylamino)-2-methoxyphenol, 5-(benzyloxycarbonylamino)-4-chloro-2-methoxyphenol, 4-(benzyloxycarbonylamino)-2,6-dichlorophenol, 4-(benzyloxycarbonylamino)-2,3,4,6-tetramethylaniline, 4-(benzyloxycarbonylamino)-2,5-dimethylaniline, 2-(benzyloxycarbonylamino)-4,5-dimethylaniline, 3-(benzyloxycarbonylamino)-2,4,6-trimethylaniline, 4-(benzyloxycarbonylamino)-2,5-dichloroaniline, 4-(benzyloxycarbonylamino)-2,6-dichloroaniline, 2-(benzyloxycarbonylamino)-3,4-dichloroaniline, 4-(benzyloxycarbonylamino)-2-methoxy-5-methylaniline, 4-(benzyloxycarbonylamino)-2,5-dimethoxyaniline and so on.

The ester compound of the formula (III) includes, for example, ethyl bromoacetate, ethyl 2-bromopropionate, ethyl 2-bromo-2-methylpropionate, and so on.

Then, the obtained compound (IV) is hydrolyzed to convert into carboxylic acid derivative (V) by the common methods, and the resultant carboxylic acid derivative of the formula (V) is further converted into amide derivative (VII) by reaction with the compound (VI).

The compound (VI) to be used for the reaction with the compound (V) is known compound as described in *J. Med. Chem.*, 36, 3707 (1993) [R. H. Mach et al.], or can be easily prepared by the methods described in EP 0184257 A1 [R. A. Stokbroekx, et al.].

The reaction conditions of this amidation reaction may vary according to the methods described in "*Compendium for Organic Synthesis*" (wiley-Interscience: A Division of John Wiley & Sons Ltd.). For example, the compound (V) is treated optionally in the presence of an organic or an inorganic base with diethyl cyanophosphonate (DEPC), diphenylphosphoryl azide (DPPA), dicyclohexylcarbodiimide (DCC), 1-ethyl-3-(3-dimethylaminopropyl)carbodiimide hydrochloride, 2-iodo-1-methylpyridinium iodide or benzotriazol-1-yloxy-tris(dimethylamino)phosphonium hexafluorophosphate (BOP Reagent), and then reacted with compound (VI) to obtain the amide compound (VII). Furthermore, the compound (V) is converted into the activated ester compound such as acid halide, symmetric acid anhydride, or the mixture acid anhydride, then reacted with the compound (VI) to obtain the amide compound (VII).

The compound (VII) thus obtained is converted into the aminophenoxyacetic acid derivatives of the formula (Ia), the compound of the present invention, by the removal reaction of the protecting group on the nitrogen atom of the amide compound (VII).

This reaction may vary depend on the protecting group on the nitrogen atom of the compound (VII). For example, the compound (VII) is treated with acids such as trifluoroacetic acid, hydrogen chloride, hydrogen bromide, or sulfuric acid in an inert solvent such as benzene, toluene, acetonitrile, tetrahydrofuran, dioxane, chloroform, carbon tetrachloride, and the like. Furthermore, the removal of the protecting group may also be carried out by hydrogenolysis of the compound (VII) under 1 to 5 atm of hydrogen, in the presence of a catalyst such as palladium-carbon, palladium hydroxide, platinum, or platinum oxide, in an inert solvent such as methanol, ethanol, isopropyl alcohol, ethyl acetate or acetic acid.

Although each compounds obtained in the above process 1 may be used for the next reaction without further purification, it can also be used after further purification in conventional manner such as recrystallization or column chromatography and so on if necessary.

Process 2:

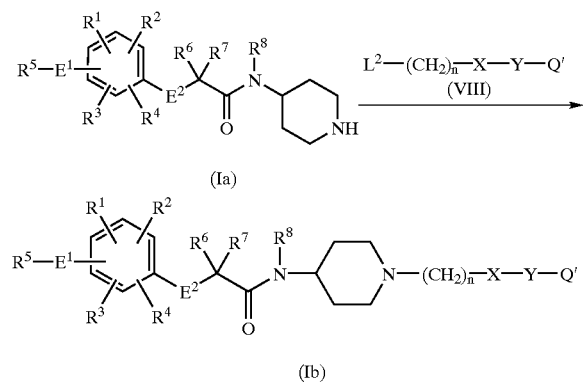

wherein $R^1$ to $R^8$, $E^1$, $E^2$, n, X and Y have the same definitions as above; and Q' is phenyl group which may be substituted, phenoxy group which may be substituted, benzoyl group which may be substituted, pyridyl group which may be substituted, quinolyl group which may be substituted, isoqunolyl group which may be substituted, or benzimidazolyl group which may be substituted; $L^2$ is leaving group which can be easily replaced with the amino group.

According to this process 2, the aminophenoxyacetic acid of the formula (Ib) of the present invention can be obtained by reacting the compound (Ia), obtained in the process 1 mentioned above, with the compound (VIII).

The compound (Ia) is reacted with 1.0 to 1.5 mole equivalent of the compound (VIII) in the inert solvent such as benzene, toluene, acetonitrile, ether, tetrahydrofuran, dioxan, methylene chloride, chloroform, carbon tetrachloride, dimethylformamide, and dimethyl sulfoxide in the presence of the base, at −50° C. to 120° C., preferably at −20° C. to 50° C.

The base to be used in the reaction may be an organic base such as triethylamine, pyridine, diisopropylethylamine and the like, or an inorganic base such as sodium carbonate, potassium carbonate, cesium carbonate, sodium bicarbonate, potassium bicarbonate, cesium fluoride, sodium hydride and the like. Sodium iodide or tetrabutylammonium iodide can be added in the reaction mixture.

The substituent "$L^2$" in the compound (VIII) is the leaving group, which can easily be replaced by amino group, and examples include halogen atom such as chlorine atom, bromine atom; alkylsulfonyloxy group such as methanesulfonyloxy group; arylsulfonyloxy group such as p-toluenesulfonyloxy group and the like.

In this process 2, the aminophenoxyacetic acid of the formula (Ib) can be produced as well.

Process 3:

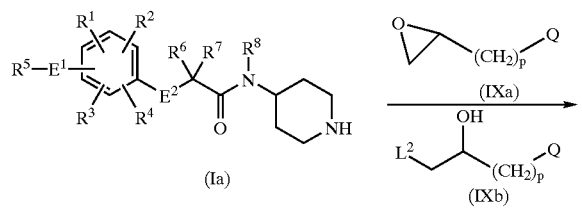

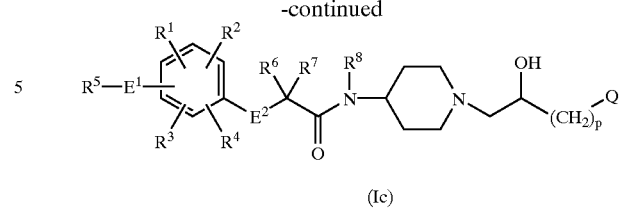

wherein $R^1$ to $R^8$, $E^1$, $E^2$, Q and L have the same definitions as previously mentioned, and p is 0 to 3.

According to this process 3, the aminophenoxyacetic acid of the formula (Ic) of the present invention can be obtained from the reaction of the compound (Ia), obtained in the process 1 mentioned above, with the compound (IXa) or the compound (IXb).

For example, the compound (Ia) is reacted with 0.9 to 1.5 mole equivalent of the compound (IXa) or (IXb) in an inert solvent at from room temperature to about 200° C., preferably at about 50° C. to about 150° C., to produce the aminophenoxyacetic acid of the formula (Ic).

The inert solvent to be used in the reaction may be benzene, toluene, tetrahydrofuran, diethyl ether, ethylene glycol dimethyl ether, dioxane, dimethyformamide, dimethyl sulfoxide, acetonitrile, methanol, ethanol, isopropyl alcohol, t-butyl alcohol, ethylene glycol and the like.

Examples of the compound (IXa) include epibromohydrin, epichlorohydrin, (R)-epichlorohydrin, (S)-epichlorohydrin and the like, and examples of the compound (IXb) include glycidyl tosylate, (R)-glycidyl tosylate, (S)-glycidyl tosylate, (R)-glycidyl 3-nitrobenzensulfonate, (S)-glycidyl 3-nitrobenzensulfonate, (R)-glycidyl 4-nitrobenzoate, (S)-glycidyl 4-nitrobenzoate, gylcidyltrimethylammonium chloride and the like.

In this process 3, the aminophenoxyacetic acid of the formula (Ic) can be produced as well.

The aminophenoxyacetic acid derivatives of the formula (I) thus obtained may be isolated and purified in conventional manner, such as recrystallization, column chromatography and the like.

Further, each isomers contained in the compounds of the formula (I) of the present invention can be obtained by resolution of the isomeric mixture of these compounds by the conventional methods, such as recrystallization, column chromatography, HPLC, and the like, or by using optically active reagents.

The compounds of the present invention represented by the formula (I) may be used in the form of free bases or suitable pharmaceutically acceptable acid addition salts thereof. The pharmaceutically acceptable salts can be obtained by treating the compound (I) with an inorganic acid or an organic acid in suitable solvent. Examples of the inorganic acid include hydrochloric acid, sulfuric acid, nitric acid, phosphoric acid, periodic acid and the like. Further, examples of the organic acid include formic acid, acetic acid, butyric acid, oxalic acid, malonic acid, propionic acid, valeric acid, succinic acid, fumaric acid, maleic acid, tartaric acid, citric acid, malic acid, benzoic acid, p-toluenesulfonic acid, methanesulfonic acid and the like.

The aminophenoxyacetic acid of the present invention represented by the formula (I) or pharmaceutically acceptable salts thereof shows low toxicity and may be administered per se. However, it may be converted in the form of pharmaceutically acceptable composition with the conventionally pharmaceutically acceptable carriers for improvement or treatment of ischemic diseases.

The dosage forms may include oral formulations such as capsules, tablets or parenteral formulations such as injection solution containing the compound of the formula (I) per se, or using the conventional excipients. For example, the capsules can be prepared by mixing the compound of the formula (I) in powder form with a suitable excipient such as lactose, starch or derivatives thereof or cellulose derivatives, and then filled in gelatin capsules.

Also, the tablets can be prepared by mixing the active ingredients with the above-mentioned excipients, binders such as sodium carboxymethylcellulose, alginic acid or gum arabic and water, then if necessary, making the resultant mixture into granules. Then, it may be further mixed with lubricant such as talc or stearic acid, and compressed into tablet by mean of common tableting machine.

Injectable formulations for parenteral route also can be prepared by dissolving the compound of the formula (I) or salts thereof in sterile distilled solution or sterile physiological saline solution with solution adjuvant, and filling it into ample. A stabilizer or buffer can be used in the injectable solution, and the injectable formulation may be administered intravenously or by dripping.

In administration of the compound of the formula (I) which possess neurocytic protecting effect based on induction of calbindin D28Kd, one of $Ca^{2+}$-bindind proteins, the therapeutically effective dosage for improving cerebral functional and organic disorders is not particularly limited and may vary depending on the various kinds of factors. These factors may be the patient's condition, the severity of the disease, age, existence of a complication, administration route, formulation, as well as number of times for administration.

A usual recommended daily dose for oral administration is within the range of 0.1–1,000 mg/day/person, preferably 1–500 mg/day/person, while a usual recommended daily dose for parenteral administration is within the range of 1/100 to 1/2 based on dose of the oral administration. These doses also may vary depending on age, as well as the patient's condition.

EXAMPLES

The present invention is illustrated in more detail by way of the following examples, but it is to be noted that the present invention is not limited by these Examples in any way.

The compound numbers in the following examples are identical to those in the Table mentioned later.

Example 1

2-(4-Amino-2,3,5-trimethylphenoxy)-N-methyl-N-(4-piperidinyl)acetamide (1)

A solution of 1.86 g of 2-[4-(tert-butoxycarbonylamino)-2,3,5-trimethylphenoxy]acetic acid, 1.43 g of 1-(tert-butoxycarbonyl)-4-methylaminopiperidine, 2.94 g of benzotriazol-1-yloxytris(dimethylamino)phosphonium hexafluorophosphate (BOP Reagent) and 1.26 ml of triethylamine in 30 ml of dimethylformamide was stirred over night at room temperature. Then, 15 ml of saturated sodium hydrogen carbonate solution was added to the reaction mixture and the mixture was extracted with ethyl acetate. The extract was washed with brine, dried and concentrated under reduced pressure to give a residue. The obtained residue was dissolved in 30 ml of methylene chloride, and to this solution was added 7.5 ml of trifluoroacetic acid at 0° C., then the mixture was stirred for 2 hours at room temperature. After removal of the solvent, the resultant residue was purified by silica gel column chromatography (methylene chloride:methanol=12:1) to give 1.52 g (81%) of the above-mentioned compound (1).

Example 2

2-(4-Amino-2,3,5-trimethylphenoxy)-N-methyl-N-(4-piperidinyl)propamide (2),

The title compound (2) was obtained from 2-[4-(tert-butoxycarbonylamino)-2,3,5-trimethylphenoxy]propionic acid and 1-(tert-butoxycarbonyl)-4-methylaminopiperidine by the same manner as the Example 1.

Example 3

2-(4-Amino-2,3,5-trimethylphenoxy)-2-methyl-N-methyl-N-(4-piperidinyl)propamide (3)

The title compound (3) was obtained from 2-[4-(tert-butoxycarbonylamino)-2,3,5-trimethylphenoxy]-2-methyl-propionic acid and 1-(tert-butoxycarbonyl)-4-methylaminopiperidine by the same manner as the Example 1.

Example 4

2-(2-Amino-4,6-dimethylphenoxy)-N-methyl-N-(4-piperidinyl)acetamide (4)

The title compound (4) was obtained from 2-[2-(tert-butoxycarbonylamino)-4,6-dimethylphenoxy]acetic acid and 1-(tert-butoxycarbonyl)-4-methylaminopiperidine by the same manner as the Example 1.

Example 5

2-(4-Amino-2,3,6-trimethylphenoxy)-N-methyl-N-(4-piperidinyl)acetamide (5)

The title compound (5) was obtained from 2-[4-(tert-butoxycarbonylamino)-2,3,6-trimethylphenoxy]acetic acid and 1-(tert-butoxycarbonyl)-4-methylaminopiperidine by the same manner as the Example 1.

Example 6

2-(5-Amino-2-methoxyphenoxy)-N-methyl-N-(4-piperidinyl)acetamide (6)

The title compound (6) was obtained from 2-[5-(tert-butoxycarbonylamino)-2-methoxyphenoxy]acetic acid and 1-(tert-butoxy-carbonyl)-4-methylaminopiperidine by the same manner as the Example 1.

Example 7

2-(5-Amino-2-methoxyphenoxy)-N-ethyl-N-(4-piperidinyl)acetamide (7)

The title compound (7) was obtained from 2-[5-(tert-butoxycarbonylamino)-2-methoxyphenoxy]acetic acid and 1-(tert-butoxycarbonyl)-4-ethylaminopiperidine by the same manner as the Example 1.

Example 8

2-(5-Amino-4-chloro-2-methoxyphenoxy)-N-ethyl-N-(4-piperidinyl)acetamide (8)

The title compound (8) was obtained from 2-[5-(tert-butoxycarbonylamino)-4-chloro-2-methoxyphenoxy]acetic acid and 1-(tert-butoxycarbonyl)-4-ethylaminopiperidine by the same manner as the Example 1.

Example 9

2-(4-Amino-2-chloro-3,5,6-trimethylphenoxy)-N-ethyl-N-(4-piperidinyl)acetamide (9)

The title compound (9) was obtained from 2-[4-(tert-butoxycarbonylamino)-2-chloro-3,5,6-trimethylphenoxy]acetic acid and 1-(tert-butoxycarbonyl)-4-ethylaminopiperidine by the same manner as the Example 1.

Example 10

2-(4-Amino-2,3,5,6-tetramethylanilino)-N-methyl-N-(4-piperidinyl)acetamide (10)

The title compound (10) was obtained from 2-[4-(tert-butoxycarbonylamino)-2,3,5,6-tetramethylanilino]acetic acid and 1-(tert-butoxycarbonyl)-4-methylaminopiperidine by the same manner as the Example 1.

Example 11

2-(4-Amino-2,3,5-trimethylphenoxy)-N-(4-piperidinyl)acetamide (11)

The title compound (11) was obtained from 2-[4-(tert-butoxycarbonylamino)-2,3,5-trimethylphenoxy]acetic acid and 1-(tert-butoxycarbonyl)-4-aminopiperidine by the same manner as the Example 1.

Example 12

2-(4-Amino-2,3,5-trimethylphenoxy)-N-(4-piperidinyl)propamide (12)

The title compound (12) was obtained from 2-[4-(tert-butoxycarbonylamino)-2,3,5-trimethylphenoxy]propionic acid and 1-(tert-butoxycarbonyl)-4-aminopiperidine by the same manner as the Example 1.

Example 13

2-(4-Amino-2,3,5-trimethylphenoxy)-2-methyl-N-(4-piperidinyl)propamide (13)

The title compound (13) was obtained from 2-[4-(tert-butoxycarbonylamino)-2,3,5-trimethylphenoxy]-2-methyl-propionic acid and 1-(tert-butoxycarbonyl)-4-aminopiperidine by the same manner as the Example 1.

Example 14

2-(4-Amino-2,3,5-trimethylphenoxy)-N-ethyl-N-(4-piperidinyl)acetamide (14)

The title compound (14) was obtained from 2-[4-(tert-butoxycarbonylamino)-2,3,5-trimethylphenoxy]acetic acid and 1-(tert-butoxycarbonyl)-4-ethylaminopiperidine by the same manner as the Example 1.

Example 15

2-(4-Amino-2,3,5-trimethylphenoxy)-N-ethyl-N-(4-piperidinyl)propamide (15)

The title compound (15) was obtained from 2-[4-(tert-butoxycarbonylamino)-2,3,5-trimethylphenoxy]propionic acid and 1-(tert-butoxycarbonyl)-4-ethylaminopiperidine by the same manner as the Example 1.

Example 16

2-(4-Amino-2-chloro-3,5,6-trimethylphenoxy)-N-methyl-N-(4-piperidinyl)acetamide (16)

The title compound (16) was obtained from 2-[4-(tert-butoxycarbonylamino)-6-chloro-2,3,5-trimethylphenoxy]acetic acid and 1-(tert-butoxycarbonyl)-4-methylaminopiperidine by the same manner as the Example 1.

Example 17

2-(4-Amino-2-chloro-3,5,6-trimethylphenoxy)-N-(4-piperidinyl)acetamide (17)

The title compound (17) was obtained from 2-[4-(tert-butoxycarbonylamino)-6-chloro-2,3,5-trimethylphenoxy]acetic acid and 1-(tert-butoxycarbonyl)-4-aminopiperidine by the same manner as the Example 1.

Example 18

2-(4-Amino-2,3,5,6-tetramethylanilino)-N-ethyl-N-(4-piperidinyl)acetamide (18)

The title compound (18) was obtained from 2-[4-(tert-butoxycarbonylamino)-2,3,5,6-tetramethylanilino]acetic acid and 1-(tert-butoxycarbonyl)-4-ethylaminopiperidine by the same manner as the Example 1.

Example 19

2-(4-Amino-2,3,5,6-tetramethyl-N-methylanilino)-N-methyl-N-(4-piperidinyl)acetamide (19)

The title compound (19) was obtained from 2-[4-(tert-butoxycarbonylamino)-2,3,5,6-tetramethyl-N-methylanilino]acetic acid and 1-(tert-butoxycarbonyl)-4-methylaminopiperidine by the same manner as the Example 1.

Example 20

2-(4-Amino-2,3,5,6-tetramethylanilino)-N-methyl-N-(4-piperidinyl)propamide (20)

The title compound (20) was obtained from 2-[4-(tert-butoxycarbonylamino)-2,3,5,6-tetramethylanilino]propi onic acid and 1-(tert-butoxycarbonyl)-4-methylaminopiperidine by the same manner as the Example 1.

Example 21

2-[4-(Tert-butoxycarbonylamino)-2,3,5,6-tetramethylanilino]-N-(4-piperidinyl)acetamide (21)

A mixture solution of 2.2 g of 2-[4-(tert-butoxycarbonylamino)-2,3,5,6-tetramethylanilino]acetic acid, 1.67 ml of 1-benzyl-4-aminopiperidine, 10.47 g of 25% propane-phosphonic acid anhydride and 4.76 ml of triethylamine in 40 ml of methylene chloride was stirred over night at room temperature. Then, 20 ml of saturated sodium hydrogen carbonate solution was added to the reaction mixture, and the mixture was extracted with methylene chloride. The extract was washed with brine, dried and concentrated under reduced pressure to give a residue. The obtained residue was purified by silica gel column chromatography (methylene chloride:methanol=10:1) to give 2.48 g (73%) of 2-[4-(tert-butoxycarbonylamino)-2,3,5,6-tetramethylanilino]-N-(1-benzyl-4-piperidinyl)acetamide. Then, a mixture of 438 mg of the compound obtained and 40 mg of 20%-palladium hydroxide on carbon in 4 ml of methanol was stirred for 6 hours under 5 atm of hydrogen. Then, the catalyst was filtered off a Celite (trade name) pud and the filtrate was concentrated under reduced pressure to give a residue. The obtained residue was purified by amine-coated silica gel (Fuji Silysia Chemical Ltd.; NH-DM1020) column chromatography (methylene chloride:methanol=10:1) to give 293 mg (81%) of the above-mentioned compound (21).

Example 22

2-(4-Dimethylamino-2,3,5,6-tetramethylanilino)-N-ethyl-N-(4-piperidinyl)acetamide (22)

The title compound (22) was obtained from 2-(4-dimethylamino-2,3,5,6-tetramethylanilino)acetic acid and 1-(tert-butoxycarbonyl)-4-methylaminopiperidine by the same manner as the Example 1.

Example 23

2-(3-Amino-2,4,6-trimethylanilino)-N-methyl-N-(4-piperidinyl)acetamide (23)

The title compound (23) was obtained from 2-[3-(tert-butoxycarbonylamino)-2,4,6-trimethylanilino]acetic acid and 1-(tert-butoxycarbonyl)-4-methylaminopiperidine by the same manner as the Example 1.

Example 24

2-(3-Dimethylamino-2,4,6-trimethylanilino)-N-methyl-N-(4-piperidinyl)acetamide (24)

The title compound (24) was obtained from 2-(3-dimethylamino-2,4,6-trimethylanilino)acetic acid and 1-(tert-butoxycarbonyl)-4-methylaminopiperidine by the same manner as the Example 1.

Example 25

2-(2-Amino-4,5-dimethylanilino)-N-methyl-N-(4-piperidinyl)acetamide (25)

The title compound (25) was obtained from 2-[2-(tert-butoxycarbonylamino)-4,5-dimethylanilino]acetic acid and 1-(tert-butoxycarbonyl)-4-methylaminopiperidine by the same manner as the Example 1.

Example 26

2-(4-Amino-2,5-dichloroanilino)-N-methyl-N-(4-piperidinyl)acetamide (26)

The title compound (26) was obtained from 2-[4-(tert-butoxycarbonylamino)-2,5-dichloroanilino]acetic acid and 1-(tert-butoxycarbonyl)-4-methylaminopiperidine by the same manner as the Example 1.

Example 27

2-(4-Nitro-2,6-dichloroanilino)-N-methyl-N-(4-piperidinyl)acetamide (27)

The title compound (27) was obtained from 2-(4-nitro-2,6-dichloroanilino)acetic acid and 1-(tert-butoxycarbonyl)-4-methylaminopiperidine by the same manner as the Example 1.

Example 28

2-(4-Amino-2,3,5-trimethylphenoxy)-N-methyl-N-(1-phenethyl-4-piperidinyl)acetamide (28)

200 mg of phenethyl bromide was added to a mixture solution of 350 mg of the Compound (1) obtained in the Example 1 and 172 mg of triethylamine in 5 ml of acetonitrile, and the mixture was stirred for 5 hours at 60° C. Then, 5 ml of saturated ammonium chloride solution was added to the reaction mixture and the mixture was extracted with ethyl acetate. The extract was washed with brine, dried and concentrated under reduced pressure to give a residue. The obtained residue was purified by amine-coated silica gel (Fuji Silysia Chemical Ltd.; NH-DM1020) column chromatography (methylene chloride:methanol=20:1) to give 390 mg (83%) of the above-mentioned compound (28).

Example 29

2-(4-Amino-2,3,5-trimethylphenoxy)-N-[1-(2-anilino-2-oxyethyl)-4-piperidinyl]-N-methylacetamide (29)

The title compound (29) was obtained by the same manner as the Example 28 from the Compound (1) obtained in the Example 1 and N-phenyl-2-bromoacetamide.

Example 30

2-(4-Amino-2,3,5-trimethylphenoxy)-N-[1-(2-anilino-2-oxyethyl)-4-piperidinyl]-N-methylpropamide (30)

The title compound (30) was obtained by the same manner as the Example 28 from the Compound (2) obtained in the Example 2 and N-phenyl-2-bromoacetamide.

Example 31

2-(4-Amino-2,3,5-trimethylphenoxy)-N-methyl-N-(1-phenthyl-4-piperidinyl)propamide (31)

The title compound (31) was obtained by the same manner as the Example 28 from the Compound (2) obtained in the Example 2 and phenethyl bromide.

Example 32

2-(4-Amino-2,3,5-trimethylphenoxy)-N-[1-(2-(4-amino-2,3,5,6-tetramethyl)anilino-2-oxyethyl)-4-piperidinyl]-N-methyl-propamide (32)

The title compound (32) was obtained by the same manner as the Example 28 from the Compound (2) obtained in the Example 2 and N-(4-amino-2,3,5,6-tetramethyl)phenyl-2-bromoacetamide.

Example 33

2-(4-Amino-2,3,5-trimethylphenoxy)-N-methyl-N-[1-(2-quinolylmethyl)-4-piperidinyl]propamide (33)

The title compound (33) was obtained by the same manner as the Example 28 from the Compound (2) obtained in the Example 2 and 2-quinolylmethyl bromide.

Example 34

2-(4-Amino-2,3,5-trimethylphenoxy)-N-[1-(2-(4-amino-2,3,5,6-tetramethyl)anilino-2-oxyethyl)-4-piperidinyl]-N-methyl-acetamide (34)

The title compound (34) was obtained by the same manner as the Example 28 from the Compound (1) obtained in the Example 1 and N-(4-amino-2,3,5,6-tetramethyl)phenyl-2-bromoacetamide.

Example 35

2-(4-Amino-2,3,5-trimethylphenoxy)-N-[1-(2 -benzimidazolylmethyl)-4-piperidinyl]-N-methylpropamide (35)

The title compound (35) was obtained by the same manner as the Example 28 from the Compound (2) obtained in the Example 2 and 2-benzimidazolylmethyl bromide.

Example 36

2-(2-Amino-4,6-dimethylphenoxy)-N-methyl-N-[1-(2-pyridylmethyl)-4-piperidinyl]acetamide (36)

The title compound (36) was obtained by the same manner as the Example 28 from the Compound (4) obtained in the Example 4 and 2-pyridylmethyl bromide.

Example 37

2-(4-Amino-2,3,6-trimethylphenoxy)-N-methyl-N-[1-(2-phenethyl)-4-piperidinyl]acetamide (37)

The title compound (37) was obtained by the same manner as the Example 28 from the Compound (5) obtained in the Example 5 and phenethyl bromide.

Example 38

2-(4-Amino-2,3,5-trimethylphenoxy)-2-methyl-N-methyl-N-[1-(2-phenethyl)-4-piperidinyl]propamide (38)

The title compound (38) was obtained by the same manner as the Example 28 from the Compound (3) obtained in the Example 3 and phenethyl bromide.

Example 39

2-(4-Amino-2,3,6-trimethylphenoxy)-N-[1-(2-(4-amino-2,5-dichloroanilino)-2-oxyethyl)-4-piperidinyl]-N-methylacetamide (39)

The title compound (39) was obtained by the same manner as the Example 28 from the Compound (5) obtained in the Example 5 and N-(4-amino-2,5-dichloro)phenyl-2-bromoacetamide.

Example 40

2-(4-Amino-2,3,5,6-tetramethylanilino)-N-methyl-N-[1-(2-phenethyl)-4-piperidinyl]acetamide (40)

The title compound (40) was obtained by the same manner as the Example 28 from the Compound (10) obtained in the Example 10 and phenethyl bromide.

Example 41

2-(4-Amino-2,3,5,6-tetramethylanilino)-N-[1-(2-anilino-2-oxyethyl)-4-piperidinyl]-N-methylacetamide (41)

The title compound (41) was obtained by the same manner as the Example 28 from the Compound (10) obtained in the Example 10 and N-phenyl-2-bromoacetamide.

Example 42

2-(4-Amino-2,3,5-trimethylphenoxy)-2-methyl-N-[1-(2-anilino-2-oxyethyl)-4-piperidinyl]-N-methyl-propamide (42)

The title compound (42) was obtained by the same manner as the Example 28 from the Compound (3) obtained in the Example 3 and N-phenyl-2-bromoacetamide.

Example 43

2-(4-Amino-2,3,5-trimethylphenoxy)-N-[1-(2-(2,5-dimethyl-4-hydroxy)anilino-2-oxyethyl)-4-piperidinyl]-N-methylacetamide (43)

The title compound (43) was obtained by the same manner as the Example 28 from the Compound (1) obtained in the Example 1 and N-(2,5-dimethyl-4-hydroxy)phenyl-2-bromoacetamide.

Example 44

2-(4-Amino-2,3,5-trimethylphenoxy)-N-methyl-N-[1-(2-quinolylmethyl)-4-piperidinyl]acetamide (44)

The title compound (44) was obtained by the same manner as the Example 28 from the Compound (1) obtained in the Example 1 and 2-chloromethylquinoline.

Example 45

2-(4-Amino-2,3,5-trimethylphenoxy)-N-[1-(2-(3-chloro-2-methyl)anilino-2-oxyethyl)-4-piperidinyl]-N-methylacetamide The title compound (45) was obtained by the same manner as the Example 28 from the Compound (1) obtained in the Example 1 and N-(3-chloro-2-methyl)phenyl-2-bromoacetamide.

Example 46

2-(4-Amino-2,3,5-trimethylphenoxy)-N-[1-(2-(2-tert-butyl)anilino-2-oxyethyl)-4-piperidinyl]-N-methylacetamide (46)

The title compound (46) was obtained by the same manner as the Example 28 from the Compound (1) obtained in the Example 1 and N-(2-tert-butyl)phenyl-2-bromoacetamide.

Example 47

2-(4-Amino-2,3,5-trimethylphenoxy)-N-[1-(2-(2,6-dimethyl)anilino-2-oxyethyl)-4-piperidinyl]-N-methylacetamide (47)

The title compound (47) was obtained by the same manner as the Example 28 from the Compound (1) obtained in the Example 1 and N-(2,6-dimethyl)phenyl-2-bromoacetamide.

Example 48

2-(4-Amino-2,3,5-trimethylphenoxy)-2-methyl-N-[1-(2-(3-chloro-2-methyl)anilino-2-oxyethyl)-4-piperidinyl]-N-methylpropamide (48)

The title compound (48) was obtained by the same manner as the Example 28 from the Compound (3) obtained in the Example 3 and N-(3-chloro-2-methyl)phenyl-2-bromoacetamide.

Example 49

2-(4-Amino-2,3,5-trimethylphenoxy)-2-methyl-N-[1-(2-tert-butylanilino-2-oxyethyl)-4-piperidinyl]-N-methylpropamide (49)The title compound (49) was obtained by the same manner as the Example 28 from the Compound (3) obtained in the Example 3 and N-(2-tert-butylmethyl)phenyl-2-bromoacetamide.

Example 50

2-(4-Amino-2,3,5-trimethylphenoxy)-2-methyl-N-[1-(2-(2,6-dimethyl)anilino-2-oxyethyl)-4-piperidinyl]-N-methylpropamide (50)

The title compound (50) was obtained by the same manner as the Example 28 from the Compound (3) obtained in the Example 3 and N-(2,6-dimethyl)phenyl-2-bromoacetamide.

Example 51

2-(5-Amino-4-chloro-2-methoxyphenoxy)-N-[1-(2-anilino-2-oxyethyl)-4-piperidinyl]-N-ethylacetamide (51)

The title compound (51) was obtained by the same manner as the Example 28 from the Compound (8) obtained in the Example 8 and N-phenyl-2-bromoacetamide.

Example 52

2-(5-Amino-4-chloro-2-methoxyphenoxy)-N-ethyl-N-[1-(2-(2,4,6-trimethyl)anilino-2-oxyethyl)-4-piperidinyl]acetamide (52)

The title compound (52) was obtained by the same manner as the Example 28 from the Compound (8) obtained in the Example 8 and N-(2,4,6-trimethyl)phenyl-2-bromoacetamide.

Example 53

2-(4-Amino-2,3,5-trimethylphenoxy)-N-methyl-N-[1-(3-phenyl-2-(E)-propenyl-4-piperidinyl]acetamide (53)

The title compound (53) was obtained by the same manner as the Example 28 from the Compound (1) obtained in the Example 1 and cinnamyl bromide.

Example 54

2-(4-Amino-2,3,5-trimethylphenoxy)-N-methyl-N-[1-(1-phenyl-1-cyclopropane)methyl-4-piperidinyl]acetamide (54)

The title compound (54) was obtained by the same manner as the Example 28 from the Compound (1) obtained in the Example 1 and 1-phenyl-1-cyclopropylmethyl bromide.

Example 55

2-(4-Amino-2,3,5-trimethylphenoxy)-N-methyl-N-[1-(2-(1-phenylcyclopropyl)amino-2-oxyethyl-4-piperidinyl]acetamide (55)

The title compound (55) was obtained by the same manner as the Example 28 from the Compound (1) obtained in the Example 1 and N-(1-phenyl)cyclopropyl-2-bromoacetamide.

Example 56

2-(4-Amino-2,3,5-trimethylphenoxy)-N-methyl-N-[1-(2-phenyl-2-oxyethyl)-4-piperidinyl]acetamide (56)

The title compound (56) was obtained by the same manner as the Example 28 from the Compound (1) obtained in the Example 1 and phenacyl bromide.

Example 57

2-(5-Amino-2-methoxyphenoxy)-N-ethyl-N-[1-(2-(2,4,6-trimethyl)anilino-2-oxyethyl)-4-piperidinyl]acetamide (57)

The title compound (57) was obtained by the same manner as the Example 28 from the Compound (7) obtained in the Example 7 and N-(2,4,6-trimethyl)phenyl-2-bromoacetamide.

Example 58

2-(5-Amino-2-methoxyphenoxy)-N-methyl-N-[1-(2-(2,4,6-trimethyl)anilino-2-oxyethyl)-4-piperidinyl]acetamide (58)

The title compound (58) was obtained by the same manner as the Example 28 from the Compound (6) obtained in the Example 6 and N-(2,4,6-trimethyl)phenyl-2-bromoacetamide.

Example 59

2-(5-Amino-2-methoxyphenoxy)-N-[1-(2-anilino-2-oxyethyl)-4-piperidinyl]-N-methylacetamide (59)

The title compound (59) was obtained by the same manner as the Example 28 from the Compound (6) obtained in the Example 6 and N-phenyl-2-bromoacetamide.

Example 60

2-(4-Amino-2,3,5-trimethylphenoxy)-N-[1-(2-(2-tert-butylanilino)-2-oxyethyl)-4-piperidinyl]-N-methylpropamide (60)

The title compound (60) was obtained by the same manner as the Example 28 from the Compound (2) obtained in the Example 2 and N-(2-tert-butyl)phenyl-2-bromoacetamide.

Example 61

2-(4-Amino-2,3,5-trimethylphenoxy)-N-[1-(2-(2,6-dimethylanilino)-2-oxyethyl)-4-piperidinyl]-N-methylpropamide (61)

The title compound (61) was obtained by the same manner as the Example 28 from the Compound (2) obtained in the Example 2 and N-(2,6-dimethyl)phenyl-2-bromoacetamide.

Example 62

2-(4-Amino-2,3,5-trimethylphenoxy)-N-methyl-N-[1-(3-phenyl-2-(E)-propenyl)-4-piperidinyl]propamide (62)

The title compound (62) was obtained by the same manner as the Example 28 from the Compound (2) obtained in the Example 2 and cinnamyl bromide.

Example 63

2-(4-Amino-2,3,5-trimethylphenoxy)-N-methyl-N-[1-(trans-2-phenyl-1-cyclopropylmethyl)-4-piperidinyl]propamide (63)

The title compound (63) was obtained by the same manner as the Example 28 from the Compound (2) obtained in the Example 2 and trans-2-phenyl-1-cyclopropylmethyl bromide.

Example 64

2-(4-Amino-2,3,5-trimethylphenoxy)-N-methyl-N-[1-(2-(1-phenylcyclopropyl)amino-2-oxyethyl)-4-piperidinyl]propamide (64)

The title compound (64) was obtained by the same manner as the Example 28 from the Compound (2) obtained in the Example 2 and N-(1-phenyl)cyclopropyl-2-bromoacetamide.

Example 65

2-(4-Amino-2,3,5-trimethylphenoxy)-N-methyl-N-[1-(2-hydroxy-3-phenoxy)propyl-4-piperidinyl]acetamide (65)

A mixture solution of 330 mg of Compound (1) obtained in the Example 1 and 162 mg of glycidyl phenyl ether in 8 ml of iso-propanol was stirred for 4 hours at 80° C. Then, the reaction mixture was concentrated under reduced pressure, and the resultant residue was purified by amine-coated silica gel (Fuji Silysia Chemical Ltd.; NH-DM1020) column chromatography (chloroform:methanol=30:1) to give 266 mg (54%) of the title compound (65).

Example 66

2-(4-Amino-2,3,5-trimethylphenoxy)-N-methyl-N-[1-(2-trans-2-phenyl-1-cyclopropyl)amino-2-oxyethyl)-4-piperidinyl]acetamide (66)

The title compound (66) was obtained by the same manner as the Example 28 from the Compound (1) obtained in the Example 1 and 2-bromo-N-(trans-2-phenylcyclopropyl)acetamide.

Example 67

2-(4-Amino-2,3,5-trimethylphenoxy)-2-methyl-N-methyl-N-[1-(3-phenyl-2-(E)-propenyl)-4-piperidinyl]propamide (67)

The title compound (67) was obtained by the same manner as the Example 28 from the Compound (3) obtained in the Example 3 and cinnamy bromide.

Example 68

2-(4-Amino-2,3,5-trimethylphenoxy)-2-methyl-N-methyl-N-[1-(1-phenyl-1-cyclopropane)methyl-4-piperidinyl]propamide (68)

The title compound (68) was obtained by the same manner as the Example 28 from the Compound (3) obtained in the Example 3 and 1-phenyl-1-cyclopropylmethyl bromide.

Example 69

2-(4-Amino-2,3,5-trimethylphenoxy)-2-methyl-N-methyl-N-[1-(2-(1-phenylcyclopropyl)amino-2-oxyethyl)-4-piperidinyl]propamide (69)

The title compound (69) was obtained by the same manner as the Example 28 from the Compound (3) obtained in the Example 3 and N-(1-phenyl)cyclopropyl-2-bromoacetamide.

Example 70

2-(4-Amino-2,3,5,6-tetramethylanilino)-N-methyl-N-[1-(1-phenyl-1-cyclopropane)methyl-4-piperidinyl]acetamide (70)

The title compound (70) was obtained by the same manner as the Example 28 from the Compound (10) obtained in the Example 10 and 1-phenyl-1-cyclopropylmethyl bromide.

Example 71

2-(4-Amino-2,3,5-trimethylphenoxy)-N-[1-(2-anilino-2-oxyethyl)-4-piperidinyl]-N-ethylacetamide (71)

The title compound (71) was obtained by the same manner as the Example 28 from the Compound (14) obtained in the Example 14 and N-phenyl-2-bromoacetamide.

Example 72

2-(4-Amino-2-chloro-3,5,6-trimethylphenoxy)-N-methyl-N-[1-(2-(1-phenylcyclopropyl)amino-2-oxyethyl)-4-piperidinyl]-acetamide (72)

The title compound (72) was obtained by the same manner as the Example 28 from the Compound (16) obtained in the Example 16 and N-(1-phenyl)cyclopropyl-2-bromoacetamide.

Example 73

2-(4-Amino-2-chloro-3,5,6-trimethylphenoxy)-N-[1-(2-anilino-2-oxyethyl)-4-piperidinyl]-N-ethylacetamide (73)

The title compound (73) was obtained by the same manner as the Example 28 from the Compound (9) obtained in the Example 9 and N-phenyl-2-bromoacetamide.

Example 74

2-(4-Amino-2,3,5-trimethylphenoxy)-N-ethyl-N-[1-(3-phenyl-2-(E)-propenyl)-4-piperidinyl]acetamide (74)

The title compound (74) was obtained by the same manner as the Example, 28 from the Compound (14) obtained in the Example 14 and cinnamyl bromide.

Example 75

2-(4-Amino-2,3,5-trimethylphenoxy)-N-[1-(2-anilino-2-oxyethyl)-4-piperidinyl]-N-ethylpropamide (75)

The title compound (75) was obtained by the same manner as the Example 28 from the Compound (15) obtained in the Example 15 and N-phenyl-2-bromoacetamide.

Example 76

2-(4-Amino-2,3,5,6-tetramethylanilino)-N-ethyl-N-[1-(2-phenethyl)-4-piperidinyl]acetamide (76)

The title compound (76) was obtained by the same manner as the Example 28 from the Compound (18) obtained in the Example 18 and phenethyl bromide.

Example 77

2-(4-Amino-2,3,5-trimethylphenoxy)-N-ethyl-N-[1-(3-phenyl-2-(E)-propenyl)-4-piperidinyl]propamide (77)

The title compound (77) was obtained by the same manner as the Example 28 from the Compound (15) obtained in the Example 15 and cinnamyl bromide.

Example 78

2-(4-Amino-2,3,5,6-tetramethylanilino)-N-ethyl-N-[1-(3-phenyl-2-(E)-propenyl)-4-piperidinyl]acetamide (78)

The title compound (78) was obtained by the same manner as the Example 28 from the Compound (18) obtained in the Example 18 and cinnamyl bromide.

Example 79

2-(4-Amino-2,3,5-trimethylphenoxy)-2-methyl-N-[1-(2-(4-amino-2,5-dichloro)anilino-2-oxyethyl)-4-piperidinyl]-N-methylpropamide (79)

The title compound (79) was obtained by the same manner as the Example 28 from the Compound (3) obtained in the Example 3 and N-(4-amino-2,5-dichloro)phenyl-2-bromoacetamide.

Example 80

2-(4-Amino-2,3,5-trimethylphenoxy)-2-methyl-N-[1-(3-phenyl-2-(E)-propenyl)-4-piperidinyl]propamide (80)

The title compound (80) was obtained by the same manner as the Example 28 from the Compound (13) obtained in the Example 13 and cinnamy bromide.

Example 81

2-(4-Amino-2,3,5-trimethylphenoxy)-2-methyl-N-[1-(1-phenyl-1-cyclopropane)methyl-4-piperidinyl]propamide (81)

The title compound (81) was obtained by the same manner as the Example 28 from the Compound (13) obtained in the Example 13 and 1-phenyl-1-cyclopropylmethyl bromide.

Example 82

2-(4-Amino-2,3,5-trimethylphenoxy)-2-methyl-N-[1-(2-anilino-2-oxyethyl)-4-piperidinyl]propamide (82)

The title compound (82) was obtained by the same manner as the Example 28 from the Compound (13) obtained in the Example 13 and N-phenyl-2-bromoacetamide.

Example 83

2-(4-Amino-2,3,5-trimethylphenoxy)-N-[1-(2-anilino-2-oxyethyl)-4-piperidinyl]propamide (83)

The title compound (83) was obtained by the same manner as the Example 28 from the Compound (12) obtained in the Example 12 and N-phenyl-2-bromoacetamide.

Example 84

2-(4-Amino-2,3,5-trimethylphenoxy)-N-[1-(3-phenyl-2-(E)-propenyl)-4-piperidinyl]propamide (84)

The title compound (84) was obtained by the same manner as the Example 28 from the Compound (12) obtained in the Example 12 and cinnamyl bromide.

Example 85

2-(4-Amino-2,3,5-trimethylphenoxy)-N-[1-(2-anilino-2-oxyethyl)-4-piperidinyl]acetamide (85)

The title compound (85) was obtained by the same manner as the Example 28 from the Compound (11) obtained in the Example 11 and N-phenyl-2-bromoacetamide.

Example 86

2-(4-Amino-2,3,5-trimethylphenoxy)-N-[1-(3-phenyl-2-(E)-propenyl)-4-piperidinyl]acetamide (86)

The title compound (86) was obtained by the same manner as the Example 28 from the Compound (11) obtained in the Example 11 and cinnamyl bromide.

Example 87

2-(4-Amino-2,3,5-trimethylphenoxy)-N-ethyl-N-[1-(1-phenyl-1-cyclopropane)methyl-4-piperidinyl]propamide (87)

The title compound (87) was obtained by the same manner as the Example 28 from the Compound (15) obtained in the Example 15 and 1-phenyl-1-cyclopropylmethyl bromide.

Example 88

2-(4-Amino-2,3,5,6-tetramethylanilino)-N-ethyl-N-[1-(1-phenyl-1-cyclopropane)methyl-4-piperidinyl]acetamide (88)

The title compound (88) was obtained by the same manner as the Example 28 from the Compound (18) obtained in the Example 18 and 1-phenyl-1-cyclopropylmethyl bromide.

Example 89

2-(4-Amino-2,3,5-trimethylphenoxy)-N-[1-(2-(4-amino-2,5-dichloro)anilino-2-oxyethyl)-4-piperidinyl]-N-methylacetamide (89)

The title compound (89) was obtained by the same manner as the Example 28 from the Compound (1) obtained in the Example 1 and N-(4-amino-2,5-dichloro)phenyl-2-bromoacetamide.

Example 90

2-(4-Amino-2,3,5-trimethylphenoxy)-N-methyl-N-[1-(1-phenyl-1-cyclopropane)methyl-4-piperidinyl]propamide (90)

The title compound (90) was obtained by the same manner as the Example 28 from the Compound (2) obtained in the Example 2 and 1-phenyl-1-cyclopropylmethyl bromide.

Example 91

2-(4-Amino-2-chloro-3,5,6-trimethylphenoxy)-N-[1-(2-anilino-2-oxyethyl)-4-piperidinyl]acetamide (91)

The title compound (91) was obtained by the same manner as the Example 28 from the Compound (17) obtained in the Example 17 and N-phenyl-2-bromoacetamide.

Example 92

2-(4-Amino-2-chloro-3,5,6-trimethylphenoxy)-N-[1-(2-(4-amino-2,5-dichloro)anilino-2-oxyethyl)-4-piperidinyl]-N-methylacetamide (92)

The title compound (92) was obtained by the same manner as the Example 28 from the Compound (16) obtained in the Example 16 and N-(4-amino-2,5-dichloro) phenyl-2-bromoacetamide.

Example 93

2-(4-Amino-2-chloro-3,5,6-trimethylphenoxy)-N-[1-(2-(2,5-dimethyl-4-hydroxy)anilino-2-oxyethyl)-4-piperidinyl]-N-ethylacetamide (93)

The title compound (93) was obtained by the same manner as the Example 28 from the Compound (9) obtained in the Example 9 and N-(2,5-dimethyl-4-hydroxy)phenyl-2-bromoacetamide.

Example 94

2-(4-Amino-2,3,5,6-tetramethylanilino)-N-ethyl-N-[1-(trans-2-phenyl-1-cyclopropylmethyl)-4-piperidinyl]acetamide (94)

The title compound (94) was obtained by the same manner as the Example 28 from the Compound (18) obtained in the Example 18 and trans-2-phenyl-1-cyclopropylmethyl bromide.

Example 95

2-(4-Amino-2,3,5-trimethylphenoxy)-N-[1-(trans-2-phenyl-1-cyclopropylmethyl)-4-piperidinyl]acetamide (95)

The title compound (95) was obtained by the same manner as the Example 28 from the Compound (11) obtained in the Example 11 and trans-2-phenyl-1-cyclopropylmethyl bromide.

Example 96

2-(4-Amino-2,3,5-trimethylphenoxy)-N-[1-(1-phenyl-1-cyclopropane)methyl-4-piperidinyl]acetamide (96)

The title compound (96) was obtained by the same manner as the Example 28 from the Compound (11) obtained in the Example 11 and 1-phenyl-1-cyclopropylmethyl bromide.

Example 97

2-(4-Amino-2,3,5-trimethylphenoxy)-N-(1-(2-phenethyl)-4-piperidinyl)acetamide (97)

The title compound (97) was obtained by the same manner as the Example 28 from the Compound (11) obtained in the Example 11 and phenethyl bromide.

Example 98

2-(4-Amino-2,3,5-trimethylphenoxy)-2-methyl-N-[1-(2-(2,6-dimethylanilino)-2-oxyethyl)-4-piperidinyl]propamide (98)

The title compound (98) was obtained by the same manner as the Example 28 from the Compound (13) obtained in the Example 13 and N-(2,6-dimethylphenyl)-2-bromoacetamide.

Example 99

2-(4-Amino-2,3,5-trimethylphenoxy)-2-methyl-N-[1-(trans-2-phenyl-1-cyclopropylmethyl)-4-piperidinyl propamide (99)

The title compound (99) was obtained by the same manner as the Example 28 from the Compound (13) obtained in the Example 13 and trans-2-phenyl-1-cyclopropylmethyl bromide.

Example 100

2-(4-Amino-2,3,5-trimethylphenoxy)-2-methyl-N-[1-(2-(2-tert-butylanilino)-2-oxyethyl)-4-piperidinyl] propamide (100)

The title compound (100) was obtained by the same manner as the Example 28 from the Compound (13) obtained in the Example 13 and N-(2-tert-butylphenyl)-2-bromoacetamide.

Example 101

2-(4-Amino-2,3,5-trimethylphenoxy)-N-[1-(1-phenyl-1-cyclopropane)methyl-4-piperidinyl]propamide (101)

The title compound (101) was obtained by the same manner as the Example 28 from the Compound (12) obtained in the Example 12 and 1-phenyl-1-cyclopropylmethyl bromide.

Example 102

2-(4-Amino-2,3,5-trimethylphenoxy)-N-[1-(2-(1-phenylcyclopropyl)amino-2-oxyethyl]-4-piperidinyl] propamide (102)

The title compound (102) was obtained by the same manner as the Example 28 from the Compound (12) obtained in the Example 12 and N-(1-phenyl)cyclopropyl-2-bromoacetamide.

Example 103

2-(4-Amino-2,3,5-trimethylphenoxy)-N-methyl-N-[1-(2-hydroxy-3-phenoxy)propyl-4-piperidinyl]propamide (103)

The title compound (103) was obtained by the same manner as the Example 65 from the Compound (2) obtained in the Example 2.

Example 104

2-(4-Amino-2,3,5-trimethylphenoxy)-N-[1-(2-(1-phenylcyclopropyl)amino-2-oxyethyl)-4-piperidinyl]acetamide (104)

The title compound (104) was obtained by the same manner as the Example 28 from the Compound (11) obtained in the Example 11 and N-(1-phenyl)cyclopropyl-2-bromoacetamide.

Example 105

2-(4-Amino-2,3,5-trimethylphenoxy)-N-methyl-N-[1-(2-(N-methylanilino)-2-oxyethyl)-4-piperidinyl]acetamide (105)

The title compound (105) was obtained by the same manner as the Example 28 from the Compound (1) obtained in the Example 1 and N-methyl-N-phenyl-2-bromoacetamide.

Example 106

2-(4-Amino-2,3,5-trimethylphenoxy)-N-[1-(trans-2-phenyl-1-cyclopropylmethyl)-4-piperidinyl]propamide (106)

The title compound (106) was obtained by the same manner as the Example 28 from the Compound (12) obtained in the Example 12 and trans-2-phenyl-1-cyclopropylmethyl bromide.

Example 107

2-(4-Amino-2,3,5-trimethylphenoxy)-2-methyl-N-[1-(2-(2,5-dimethyl-4-hydroxy)anilino-2-oxyethyl)-4-piperidinyl]-N-methylpropamide (107)

The title compound (107) was obtained by the same manner as the Example 28 from the Compound (3) obtained in the Example 3 and N-(2,5-dimethyl-4-hydroxy)phenyl-2-bromoacetamide.

Example 108

2-(4-Amino-2,3,5-trimethylphenoxy)-N-[1-(2-(N-methylanilino)-2-oxyethyl)-4-piperidinyl]acetamide (108)

The title compound (108) was obtained by the same manner as the Example 28 from the Compound (11) obtained in the Example 11 and N-methyl-N-phenyl-2-bromoacetamide.

Example 109

3{4-[[2-(4-Amino-2,3,5,6-tetramethylanilino)-acetyl](methyl)amino]-1-piperidino}-2-phenylpropionic acid (109)

A mixture solution of 144 mg of {4-[(tert-butoxycarbonyl)amino]-2,3,5,6-tetramethylanilino}acetic acid, 156 mg of ethyl 3-[4-(methylamino)-1-piperidino]-2-phenyl propionate, 860 mg of 25% propanephosphonic acid anhydride and 436 µl of triethylamine in 2 ml of methylene chloride was stirred over night at room temperature. Then, saturated sodium hydrogen carbonate solution was added to the reaction mixture, and the mixture was extracted with methylene chloride. The extract was washed with brine, dried, filtrated, and concentrated under reduced pressure to give a residue. The obtained residue was purified by silica gel column chromatography (methylene chloride:methanol=10:1) to give 180 mg (67%) of ethyl 3-{4-[({4-[(tert-butoxycarbonyl)amino]-2,3,5,6-tetramethylanilino}-acetyl)(methyl)amino]-1-piperidino}-2-phenyl propionate. Then, 178 mg of the obtained ethyl propionate was dissolved in 3 ml of 1,4-dioxane and 3 ml of 0.3N-litium hydroxide solution was added to this solution, then the mixture solution was stirred for 4 hours at room temperature. Then, the reaction mixture was acidified (pH 4) with conc. HCl solution and the mixture was extracted with ethyl acetate. The extract was washed with brine, dried, filtrated and concentrated under reduced pressure to give a residue. Then, a mixture solution of the obtained residue in methylene chloride and trifluoroacetic acid (4:1) was stirred for 1 hour at room temperature. Then, the solvent was removed and the residue was dissolved in water and then treated with 4N-HCl solution to give 130 mg (81%) of the above-mentioned compound (109).

Example 110

2-(4-Amino-2,3,5,6-tetramethylanilino)-N-(1-benzyl-4-piperidinyl]-N-methylacetamide (110)

The title compound (110) was obtained by the same manner as the Example 28 from the Compound (10) obtained, in the Example 10 and benzyl bromide.

Example 111

2-(4-Amino-2,3,5,6-tetramethylanilino)-N-methyl-[1-(2-phenyl-2-oxyethyl)-4-piperidinyl]acetamide (111)

The title compound (111) was obtained by the same manner as the Example 28 from the Compound (10) obtained in the Example 10 and phenacyl bromide.

Example 112

2-(4-Amino-2,3,5,6-tetramethylanilino)-N-[1-(2-hydroxy-2-phenylethyl)-4-piperidinyl]-N-methylacetamide (112)

To a solution of the Compound (111) obtained in the Example 111 in methanol was added 1.0 equivalent of sodium borohydride at 0° C., and the mixture was stirred for 2.5 hours at room temperature. Then, the solvent was removed and the obtained residue was purified by amine-coated silica gel (Fuji Silysia Chemical Ltd.; NH-DM1020) column chromatography (ethyl acetate hexane:methanol=10:10:1) to give the above-mentioned compound (112) in 75% yield.

Example 113

2-(4-Amino-2,3,5,6-tetramethylanilino)-N-[1-(cyclopropylmethyl)-4-piperidinyl]-N-methylacetamide (113)

The title compound (113) was obtained by the same manner as the Example 28 from the Compound (10) obtained in the Example 10 and cyclopropylmethyl bromide.

Example 114

2-(4-Amino-2,3,5,6-tetramethylanilino)-N-methyl-
N-[1-(4-pyridylmethyl)-4-piperidinyl]acetamide
(114)

The title compound (114) was obtained by the same manner as the Example 28 from the Compound (10) obtained in the Example 10 and 4-picolyl chloride.

Example 115

4-({4-[[(4-Amino-2,3,5,6-tetramethylanilino)-acetyl]
(methyl)amino]-1-piperidino}methyl)benzoic Acid
(115)

A mixture solution of the compound obtained from the Compound (10) in the Example 10 and tert-butyl 4-(bromomethyl)benzoate by the same manner as the Example 28 in 6N-HCl solution was refluxed for 2 hours. Then, the solvent was removed to give the title compound (115).

Example 116

4-({4-[[(4-Amino-2,3,5,6-tetramethylanilino)-acetyl]
(methyl)amino]-1-piperidino}methyl)benzamide
(116)

The title compound (116) was obtained by the same manner as the Example 28 from the Compound (10) obtained in the Example 10 and 4-bromomethylbenzamide.

Example 117

2-(4-Amino-2,3,5,6-tetramethylanilino)-N-[1-(2-hydroxyethyl)-4-piperidinyl]-N-methylacetamide (117)

The title compound (117) was obtained by the same manner as the Example 28 from the Compound (10) obtained in the Example 10 and 2-bromoethanol.

Example 118

3-{4-[[(4-Amino-2,3,5,6-tetramethylanilino)-acetyl]
(methyl)amino]-1-piperidino}propionic Acid (118)

The title compound (118) was obtained by the same manner as the Example 115 from the Compound (10) obtained in the Example 10 and tert-butyl 3-bromopropionate.

Example 119

2-(4-Amino-2,3,5,6-tetramethylanilino)-N-methyl-
N-{1-[2-(4-morpholinyl)ethyl]-4-
piperidinyl}acetamide (119)

The title compound (119) was obtained by the same manner as the Example 28 from the Compound (10) obtained in the Example 10 and N-(2-bromoethyl)morpholine hydrochloride.

Example 120

2-(4-Amino-2,3,5,6-tetramethyl-N-methylanilino)-
N-methyl-N-[1-(2-phenethyl)-4-piperidinyl]acetamide (120)

The title compound (120) was obtained by the same manner as the Example 28 from the Compound (19) obtained in the Example 19 and phenethyl bromide.

Example 121

2-(4-Amino-2,3,5,6-tetramethylanilino)-N-[1-(cyclopropylmethyl)-4-piperidinyl]-N-methylpropamide
(121)

The title compound (121) was obtained by the same manner as the Example 28 from the Compound (20) obtained in the Example 20 and cyclopropylmethy bromide.

Example 122

2-(4-Amino-2,3,5,6-tetramethylanilino)-N-methyl-
N-[1-(2-phenethyl)-4-piperidinyl]propamide (122)

The title compound (122) was obtained by the same manner as the Example 28 from the Compound (20) obtained in the Example 20 and phenethyl bromide.

Example 123

2-(4-Amino-2,3,5,6-tetramethylanilino)-N-[1-(2-
phenethyl)-4-piperidinyl]acetamide (123)

A mixture solution of the compound obtained from the Compound (21) in the Example 21 and phenethyl bromide by the same manner as the Example 28 in methylene chloride and trifluoroacetic acid (4:1) was stirred for 1 hour at 0° C. Then, the solvent was removed to give a residue, and the obtained residue was purified by amine-coated silica gel (Fuji Silysia Chemical Ltd.; NH-DM1020) column chromatography (methylene chloride:methanol=10:1) to give the above-mentioned compound (123) in 60% yield.

Example 124

2-(4-Dimethylamino-2,3,5,6-tetramethylanilino)-N-
methyl-N-[1-(2-phenethyl)-4-piperidinyl]acetamide
(124)

The title compound (124) was obtained by the same manner as the Example 28 from the Compound (22) obtained in the Example 22 and phenethyl bromide.

Example 125

2-(3-Amino-2,4,6-trimethylanilino)-N-methyl-N-[1-
(3-phenyl-2-(E)-propenyl)-4-piperidinyl]acetamide
(125)

The title compound (125) was obtained by the same manner as the Example 28 from the Compound (23) obtained in the Example 23 and cinnamyl bromide.

Example 126

2-(3-Amino-2,4,6-tirmethylanilino)-N-[1-(2-hydroxy-3-phenoxy)propyl-4-piperidinyl]-N-methylacetamide (126)

The title compound (126) was obtained by the same manner as the Example 65 from the Compound (23) obtained in the Example 23.

Example 127

2-(3-Amino-2,4,6-trimethylanilino)-N-methyl-N-[1-(2-phenyl-2-oxyethyl)-4-piperidinyl]acetamide (127)

The title compound (127) was obtained by the same manner as the Example 28 from the Compound (23) obtained in the Example 23 and phenacyl bromide.

Example 128

2-(3-Amino-2,4,6-trimethylanilino)-N-(1-benzoyl-4-piperidinyl)-N-methylacetamide (128)

A mixture solution of 300 mg of the compound (23) obtained in the Example 23, 114 μl of benzoyl chloride and 206 μl of triethylamine in 5 ml of methylene chloride were stirred for 2 hoursat 0° C. After the reaction, the solvent was removed and the obtained residue was purified by amine-coated silica gel (Fuji Silysia Chemical Ltd.; NH-DM1020) column chromatography (methylene chloride:ether=1:1) to give the above-mentioned compound (128) in 66% yield.

Example 129

2-(3-Amino-2,4,6-trimethylanilino)-N-[1-(cyclopropylmethyl)-4-piperidinyl]-N-methylacetamide (129)

The title compound (129) was obtained by the same manner as the Example 28 from the Compound (23) obtained in the Example 23 and cyclopropylmethyl bromide.

Example 130

2-(3-Amino-2,4,6-trimethylanilino)-N-methyl-N-[1-(phenylsulfonyl)-4-piperidinyl]acetamide (130)

The title compound (130) was obtained by the same manner as the Example 128 from the Compound (23) obtained in the Example 23 and benzenesulfonyl chloride.

Example 131

2-(3-Amino-2,4,6-trimethylanilino)-N-(1-benzyl-4-piperidinyl)-N-methylacetamide (131)

The title compound (131) was obtained by the same manner as the Example 28 from the Compound (23) obtained in the Example 23 and benzyl bromide.

Example 132

2-(3-Amino-2,4,6-trimethylanilino)-N-(1-butyl-4-piperidinyl)-N-methylacetamide (132)

The title compound (132) was obtained by the same manner as the Example 28 from the Compound (23) obtained in the Example 23 and bromobutane.

Example 133

2-(3-Amino-2,4,6-trimethylanilino)-N-methyl-N-[1-(2-naphthyl)methyl-4-piperidinyl]acetamide (133)

The title compound (133) was obtained by the same manner as the Example 28 from the Compound (23) obtained in the Example 23 and 2-(bromomethyl)naphthalene.

Example 134

2-(3-Amino-2,4,6-trimethylanilino)-N-methyl-N-[1-(3-trifluoromethylbenzoyl)-4-piperidinyl]acetamide (134)

The title compound (134) was obtained by the same manner as the Example 128 from the Compound (23) obtained in the Example 23 and 3-(trifluoromethyl)benzoyl chloride.

Example 135

N-(1-benzoyl-4-piperidinyl)-2-(3-dimethylamino-2,4,6-trimethylanilino)-N-methylacetamide (135)

The title compound (135) was obtained by the same manner as the Example 128 from the Compound (24) obtained in the Example 24 and benzoyl chloride.

Example 136

2-(2-Amino-4,5-dimethylanilino)-N-methyl-N-[1-(2-phenethyl)-4-piperidinyl]acetamide (136)

The title compound (136) was obtained by the same manner as the Example 28 from the Compound (25) obtained in the Example 25 and phenethyl bromide.

Example 137

2-(2-Amino-4,5-dimethylanilino)-N-methyl-N-[1-(trans-2-phenyl-1-cyclopropylmethyl)-4-piperidinyl]acetamide (137)

The title compound (137) was obtained by the same manner as the Example 28 from the Compound (25) obtained in the Example 25 and trans-2-phenyl-1-cyclopropylmethyl bromide.

Example 138

2-(4-Amino-2,5-dichloroanilino)-N-methyl-N-[1-(2-phenethyl)-4-piperidinyl]acetamide (138)

The title compound (138) was obtained by the same manner as the Example 28 from the Compound (26) obtained in the Example 26 and phenethyl bromide.

Example 139

2-(4-Amino-2,6-dichloroanilino)-N-[1-(2-anilino-2-oxyethyl)-4-piperidinyl]-N-methylacetamide (139)

A mixture solution of the compound obtained from the compound (27) in the Example 27 and N-phenyl-2-bromoacetamide by the same manner as the Example 28 and 5% platinum sulfided on carbon in methanol and tetrahydrofuran was stirred for 3.5 hours under 4 atm of hydrogen. Then, the catalyst was removed by Celite (trade name) filtration. The obtained residue was purified by amine-coated silica gel (Fuji Silysia Chemical Ltd.; NH-DM1020) column chromatography (methylene chloride:methanol=100:1) to give the above-mentioned compound (139) in 90% yield.

The physiochemical data of the compounds obtained by the above-mentioned examples are summarized in the following tables as Table I.

| No. | Chemical Structure | Properties m.p.(° C.) (solvent) | IR(CHCl₃) cm⁻¹ | ¹H-NMR(CDCl₃) |
|---|---|---|---|---|
| 1 | H₂N-(2,3,5-trimethylphenyl)-O-CH₂-C(O)-N(Me)-(piperidin-4-yl)NH | colorless cryst. (HCl salt) 191–193 (Et₂O/EtOH) | HCl salt: KBr 3424, 2940, 2805, 1642, 1489, 1418, 1321, 1298, 1284, 1140, 1100 | 1.46–1.80(4H, m), 2.10(3H, s), 2.15 & 2.16(3H, each s), 2.17 & 2.20(3H, each s), 2.59–2.78(2H, m), 2.87 & 2.93 (3H, each s), 3.09–3.18(2H, m), 3.34(2H, brs), 3.90 & 4.48–4.64(1H, m), 4.56 & 4.61(2H, each s), 6.55 & 6.60 (1H, each s) |
| 2 | H₂N-(2,3,5-trimethylphenyl)-O-CH(Me)-C(O)-N(Me)-(piperidin-4-yl)NH | oil substance | 3019, 2935, 1624, 1484, 1420, 1377, 1320, 1251, 1137, 1110, 1087, 1035, 846 | 1.54(3H, d), 1.58–1.64(4H, m), 2.10(3H, s), 2.12 & 2.13(3H, each s), 2.17(3H, s), 2.56(1H, m), 2.72(1H, m), 2.82 & 2.87(3H, each s), 3.05–3.13(2H, m), 3.33(2H, brs), 4.56 & 4.55(1H, m), 4.76–4.86(1H, m), 6.46 & 6.51 (1H, each s) |
| 3 | H₂N-(2,3,5-trimethylphenyl)-O-C(Me)₂-C(O)-N(Me)-(piperidin-4-yl)NH | foamy substance | 3374, 2939, 1612, 1483, 1383, 1364, 1319, 1257, 1157, 1086, 1019, 804 | 1.35–1.75(4H, m), 1.55 & 1.56(6H, s), 2.07, 2.09, 2.14 & 2.16(9H, each s), 2.50–2.60 & 2.70–2.82(2H, m), 2.85 & 3.13 (3H, each s), 3.00–3.20(2H, m), 3.20–3.45(2H, brs), 4.55–4.85(1H, m), 6.34 & 6.39(1H, each s) |
| 4 | H₂N-(2-NH₂-4,6-dimethylphenyl)-O-CH₂-C(O)-N(Me)-(piperidin-4-yl)NH | foamy substance | 1701, 1654, 1648, 1498, 1319, 1051, 929 | 1.43–1.84(4H, m), 2.18(3H, s), 2.23(3H, s), 2.56–2.83 (2H, m), 2.79 & 2.90(3H, each s), 3.05–3.21(2H, m), 3.39–3.52 & 4.47–4.64(1H, m), 4.06–4.39(2H, brs), 4.50 & 4.53(2H, each s), 6.33(1H, s), 6.39(1H, s) |

| | | | |
|---|---|---|---|
| 5 | 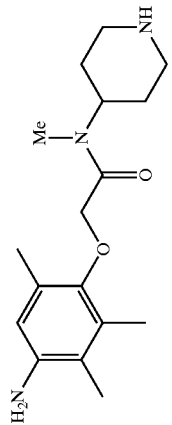 | foamy substance | 3394, 2953, 1654, 1484, 1417, 1320, 1225, 1090, 1052 | 1.60–1.91(4H, m), 2.04(3H, s), 2.17 & 2.20(6H, each s), 2.61–2.84(2H, m), 2.91(3H, s), 3.12–3.56(4H, m), 3.83 & 4.63(1H, m), 4.34 & 4.38(2H, each s), 6.25 & 6.39 (1H, each s) |
| 6 | 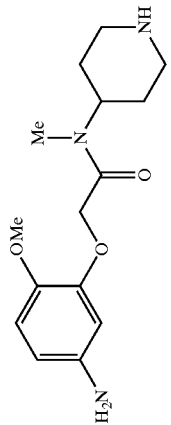 | oily substance | 3020, 1636, 1518, 1320, 1466, 1438, 1320, 1170, 1137, 1030, 929 | 1.59–1.74(4H, m), 2.67–2.75(2H, m), 2.84 & 2.95 (3H, each s), 3.10–3.13(2H, m), 3.45(2H, brs), 3.77 & 3.79(3H, each s), 4.02 & 4.52(1H, m), 4.70 & 4.73(2H, each s), 6.27(1H, m), 6.41(1H, m), 6.72(1H, m) |
| 7 | 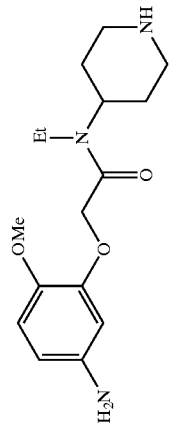 | oily substance | 3019, 1624, 1518, 1466, 1438, 1320, 1169, 1137, 1031, 929 | 1.13 & 1.22(3H, each t), 1.67–1.68(4H, m), 2.69–2.71(2H, m), 3.12(2H, m), 3.32 & 3.39(2H, each q), 3.35 & 3.97 (1H, m), 3.45(2H, brs), 3.77 & 3.79(3H, each s), 4.71(2H, s), 6.25–6.27(1H, m), 6.40 & 6.44(1H, m), 6.71(1H, m) |
| 8 | 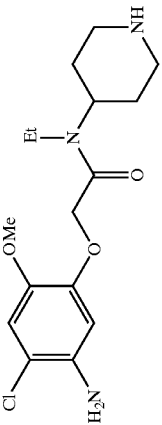 | oily substance | 3448, 1628, 1513, 1466, 1438, 1438, 1319, 1174, 1036, 929, 849 | 1.05 & 1.14(3H, each t), 1.55–1.68(4H, m), 2.56–2.75(2H, m), 3.05(2H, m), 3.20 & 3.28(2H, each q), 3.69 & 3.72 (3H, each s), 3.84 & 4.26(1H, m), 4.63(2H, s), 6.41 & 6.45(1H, each s), 6.71 & 6.73(1H, each s) |
| 9 | 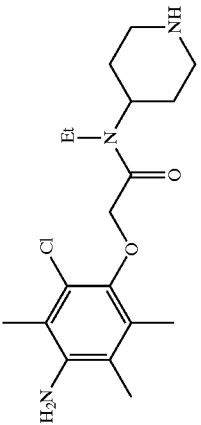 | colorless cryst. | 3020, 1629, 1466, 1436, 1380, 1320, 1087, 1037 | 1.21(3H, m), 1.68–1.78(4H, m), 2.08(3H, s), 2.24(3H, s), 2.27(3H, s), 2.72(2H, m), 3.15(2H, m), 3.42(2H, m), 3.55(2H, brs), 4.16–4.19(1H, m), 4.45(2H, s) |

| | | | |
|---|---|---|---|
| 10 | [structure] | foamy substance | 3413, 2952, 1638, 1466, 1420, 1320, 1089 | 1.37–1.79(4H, m), 2.12 & 2.14(6H, each s), 2.28(6H, s), 2.52–2.62 & 2.69–2.78(2H, m), 2.75 & 2.90(3H, each s), 3.08–3.18(2H, m), 3.34–3.53 & 4.61(3H, m), 3.58 & 3.63 (2H, each s) |
| 11 | [structure] | foamy substance | 3416, 2931, 1670, 1530, 1485, 1444, 1320, 1253, 1122 | 1.30–1.44(2H, m), 1.92–2.02(2H, m), 2.12(3H, s), 2.15(3H, s), 2.18(3H, s), 2.67–2.78(2H, m), 3.07 (2H, d), 3.39(2H, brs), 3.99(1H, m), 4.36(2H, s), 6.50(1H, s), 6.52–6.64(1H, brs) |
| 12 | [structure] | foamy substance | 3020, 2935, 1670, 1522, 1484, 1320, 1107 | 1.32–1.47(2H, m), 1.50(3H, d), 1.95(2H, m), 2.11(3H, s), 2.13(3H, s), 2.18(3H, s), 2.71–2.79 (2H, m), 3.10(2H, m), 3.39(2H, brs), 3.94(1H, m), 4.44(1H, q), 6.47(1H, s), 6.56(1H, brs) |
| 13 | [structure] | foamy substance | 3417, 2935, 1654, 1518, 1483, 1378, 1319, 1253, 1155, 1079, 1014, 954, 806 | 1.30–1.50(2H, m), 1.43(6H, s), 1.90–2.05(2H, m), 2.10(3H, s), 2.11(3H, s), 2.15(3H, s), 2.68–2.80 (2H, m), 3.05–3.15(2H, d, J=2.4Hz, 12.7Hz), 3.30–3.60(2H, brs), 3.85–4.00(1H, m), 6.56(1H, s), 6.90(1H, brs) |
| 14 | [structure] | foamy substance | 3448, 1654, 1636, 1466, 1438, 1320, 1117 | 1.10–1.29(3H, m), 1.44–1.78(4H, m), 2.10(3H, s), 2.16(3H, s), 2.17 & 2.21(3H, each s), 2.54–2.77(2H, m), 3.08–3.18(2H, m), 3.23–3.51(4H, m), 3.89 & 4.39 (1H, m), 4.57 & 4.58(2H, each s), 6.55 & 6.60(1H, each s) |

-continued

| # | Structure | Form | IR | NMR |
|---|---|---|---|---|
| 15 | (H2N-trimethylphenyl-O-CH(Me)-C(O)-N(Et)-piperidin-4-yl, NH) | foamy substance | 3448, 2937, 1624, 1466, 1433, 1376, 1319, 1247, 1152, 1110 | 1.07–1.11(3H, m), 1.52 & 1.55(3H, each d), 1.48–1.77 (4H, m), 2.09(3H, s), 2.11 & 2.12(3H, each s), 2.18(3H, s), 2.45–2.76(2H, m), 2.98–3.51(6H, m), 4.14 & 4.38 (1H, m), 4.71 & 4.80(1H, each q), 6.50 & 6.53(1H, each s) |
| 16 | (H2N-dimethyl-Cl-phenyl-O-CH2-C(O)-N(Me)-piperidin-4-yl, NH) | foamy substance | 3008, 2951, 1632, 1623, 1464, 1418, 1320, 1086, 1050, 1033 | 1.61–1.76(4H, m), 2.08(3H, s), 2.24(3H, s), 2.26 (3H, s), 2.73–2.78(2H, m), 2.91 & 2.99(3H, each s), 3.14–3.16(2H, m), 3.55(2H, brs), 4.18 & 4.59(1H, m), 4.46(2H, s) |
| 17 | (H2N-dimethyl-Cl-phenyl-O-CH2-C(O)-NH-piperidin-4-yl, NH) | colorless cryst. | 3408, 3018, 1668, 1623, 1534, 1417, 1320, 1108, 1089, 1045 | 1.45(2H, m), 1.99–2.03(2H, m), 2.08(3H, s), 2.20(3H, s), 2.24(3H, s), 2.74(2H, m), 3.10(2H, m), 3.58(2H, brs), 4.01(1H, m), 4.26(2H, s), 6.96(1H, brs) |
| 18 | (H2N-trimethylphenyl-NH-CH2-C(O)-N(Et)-piperidin-4-yl, NH) | foamy substance | 3374, 1637, 1420, 1382, 1256, 1098 | 1.12–1.26(3H, m), 1.55–1.82(4H, m), 2.12 & 2.14 (6H, each s), 2.29(6H, s), 2.47–2.79(2H, m), 3.08–3.24(2H, m), 3.19 & 3.37(2H, each q), 3.28–3.53 & 4.49(3H, m), 3.60 & 3.61(2H, each s) |
| 19 | (H2N-trimethylphenyl-N(Me)-CH2-C(O)-N(Me)-piperidin-4-yl, NH) | oily substance | 3224, 2944, 1632, 1472, 1412, 1371, 1328, 1159, 1100, 1059 | 1.55(4H, m), 2.09(6H, s), 2.26(6H, s), 2.35 & 2.72–2.76 (2H, m), 2.72(3H, s), 2.84(3H, s), 3.04–3.13(2H, m), 3.51(2H, brs), 3.76 & 3.79(2H, each s), 4.58(1H, m) |

| | Structure | Form | IR | NMR |
|---|---|---|---|---|
| 20 | H2N-(2,3,5,6-tetramethylphenyl)-NH-CH(Me)-C(=O)-N(Me)-(4-piperidyl) | oily substance | 3004, 2952, 1628, 1458, 1412, 1320, 1224, 1208, 1139, 1086 | 1.20 & 1.28(3H, each d), 1.41–1.84(4H, m), 2.09 & 2.10(3H, each s), 2.11(3H, s), 2.23(3H, s), 2.25(3H, s), 2.52 & 2.73(2H, m), 2.69 & 2.77(3H, each s), 3.12(2H, m), 3.32 & 4.56(1H, m), 3.40(2H, brs), 3.94(1H, m) |
| 21 | BocHN-(2,3,5,6-tetramethylphenyl)-NH-CH2-C(=O)-NH-(4-piperidyl) | foamy substance | 3020, 2400, 1718, 1664, 1522, 1482, 1368, 1319, 1227, 1205, 1162 | 1.33–1.46(2H, m), 1.51(9H, s), 1.92–2.05(2H, m), 2.18(6H, s), 2.20(6H, s), 2.74(2H, dt), 3.09(2H, m), 3.49(2H, s), 3.50(1H, brs), 3.97(1H, m), 5.86(1H, brs), 6.99(1H, d) |
| 22 | Me2N-(2,3,5,6-tetramethylphenyl)-NH-CH2-C(=O)-N(Me)-(4-piperidyl) | oily substance | 2924, 2779, 1640, 1450, 1407, 1370, 1329, 1285, 1064 | 1.50–1.80(4H, m), 2.19(6H, s), 2.24(6H, s), 2.60–2.90(2H, m), 2.76 & 2.80 (each s), 2.89(9H, each s), 3.10–3.20(2H, m), 3.38 & 4.58(1H, m), 3.67 & 3.71(2H, each s) |
| 23 | NH2-(2,3,5-trimethyl-...-phenyl)-NH-CH2-C(=O)-N(Me)-(4-piperidyl) | foamy substance | 3020, 2101, 1654, 1648, 1482, 1438, 1407, 1225, 1207 | 1.52–1.79(4H, m), 2.12(3H, s), 2.17 & 2.19(3H, each s), 2.24 & 2.25(3H, each s), 2.58 & 2.73(2H, m), 2.76 & 2.89 (3H, each s), 3.08–3.20(2H, m), 3.37 & 4.59(1H, m), 3.49(2H, brs), 3.69 & 3.73(2H, each s), 4.36–4.65(1H, brs), 6.74 & 6.75(1H, each s) |

| No. | Chemical Structure | Properties m.p.(° C.) (solvent) | IR(KBr): cm⁻¹ | ¹H-NMR(CDCl₃) |
|---|---|---|---|---|
| 24 | (structure: trimethylphenyl with NMe₂, N(Me)-CH₂-C(=O)-NH-piperidine) | foamy substance | 3020, 2952, 1648, 1478, 1448, 1370, 1320, 1225, 1207, 1091 | 1.53–1.81(4H, m), 2.21(3H, s), 2.27(3H, s), 2.28(3H, s), 2.61 & 2.69–2.87(2H, m), 2.77 & 2.80(3H, each s), 2.81 (6H, s), 3.14(2H, m), 3.39 & 4.60(1H, m), 3.71 & 3.76 (2H, each s), 4.40–4.76(1H, brs), 6.78 & 6.79(1H, each s) |
| 25 | (structure: dimethylphenyl with NH₂, N(Me)-CH₂-C(=O)-NH-piperidine) | foamy substance | 2944, 1641, 1582, 1408, 1288, 1243, 1154, 1107 | 1.63–1.81(4H, m), 2.13(3H, s), 2.17 & 2.18(3H, each s), 2.70–2.78(2H, m), 2.90 & 2.91(3H, each s), 3.16–3.22 (2H, m), 3.57 & 4.61(1H, m), 3.84 & 3.89(2H, each s), 6.43 & 6.44(1H, each s), 6.54(1H, s) |
| 26 | (structure: dichlorophenyl with H₂N, N(Me)-CH₂-C(=O)-NH-piperidine) | foamy substance | CHCl₃; free base 1654, 1648, 1522, 1508, 1458, 1420, 1225, 1206, 929 | 1.34–1.89(4H, m), 2.67–2.80(2H, m), 2.90 & 2.93(3H, each s), 3.09–3.27(2H, m), 3.54 & 4.60(1H, m), 3.63(2H, brs), 3.80 & 3.85(2H, each d), 5.25(1H, m), 6.51 & 6.52 (1H, each s), 6.82(1H, s) |
| 27 | (structure: dichlorophenyl with O₂N, N(Me)-CH₂-C(=O)-NH-piperidine) | foamy substance | CHCl₃; free base 3257, 2950, 2802, 2731, 1654, 1587, 1522, 1435, 1378, 1310, 1142, 1090 | 1.70–1.73(2H, m)1.78–1.88(2H, m), 2.72 & 2.81(2H, m), 2.90 & 2.96(3H, each s), 3.24–3.31(2H, m), 3.41–3.52 & 4.64(1H, m), 4.44–4.49(2H, m), 6.78(1H, m), 8.14(2H, s) |

| No. | Chemical Structure | Properties m.p.(° C.) (solvent) | IR(KBr): cm⁻¹ (HCl salt) | ¹H-NMR(CD₃OD): HCl salt |
|---|---|---|---|---|
| 28 | 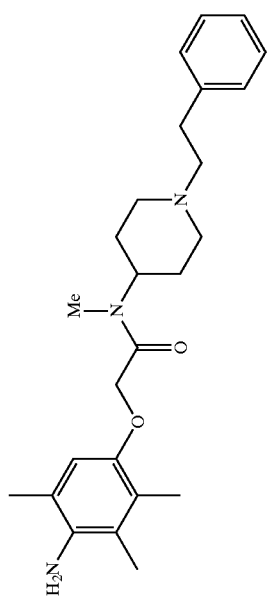 | colorless cryst. (HCl salt) 183–185 (EtOH/Et₂O) | (KBr: CDCl₃) 3366, 2938, 1647, 1538, 1489, 1456, 1418, 1310, 1283, 1134, 1101, 754, 703 | HCl salt (in CD₃OD) 1.88–2.09(2H, m), 2.16–2.42(2H, m), 2.23(3H, s), 2.30(3H, s), 2.37(3H, s), 2.89 & 3.02(3H, s), 3.07–3.23(4H, m), 3.26–3.41(2H, m), 3.67–3.84(2H, m), 4.21 & 4.60(1H, m), 4.86 & 4.96(2H, each s), 6.73 & 6.83(1H, each s), 7.23 & 7.41(5H, m) |
| 29 | 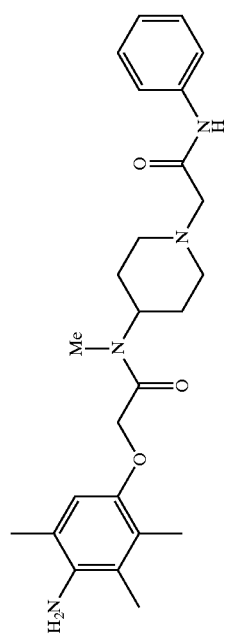 | colorless cryst. (HCl salt) 177–178 (EtOH/Et₂O) | (KBr: CDCl₃) 2938, 1694, 1636, 1558, 1490, 1448, 1315, 1132, 1102, 948, 761 | 1.66–2.02(4H, m), 2.11(3H, s), 2.17 & 2.20(6H, each s), 2.29–2.49(2H, m), 2.85–3.05(2H, m), 2.91 & 2.99(3H, each s), 3.14(2H, m), 3.36(2H, brs), 3.93 & 4.47(1H, m), 4.58 & 4.62(2H, each s), 6.55 & 6.59(1H, each s), 7.12(1H, m), 7.34(2H, m), 7.56(2H, d), 8.94&9.03(1H, brs) |
| 30 | 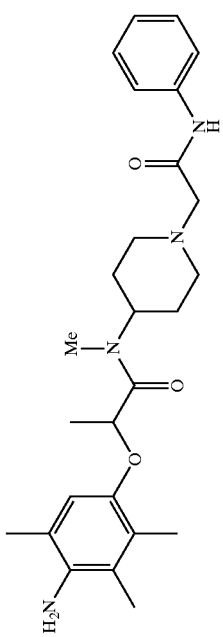 | colorless cryst. (HCl salt) 191–193 (EtOH/Et₂O) | 2938, 1694, 1624, 1600, 1557, 1490, 1448, 1315, 1113, 1074, 949, 760 | free base(in CDCl₃) 1.38–1.97(7H, m), 2.07–2.31 & 2.36–2.49(2H, m), 2.09 & 2.10(3H, each s), 2.13 & 2.14(3H, each s), 2.18(3H, s), 2.84–3.03(2H, m), 2.87 & 2.97(3H, each s), 3.10 & 3.13(2H, each s), 3.34(2H, brs), 4.19 & 4.48(1H, m), 4.76–4.87(1H, m), 6.46 & 6.51(1H, each s), 7.07–7.14(1H, m), 7.30–7.37(2H, m), 7.49–7.63(2H, m), 8.93 & 9.02(1H, brs) |

| | | | |
|---|---|---|---|
| 31 | 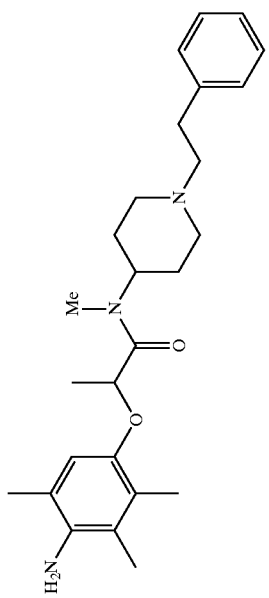 | colorless cryst. (HCl salt) 197–200 (MeOH/Et₂O) | 3416, 2936, 2690, 1664, 1486, 1461, 1283, 1113, 1093, 704 | 1.52–1.60(3H, m), 1.84–1.97(2H, m), 2.10–2.34(2H, m), 2.21(3H, s), 2.25(3H, s), 2.30(3H, s), 2.85 & 3.06 (3H, each s), 3.03–3.23(4H, m), 3.27–3.42(2H, m), 3.69–3.78(2H, m), 4.27–4.58(1H, m), 5.07–5.22(1H, m), 6.52 & 6.59(1H, each s), 7.25–7.33(5H, m) |
| 32 | 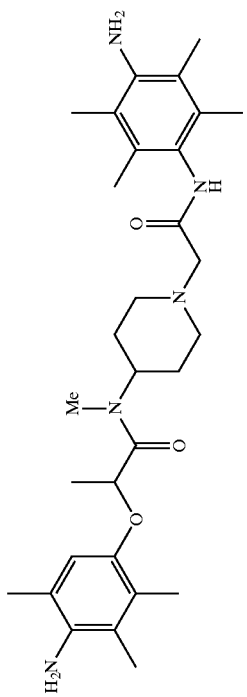 | colorless cryst. (HCl salt) 220–222 (MeOH/Et₂O) | 3442, 2937, 1634, 1538, 1486, 1456, 1284, 1112, 1034 | 1.53–1.63(3H, m), 1.82–1.94(2H, m), 2.16–2.39(2H, m), 2.21(6H, s), 2.22(3H, s), 2.30(3H, s), 2.31(6H, s), 2.36(3H, s), 2.86 & 3.08(3H, each s), 3.27–3.51(2H, m), 3.77(2H, m), 4.27–4.46 & 4.58(3H, m), 5.14–5.24 & 5.33–5.43(1H, m), 6.55 & 6.69(1H, each s) |
| 33 | 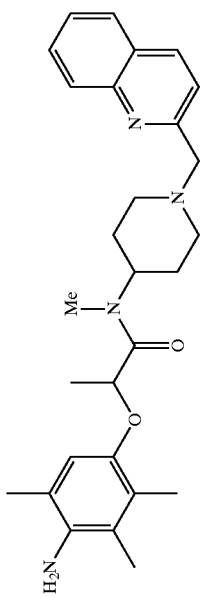 | colorless cryst. (HCl salt) 173–175 (MeOH/Et₂O) | 3398, 2936, 1642, 1486, 1417, 1390, 1309, 1286, 1215, 1113, 1034, 836 | 1.54–1.63(3H, m), 1.84–1.96(2H, m), 2.23, 2.30 & 2.36 (9H, each s), 2.26–2.47(2H, m), 2.91 & 3.12(3H, s), 3.27–3.46(2H, m), 3.77–3.88(2H, m), 4.44 & 4.61(1H, m), 4.73(1H, d), 5.17–5.38(1H, m), 6.56 & 6.66(1H, s), 7.57(1H, d), 7.67(1H, m), 7.84(1H, m), 7.99(1H, d), 8.14(1H, d), 8.44(1H, d) |
| 34 | 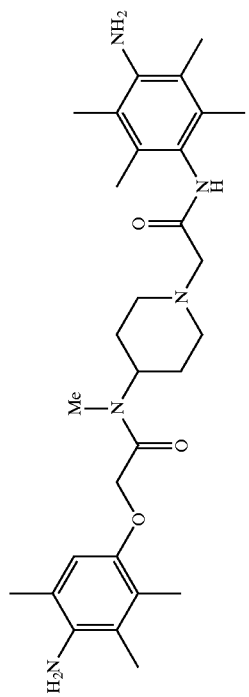 | colorless cryst. (HCl salt) 215–217 (MeOH/Et₂O) | 3415, 2936, 1642, 1531, 1487, 1461, 1284, 1133, 1104, 950 | 1.91–2.10(2H, m), 2.13–2.47(2H, m), 2.21(6H, s), 2.24(3H, s), 2.30(9H, s), 2.38(3H, s), 2.89 & 3.02 (3H, each s), 3.28–3.42(2H, m), 3.76(2H, m), 4.22 & 4.61 (1H, m), 4.27–4.40(2H, m), 4.86 & 4.98(2H, each s), 6.74 & 6.85(1H, each s) |

| | | | |
|---|---|---|---|
| 35 | 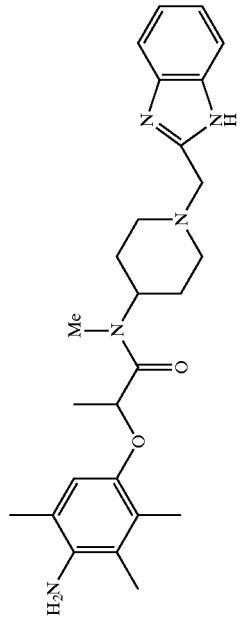 | pale yellow cryst. (HCl salt) 153–155 (EtOH/Et₂O) | 3443, 2937, 1626, 1486, 1456, 1324, 1288, 1215, 1114, 1023, 754 | 1.53–1.60(3H, m), 1.73–1.90(2H, m), 2.11–2.39(2H, m), 2.22(3H, s), 2.29(3H, s), 2.35(3H, s), 2.86 & 3.07(3H, each s), 2.90–3.15(2H, m), 3.45–3.54(2H, m), 4.18–4.27 & 4.42–4.58(1H, m), 4.45 & 4.52(2H, each s), 5.18 & 5.29(1H, each q), 6.53 & 6.65(1H, each s), 7.53–7.63(2H, m), 7.73–7.83(2H, m) |
| 36 | 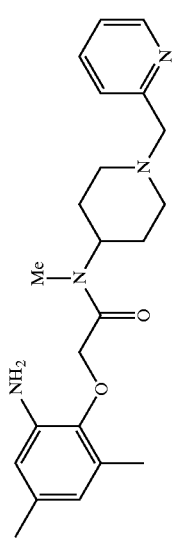 | colorless cryst. (HCl salt) 141–143 (MeOH/Et₂O) | 3441, 2972, 2731, 1670, 1613, 1476, 1409, 1217, 1045, 843, 765 | 2.02–2.24(2H, m), 2.15 & 2.16(3H, each s), 2.20 & 2.21 (3H, each s), 2.26–2.42(2H, m), 2.75 & 2.92(3H, each s), 3.24–3.37(2H, m), 3.46(1H, m), 3.60–3.79(2H, m), 4.51 & 4.52(2H, each s), 4.55(2H, s), 6.54(1H, s), 6.64(1H, s), 7.56(1H, dd), 7.67(1H, d), 8.02(1H, m), 8.73(1H, s) |
| 37 | 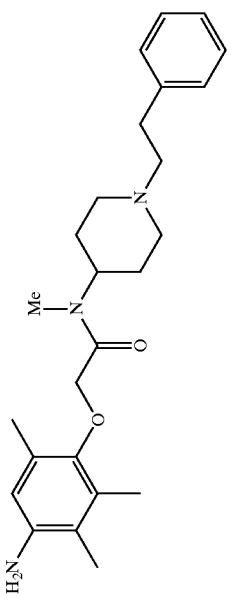 | colorless cryst. (HCl salt) 233–235 (MeOH/Et₂O) | 2924, 2616, 1651, 1481, 1331, 1307, 1226, 1098, 1046 | 1.94–2.09(2H, m), 2.16–2.35(2H, m), 2.20 & 2.23 (3H, s), 2.27(3H, s), 2.29(3H, s), 2.94(3H, s), 3.06–3.43 (6H, m), 3.68–3.83(2H, m), 4.54(2H, s), 4.64(1H, m), 7.00(1H, s), 7.22–7.39(5H, m) |
| 38 | 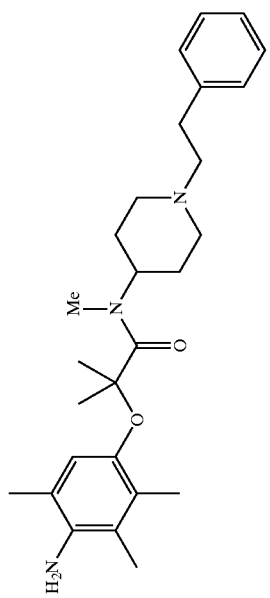 | colorless cryst. (HCl salt) 163–165 (MeOH/Et₂O) | 3422, 2940, 1622, 1482, 1410, 1386, 1317, 1155, 1091, 753, 703 | 1.63(6H, s), 1.81–1.92(2H, m), 2.11–2.36(2H, m), 2.20(3H, s), 2.29(3H, s), 2.30(3H, s), 2.88 & 3.10 (3H, each s), 2.98–3.24(4H, m), 3.27–3.38(2H, m), 3.60–3.80(2H, m), 4.61 & 4.87–4.98(1H, m), 6.45 & 6.49 (1H, each s), 7.22–7.39(5H, m) |

| No. | Chemical Structure | Properties m.p.(° C.) (solvent) | IR(KBr): cm⁻¹ (HCl salt) | ¹H-NMR(CDCl₃) |
|---|---|---|---|---|
| 39 | (structure: 4-amino-2,6-dimethylphenoxy linked via CH₂C(O)N(Me) to piperidine-N-CH₂C(O)NH-2,5-dichloro-4-aminophenyl) | colorless cryst. (HCl salt) 187–189 (MeOH/Et₂O) | 3356, 3194, 2934, 1691, 1634, 1533, 1486, 1397, 1304, 1224, 1096, 950, 880 | 1.87–2.09(2H, m), 2.17–2.38(2H, m), 2.25(3H, s), 2.28(3H, s), 2.30(3H, s), 2.94(3H, s), 3.22–3.42(2H, m), 3.72–3.87(2H, m), 4.14(2H, s), 4.56(2H, s), 4.67 (1H, m), 6.94(1H, s), 7.07(1H, s), 7.57(1H, s) |
| 40 | (structure: 4-amino-2,3,5,6-tetramethylphenyl-NH-C(O)CH₂-N(piperidine)-N(Me)-C(O)CH₂-N-phenethyl) | colorless cryst. (HCl salt) 173–175 (MeOH/Et₂O) | 3398, 2940, 2714, 1649, 1493, 1456, 1421, 1107, 1069, 951, 755, 704 | free base (in CDCl₃): 1.49–2.05(4H, m), 2.08–2.32(2H, m), 2.12(6H, s), 2.28(6H, s), 2.53–2.66(2H, m), 2.73–2.84 (2H, m), 2.75 & 2.90(3H, each s), 3.02–3.14(2H, m), 3.28–3.54(2H, brs), 3.34 & 4.56(1H, m), 3.59 & 3.62 (2H, each s), 7.16–7.23(3H, m), 7.24–7.32(2H, m) |
| 41 | (structure: 4-amino-2,3,5,6-tetramethylphenyl-NH-C(O)CH₂-piperidine-N(Me)-C(O)CH₂-NH-phenyl) | colorless cryst. (HCl salt) 172–174 (MeOH/Et₂O) | 3415, 2958, 1690, 1648, 1600, 1556, 1498, 1448, 1314, 1264, 950, 763 | free base (in CDCl₃) 1.48–1.98(4H, m), 2.12(6H, s), 2.28 (6H, s), 2.20–2.50(2H, m), 2.80 & 2.94(3H, each s), 3.00 (2H, m), 3.12 & 3.15(2H, each s), 3.33–3.54 & 4.56(1H, m), 3.60 & 3.63(2H, each s), 7.09–7.15(1H, m), 7.30–7.37(2H, m), 7.49–7.59(2H, m), 8.91 & 9.02(1H, brs) |
| 42 | (structure: 4-amino-2,3-dimethylphenoxy-C(Me)₂-C(O)-N(Me)-piperidine-N-CH₂C(O)NH-phenyl) | colorless cryst. (HCl salt) 178–180 (MeOH/Et₂O) | 2939, 2580, 1694, 1601, 1559, 1489, 1448, 1315, 1156, 1092, 952, 759 | 1.43–1.73(2H, m), 1.56(6H, s), 1.76–1.90(2H, m), 2.06 & 2.08(3H, each s), 2.09 & 2.10(3H, each s), 2.15 & 2.16 (3H, each s), 2.17–2.52(2H, m), 2.83–3.04(2H, m), 2.89 & 3.18 (3H, each s), 3.08 & 3.14(2H, each s), 3.34(2H, brs), 4.55 & 4.76(1H, m), 6.32 & 6.37(1H, each s), 7.11(1H, m), 7.33(2H, m), 7.55(2H, m), 8.95 & 9.04(1H, brs) |

| | | | |
|---|---|---|---|
| 43 | (structure: H₂N-dimethylphenyl-O-CH₂-C(O)-N(Me)-piperidine-N-CH₂-C(O)-NH-(2,5-dimethyl-4-hydroxyphenyl)) | colorless cryst. (HCl salt) 182–184 (MeOH/Et₂O) | 3422, 3210, 2950, 1643, 1520, 1489, 1464, 1414, 1132, 1104 | 1.46–1.97(4H, m), 2.11(3H, s), 2.15 & 2.16(3H, each s), 2.18(3H, s), 2.20(6H, s), 2.27–2.52(2H, m), 2.82–3.07(2H, m), 2.89 & 2.95(3H, each s), 3.16(2H, brs), 3.94 & 4.48(1H, m), 4.58 & 4.62(2H, each s), 6.54 & 6.59(1H, each s), 6.59(1H, s), 7.55(1H, s), 8.81 & 8.89(1H, brs) |
| 44 | (structure: quinoline-2-CH₂-piperidine-N(Me)-C(O)-CH₂-O-(H₂N-trimethylphenyl)) | pale yellow cryst. (HCl salt) 174–176 (MeOH/Et₂O) | 3406, 2934, 1642, 1600, 1487, 1540, 1645, 1581, 1417, 1390, 1304, 1214, 1131, 1099, 946, 842 | 1.53–1.70(2H, m), 1.76–2.02(2H, m), 2.07–2.36(2H, m), 2.10(3H, s), 2.14, 2.16 & 2.19(6H, each s), 2.88 & 2.94(3H, each s), 2.92–3.04(2H, m), 3.34(2H, brs), 3.83 & 3.84(2H, each s), 3.88 & 4.50(1H, m), 4.56 & 4.61(2H, each s), 6.54 & 6.59(1H, each s), 7.52(1H, m), 7.60(1H, d), 7.70(1H, m), 7.80(1H, d), 8.12(1H, d) |
| 45 | (structure with 3-Cl-2-Me-phenyl amide) | colorless cryst. (HCl salt) 178–180 (MeOH/Et₂O) | 3414, 2950, 1690, 1645, 1581, 1540, 1488, 1463, 1289, 1132, 1101, 1019, 950, 783 | 1.69–1.99(4H, m), 2.11(3H, s), 2.16 & 2.20(6H, each s), 2.30–2.56(2H, m), 2.36(3H, s), 2.89 & 2.97(3H, each s), 2.93–3.07(2H, m), 3.19(2H, s), 3.36(2H, brs), 3.96 & 4.50(1H, m), 4.58 & 4.62(2H, each s), 6.55 & 6.59(1H, each s), 7.12–7.23(2H, m), 7.99(1H, m), 9.21 & 9.31(1H, brs) |
| 46 | (structure with 2-t-Bu-phenyl amide) | colorless cryst. (HCl salt) 186–188 (MeOH/Et₂O) | 3416, 2964, 1684, 1646, 1534, 1488, 1292, 1131, 1101, 950, 765 | 1.47(9H, s), 1.65–2.00(4H, m), 2.11(3H, s), 2.15, 2.17 & 2.19(6H, each s), 2.39–2.61(2H, m), 2.85 & 2.93(3H, each s), 2.99–3.09(2H, m), 3.20(2H, s), 3.35(2H, brs), 3.95 & 4.51(1H, m), 4.57 & 4.62(2H, each s), 6.55 & 6.59(1H, each s), 7.11(1H, m), 7.20–7.28(1H, m), 7.39(1H, d), 7.97(1H, d), 9.35 & 9.42(1H, brs) |

| | | | |
|---|---|---|---|
| 47 | 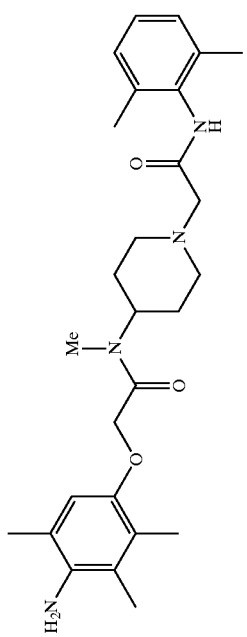 | colorless cryst. (HCl salt) 189–191 (MeOH/Et₂O) | 3417, 2950, 1648, 1540, 1477, 1416, 1286, 1240, 1131, 1101, 1034, 951, 778 | 1.67–1.98(4H, m), 2.11(3H, s), 2.16, 2.17 & 2.20(6H, each s), 2.24(6H, s), 2.36–2.54(2H, m), 2.87 & 2.95(3H, each s), 3.04–3.16(2H, m), 3.20(2H, s), 3.36(2H, brs), 3.95 & 4.50 (1H, m), 4.58 & 4.62(2H, each s), 6.55 & 6.60(1H, each s), 7.03–7.17(3H, m), 8.54 & 8.64(1H, brs) |
| 48 | 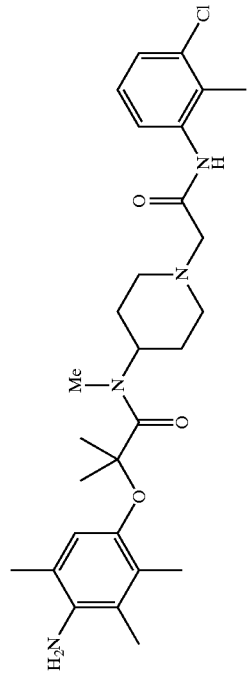 | colorless cryst. (HCl salt) 172–174 (MeOH/Et₂O) | 3402, 2944, 1695, 1616, 1582, 1540, 1464, 1404, 1292, 1156, 1092, 1016, 952, 782 | 1.47–1.87(4H, m), 1.56(6H, s), 2.07 & 2.08(3H, each s), 2.09 & 2.10(3H, each s), 2.15 & 2.16(3H, each s), 2.27–2.57(2H, m), 2.34(3H, s), 2.87 & 3.16(3H, each s), 2.84–3.07(2H, m), 3.13 & 3.19(2H, each s), 3.34(2H, brs), 4.60 & 4.79(1H, m), 6.32 & 6.37(1H, each s), 7.10–7.18(2H, m), 7.94–8.06(1H, m), 9.25 & 9.31(1H, brs) |
| 49 | 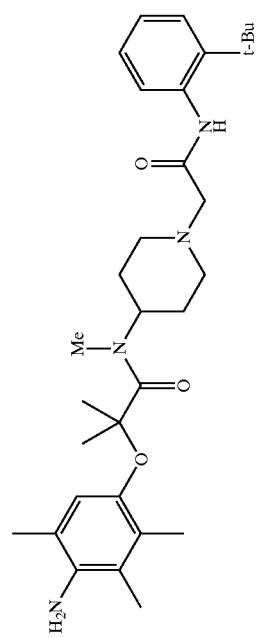 | colorless cryst. (HCl salt) 178–180 (MeOH/Et₂O) | 3384, 2968, 1684, 1624, 1534, 1483, 1404, 1157, 1089, 952, 764 | 1.38–1.73(2H, m), 1.45(9H, s), 1.55 & 1.56(6H, each s), 1.77–1.88(2H, m), 2.07 & 2.08(3H, s), 2.10(3H, s), 2.14 & 2.17 (3H, each s), 2.35 & 2.55(2H, m), 2.84 & 3.13(3H, each s), 2.90–3.09(2H, m), 3.14 & 3.20(2H, each s), 3.34(2H, brs), 4.36 & 4.78(1H, m), 6.32 & 6.36(1H, each s), 7.07–7.13 & 7.20–7.27(2H, m), 7.38(1H, d), 7.90–8.02(1H, m), 9.38 & 9.43(1H, brs) |
| 50 | 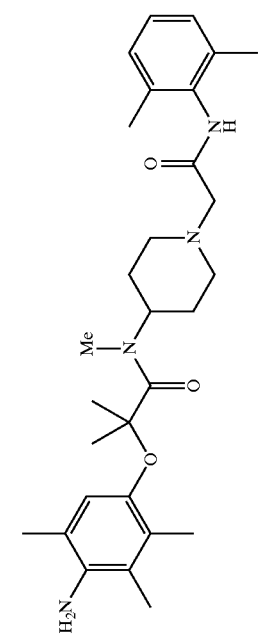 | colorless cryst. (HCl salt) 177–179 (MeOH/Et₂O) | 2939, 2604, 1690, 1637, 1540, 1474, 1401, 1157, 1091, 951, 775 | 1.47–1.89(4H, m), 1.55 & 1.57(6H, each s), 2.08 & 2.10 (6H, each s), 2.14 & 2.17(3H, each s), 2.21 & 2.23(6H, each s), 2.18–2.34(1H, m), 2.50(1H, m), 2.86 & 3.15(3H, each s), 2.94–3.17(2H, m), 3.15 & 3.21(2H, each s), 3.34(2H, brs), 4.58 & 4.79(1H, m), 6.33 & 6.37(1H, s), 7.05–7.15(3H, m), 8.56 & 8.63(1H, brs) |

| | | | |
|---|---|---|---|
| 51 | 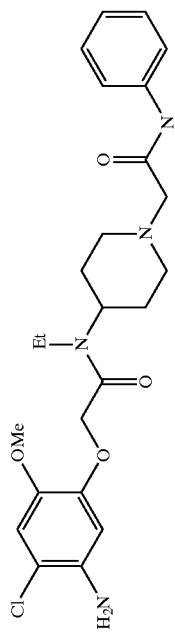 | colorless cryst. (HCl salt) 162–163 (iso-PrOH/ Et₂O) | 3418, 2975, 1690, 1646, 1556, 1511, 1447, 1404, 1354, 1267, 1178, 1072, 948 | 1.20 & 1.28(3H, t), 1.65–1.95(4H, m), 2.43(2H, m), 3.02(2H, m), 3.16(2H, s), 3.30–3.50(2H, m), 3.78 & 3.81 (3H, each s), 3.97(1H, m), 4.72(2H, s), 6.51 & 6.54(1H, each s), 6.81 & 6.83(1H, each s), 7.14(1H, t), 7.36(2H, m), 7.59(2H, m), 8.97 & 9.06(1H, brs) |
| 52 | 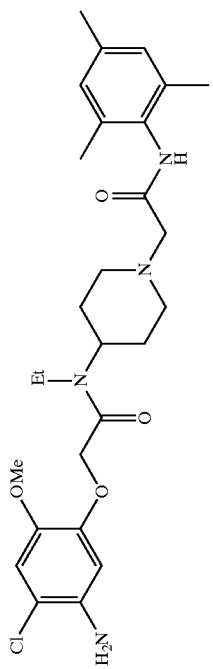 | colorless cryst. (HCl salt) 172–173 (iso-PrOH/ Et₂O) | 3416, 2970, 1684, 1646, 1511, 1403, 1270, 1219, 1180, 1074, 1035, 853 | 1.15 & 1.21(3H, each t), 1.71–1.92(4H, m), 2.21(6H, s), 2.29(3H, s), 2.45(2H, m), 3.08(2H, m), 3.21(2H, s), 3.30–3.50(2H, m), 3.78(1H, m), 3.79 & 3.80(3H, each s), 4.72(2H, brs), 6.51 & 6.55(1H, each s), 6.82(1H, s), 6.92(2H, s), 8.48 & 8.55(1H, brs) |
| 53 | 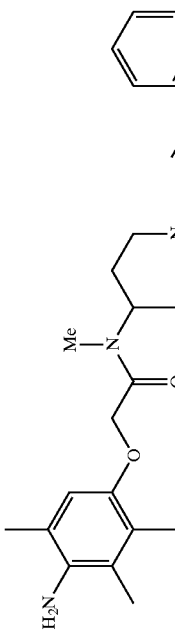 | colorless cryst. (HCl salt) 169–171 (MeOH/Et₂O) | 3383, 2938, 2714, 2592, 1646, 1489, 1456, 1418, 1325, 1285, 1134, 1104, 1031, 978, 942, 749 | 1.47–2.26(6H, m), 2.09 & 2.10(3H, each s), 2.15, 2.17 & 2.19(6H, each s), 2.87 & 2.93(3H, each s), 3.00–3.22(4H, m), 3.33(2H, brs), 3.84 & 4.49(1H, m), 4.56 & 4.60(2H, each s), 6.16–6.36(1H, m), 6.44–6.65(2H, m), 7.18–7.40(5H, m) |
| 54 | 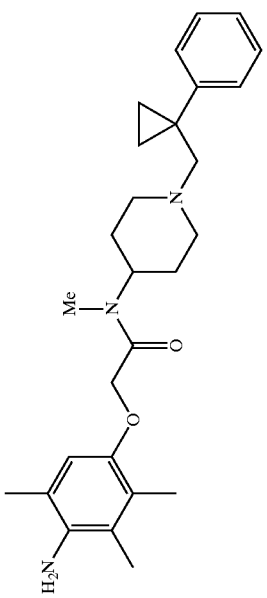 | colorless cryst. (HCl salt) 166–168 (MeOH/Et₂O) | 3416, 2939, 1647, 1489, 1458, 1417, 1323, 1303, 1287, 1244, 1134, 1098, 1030, 940, 704 | 0.64–0.77(2H, m), 0.79–0.94(2H, m), 1.44–1.82(4H, m), 1.92–2.23(2H, m), 2.09 & 2.10(3H, each s), 2.14, 2.15 & 2.18(6H, each s), 2.54 & 2.55(2H, each s), 2.80 & 2.86(3H, each s), 2.94–3.10(2H, m), 3.35(2H, brs), 3.72 & 4.38(1H, m), 4.54 & 4.57(2H, each s), 6.52 & 6.57(1H, each s), 7.17(1H, m), 7.23–7.37(4H, m) |

| | | | |
|---|---|---|---|
| 55 | 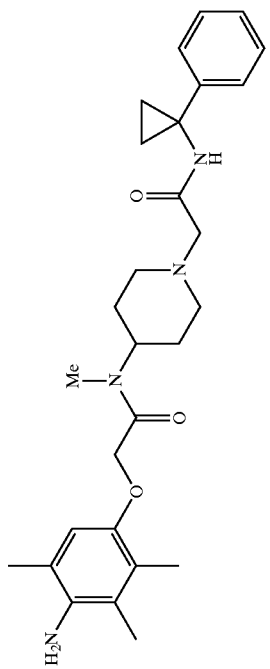 | colorless cryst. (HCl salt) 188–190 (MeOH/Et₂O) | 3416, 3214, 2950, 1684, 1646, 1544, 1489, 1457, 1418, 1323, 1303, 1285, 1132, 1102, 1030, 760, 700 | 1.23–1.33(4H, m), 1.47–1.93(4H, m), 2.10(3H, s), 2.15 & 2.19(6H, each s), 2.24(1H, m), 2.33(1H, m), 2.82–2.93 (2H, m), 2.88 & 2.95(3H, s), 2.99 & 3.00(2H, each s), 3.35(2H, brs), 3.87 & 4.42(1H, m), 4.57 & 4.60(2H, each s), 6.54 & 6.58(1H, each s), 7.15–7.33(5H, m), 7.62 & 7.68(1H, brs) |
| 56 | 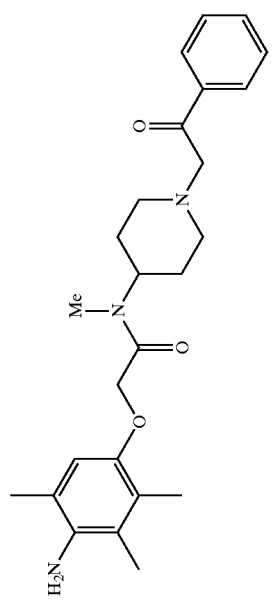 | colorless cryst. (HCl salt) 193–195 (MeOH/Et₂O) | 2942, 2860, 2593, 1694, 1642, 1597, 1488, 1451, 1306, 1260, 1230, 1132, 1102, 946 | 1.81–2.33(6H, m), 2.10(3H, s), 2.15, 2.17 & 2.20(6H, each s), 2.87 & 2.94(3H, each s), 3.03–3.13(2H, m), 3.81 & 3.83 (2H, each s), 3.87 & 4.51(1H, m), 4.57 & 4.61(2H, each s), 6.45 & 6.60(1H, each s), 7.46(2H, m), 7.57(1H, m), 7.98 (2H, m) |
| 57 | 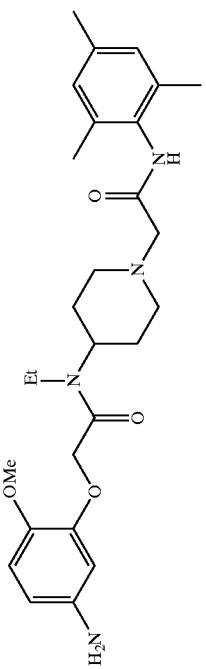 | colorless cryst. (HCl salt) 180–184 (iso-PrOH/Et₂O) | 1646, 1515, 1486, 1445, 1400, 1166, 1138, 1020 | 1.14 & 1.23(3H, each t), 1.74–1.98(4H, m), 2.19(6H, s), 2.27(3H, s), 2.43(2H, m), 3.07(2H, m), 3.18(2H, s), 3.31 & 3.40(2H, each q), 3.45(2H, brs), 3.78 & 3.79(3H, each s), 4.01 & 4.16(1H, m), 4.70 & 4.72(2H, each s), 6.27 & 6.29 (1H, m), 6.40 & 6.44(1H, m), 6.71 & 6.73(1H, each s), 6.90(2H, s), 8.47 & 8.54(1H, brs) |
| 58 | 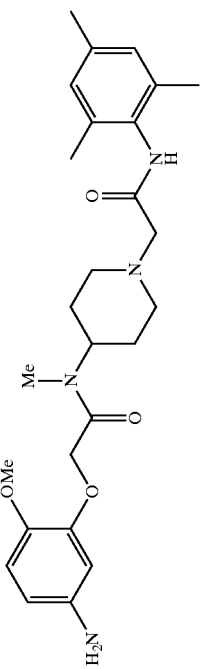 | brown cryst. (HCl salt) 226–228 (EtOH/MeCN) | 1645, 1515, 1446, 1350, 1296, 1166, 1139, 1061, 1023 | 1.67–1.92(4H, m), 2.18(6H, s), 2.27(3H, s), 2.45(2H, m), 2.85 & 2.97(3H, each s), 3.07(2H, m), 3.18(2H, s), 3.46(2H, brs), 3.78 & 3.79(3H, each s), 4.03 & 4.46(1H, m), 4.71 & 4.74(2H, s), 6.27 & 6.29(1H, each d), 6.39 & 6.42 (1H; each d), 6.72 & 6.74(1H, each s), 6.90(2H, s), 8.47 & 8.52(1H, brs) |

| | | | |
|---|---|---|---|
| 59 | 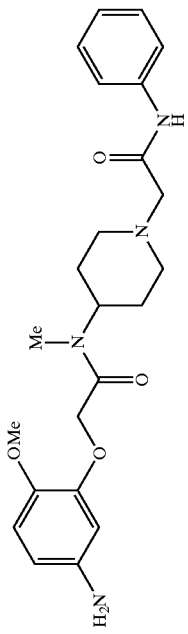 | colorless cryst. (HCl salt) 201–203 (EtOH/MeCN) | 1694, 1646, 1599, 1557, 1515, 1447, 1166, 1139, 1061, 1021 | 1.69(2H, m), 1.85(2H, m), 2.42(2H, m), 2.89 & 3.01 (3H, each s), 2.97–3.01(2H, m), 3.13(2H, s), 3.45((2H, brs), 3.76 & 3.80(3H, each s), 4.01 & 4.43(1H, m), 4.71 & 4.73 (2H, each s), 6.27 & 6.29(1H, m), 6.39 & 6.40(1H, m), 6.72(1H, m), 7.12(1H, d), 7.34(2H, t), 7.56(2H, d), 8.97 & 9.02(1H, brs) |
| 60 | 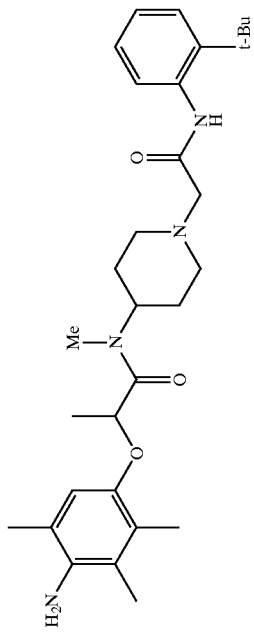 | colorless cryst. (HCl salt) 183–185 (MeOH/Et$_2$O) | 3411, 2963, 1687, 1638, 1534, 1486, 1415, 1291, 1113, 1090, 951, 764 | 1.38–1.97(7H, m), 1.46(9H, s), 2.10(3H, s), 2.12 & 2.14(3H, each s), 2.17 & 2.18(3H, each s), 2.36(1H, m), 2.47–2.57 (1H, m), 2.81 & 2.92(3H, each s), 3.02(2H, m), 3.16 & 3.19 (2H, each s), 3.34(2H, brs), 4.22 & 4.52(1H, m), 4.79 & 4.83(1H, each q), 6.46 & 6.51(1H, each s), 7.11(1H, m), 7.19–7.27(1H, m), 7.38(1H, dd), 7.97(1H, d), 9.33 & 9.41(1H, brs) |
| 61 | 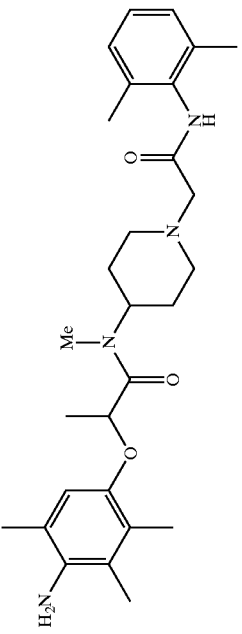 | colorless cryst. (HCl salt) 190–192 (MeOH/Et$_2$O) | 3424, 2942, 1688, 1634, 1538, 1478, 1416, 1286, 1240, 1113, 1074, 1035 | 1.41–1.98(7H, m), 2.10 & 2.11(3H, each s), 2.13 & 2.14(3H, each s), 2.17 & 2.18(3H, each s), 2.22 & 2.23(6H, each s), 2.25–2.53(2H, m), 2.83 & 2.93(3H, each s), 2.98–3.12(2H, m), 3.15–3.23(2H, m), 3.34(2H, brs), 4.23 & 4.50(1H, m), 4.80 & 4.83(1H, each q), 6.46 & 6.52(1H, each s), 7.05–7.15(3H, m), 8.48–8.67(1H, m) |
| 62 | 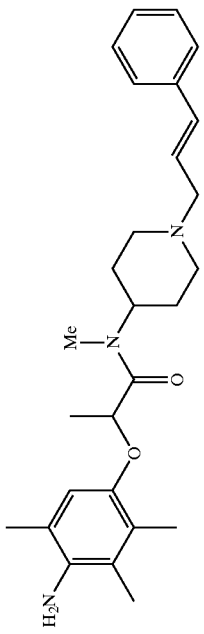 | pale yellow cryst. (HCl salt) 178–180 (MeOH/Et$_2$O) | 3410, 2937, 2712, 1638, 1487, 1452, 1413, 1323, 1283, 1244, 1215, 1113, 1075, 976, 749 | 1.25–2.03(6H, m), 1.54(3H, t), 2.09(3H, s), 2.12 & 2.13(3H, each s), 2.17 & 2.18(3H, each s), 2.82 & 2.92(3H, each s), 3.04(2H, m), 3.09–3.18(2H, m), 3.31(2H, brs), 4.11 & 4.50 (1H, m), 4.73–4.92(1H, m), 6.17–6.32(1H, m), 6.43–6.58 (2H, m), 7.22(1H, m), 7.30(2H, m), 7.37(2H, m) |

| | | | |
|---|---|---|---|
| 63 | 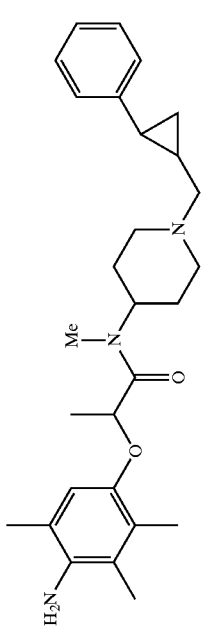 | colorless cryst. (HCl salt) 169–171 (MeOH/Et₂O) | 3411, 2937, 1648, 1605, 1486, 1460, 1417, 1323, 1285, 1243, 1115, 1032, 759, 700 | 0.75–0.86(1H, m), 0.91–1.02(1H, m), 1.15–1.27(1H, m), 1.32–2.22(7H, m), 1.54(3H, t), 2.09(3H, s), 2.12 & 2.13(3H, each s), 2.14 & 2.16(3H, each s), 2.26–2.57(2H, m), 2.81 & 2.90(3H, each s), 2.98–3.16(2H, m), 3.32(2H, brs), 4.10 & 4.47(1H, m), 4.79(1H, m), 6.45 & 6.50(1H, each s), 7.03 (2H, m), 7.14(1H, m), 7.20–7.29(2H, m) |
| 64 | 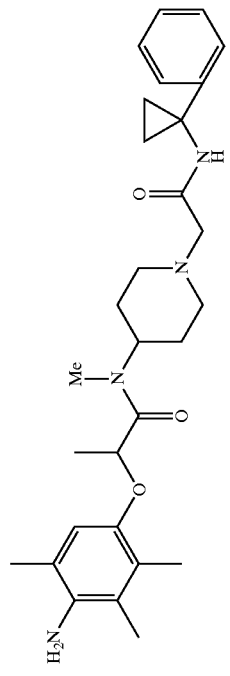 | colorless cryst. (HCl salt) 182–185 (MeOH/Et₂O) | 3411, 3203, 2940, 2590, 1688, 1638, 1545, 1486, 1458, 1416, 1322, 1284, 1110, 1030, 760, 700 | 1.19–1.33(4H, m), 1.47–1.90(7H, m), 2.07–2.38(2H, m), 2.10 (3H, s), 2.12 & 2.13(3H, each s), 2.16 & 2.17(3H, each s), 2.75–2.90(2H, m), 2.83 & 2.93(3H, each s), 2.94–3.03(2H, m), 3.34(2H, brs), 4.15 & 4.42(1H, m), 4.73–4.86(1H, m), 6.45 & 6.50(1H, each s), 7.15–7.32(5H, m), 7.59 & 7.67 (1H, brs) |
| 65 | 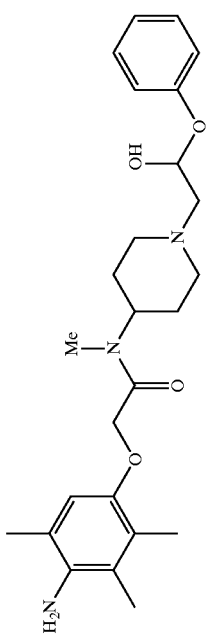 | colorless cryst. (HCl salt) 176–178 (MeOH/Et₂O) | 3368, 2932, 2874, 2573, 1647, 1598, 1492, 1459, 1417, 1293, 1244, 1137, 1109, 1038, 757 | 1.47–1.98(4H, m), 2.10(3H, s), 2.15, 2.16 & 2.20(6H, each s), 2.29–2.60(4H, m), 2.84–3.12(2H, m), 2.88 & 2.94 (3H, each s), 3.34(2H, brs), 3.88 & 4.49(1H, m), 3.98(2H, d), 4.02–4.12(1H, m), 4.57 & 4.61(2H, each s), 6.54 & 6.59 (1H, each s), 6.87–7.01(3H, m), 7.24–7.32(2H, m) |
| 66 | 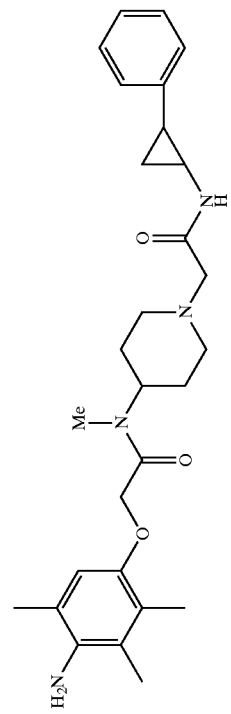 | colorless cryst. (HCl salt) 186–188 (MeOH/Et₂O) | 3392, 3214, 2590, 1672, 1556, 1487, 1461, 1415, 1286, 1131, 1103, 1031, 951, 700 | 1.15–1.23(2H, m), 1.25–1.32(1H, m), 1.50–1.93(4H, m), 2.06(1H, m), 2.10(3H, s), 2.15(3H, s), 2.19(3H, s), 2.24(1H, m), 2.33(1H, m), 2.81–3.06(2H, m), 2.88 & 2.96(3H, each s), 3.00(2H, s), 3.35(2H, brs), 3.88 & 4.42 (1H, m), 4.57 & 4.60(2H, each s), 6.54 & 6.58(1H, each s), 7.13–7.33(6H, m) |

| | | | |
|---|---|---|---|
| 67 | 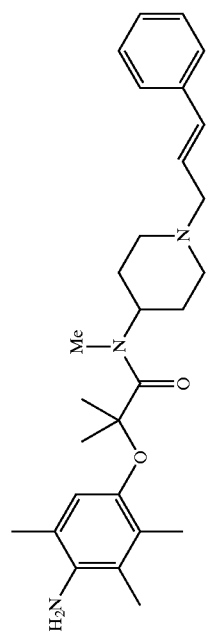 | colorless cryst. (HCl salt) 178–180 (MeOH/Et₂O) | 3982, 2939, 2586, 1618, 1482, 1410, 1156, 1096, 978, 950, 748 | 1.37–1.67(2H, m), 1.56(6H, s), 1.73–1.86(2H, m), 1.88–2.20(2H, m), 2.05 & 2.08(3H, s), 2.09(3H, s), 2.13 & 2.16(3H, each s), 2.85 & 3.13(3H, each s), 2.92–3.19(4H, m), 3.32(2H, brs), 4.59 & 4.70(1H, m), 6.17–6.35(1H, m), 6.33 & 6.38(1H, each s), 6.48 & 6.52(1H, each d), 7.22(1H, m), 7.30(2H, m), 7.36(2H, m) |
| 68 | 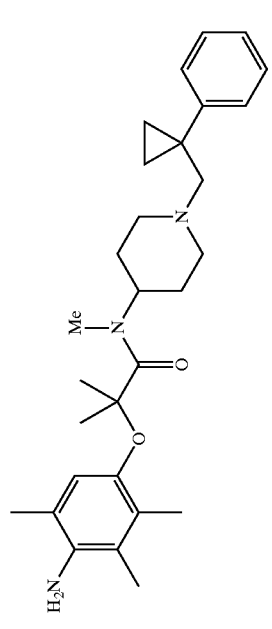 | colorless cryst. (HCl salt) 167–169 (iso-PrOH/Et₂O) | 3382, 2939, 2587, 1622, 1482, 1409, 1318, 1156, 1089, 1029, 763, 704 | (HCl salt in CD₃OD): 1.12(4H, m), 1.43–1.77(2H, m), 1.60(6H, s), 1.99–2.15(2H, m), 2.18 & 2.19(3H, each s), 2.28(6H, s), 2.79 & 3.01(3H, each s), 2.84–3.15(2H, m), 3.46–3.66(2H, m), 3.49(2H, s), 4.52 & 4.74–4.86(1H, m), 6.41 & 6.45(1H, each s), 7.30(1H, m), 7.39(2H, m), 7.44–7.57(2H, m) |
| 69 | 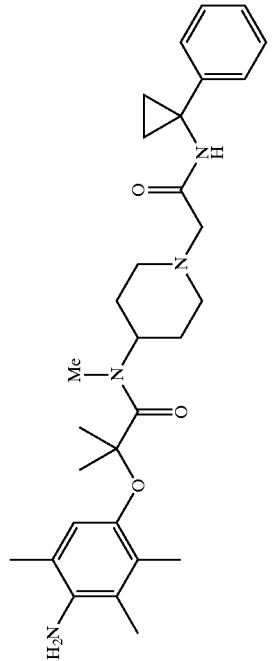 | colorless cryst. (HCl salt) 184–186 (MeOH/Et₂O) | 3416, 3194, 2946, 2590, 1688, 1630, 1548, 1482, 1460, 1403, 1321, 1156, 1092, 1029, 953, 759 | 1.19–1.32(4H, m), 1.37–1.84(10H, m), 2.03–2.20 & 2.34 (2H, m), 2.07(3H, s), 2.10(3H, s), 2.14(3H, s), 2.72–2.92 (2H, m), 2.86 & 2.95(2H, each s), 3.00 & 3.14(3H, each s), 3.34(2H, brs), 4.49 & 4.71(1H, m), 6.31 & 6.36(1H, each s), 7.15–7.32(5H, m), 7.61 & 7.68(1H, brs) |
| 70 | 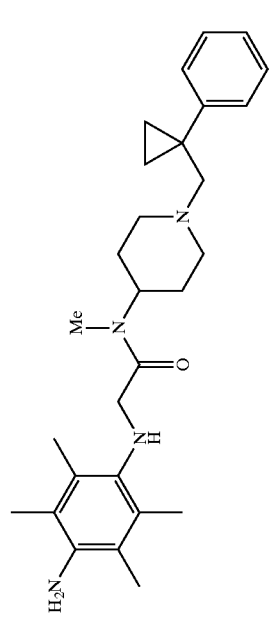 | colorless cryst. (HCl salt) 179–181 (MeOH/Et₂O) | 3381, 2947, 2731, 2568, 1649, 1582, 1496, 1450, 1417, 1104, 1065, 1030, 766, 704 | (HCl salt in CD₃OD): 1.09–1.19(4H, m), 1.79–1.96(2H, m), 2.07–2.20(2H, m), 2.29, 2.31, 2.35 & 2.37(12H, each s), 2.85 & 2.90(3H, each s), 3.01–3.25(2H, m), 3.50 & 3.51 (2H, each s), 3.55–3.68(2H, m), 3.93 & 4.57(1H, m), 4.21 & 4.44(2H, each s), 7.25–7.57(5H, m) |

| | | | |
|---|---|---|---|
| 71 | 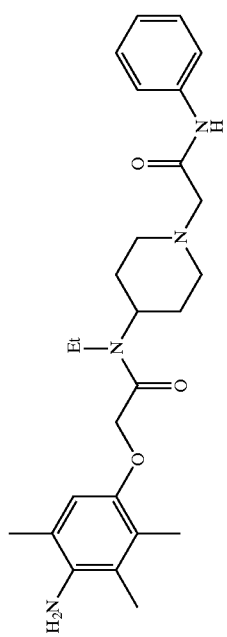 | colorless cryst. (HCl salt) 178–180 (MeOH/Et₂O) | 3416, 2968, 2596, 1693, 1629, 1600, 1556, 1490, 1448, 1316, 1236, 1131, 1111, 1032 | 1.16–1.30(3H, m), 1.76(2H, m), 1.82–2.08(2H, m), 2.10(3H, s), 2.16 & 2.21(6H, each s), 2.36(2H, m), 2.99 (2H, m), 3.13(2H, s), 3.25–3.51(4H, m), 3.92 & 4.15 (1H, m), 4.58 & 4.59(2H, each s), 6.55 & 6.60(1H, each s), 7.12(1H, t), 7.34(2H, t), 7.55(2H, t), 8.93 & 9.06(1H, brs) |
| 72 | 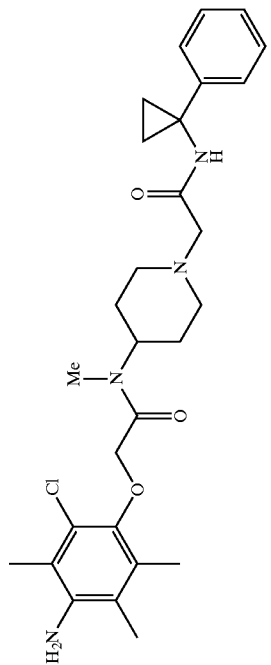 | colorless cryst. (HCl salt) 180–184 (EtOH/Et₂O) | 1687, 1638, 1546, 1498, 1456, 1417, 1320, 1304, 1100, 1031 | 1.28(4H, m), 1.70–1.92(4H, m), 2.07(3H, s), 2.24(3H, s), 2.25(3H, s), 2.34(2H, m), 2.89(2H, m), 2.92(2H, s), 3.01 & 3.02(3H, each s), 3.56(2H, brs), 4.20 & 4.50 (1H, m), 4.46(2H, s), 7.16–7.21(1H, m), 7.24–7.30 (4H, m), 7.66 & 7.70(1H, brs) |
| 73 | 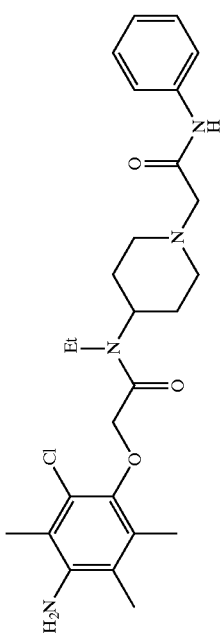 | colorless cryst. (HCl salt) 208–210 (EtOH/Et₂O) | 1692, 1634, 1556, 1500, 1448, 1411, 1317, 1106, 1050 | 1.25–1.27(3H, m), 1.82–2.03(4H, m), 2.08(3H, s), 2.25(3H, s), 2.26(3H, s), 2.43(2H, m), 3.01(2H, m), 3.15(2H, s), 3.41–3.45(2H, m), 3.56(2H, brs), 4.23 (1H, m), 4.45(2H, s), 7.12(1H, t), 7.34(2H, t), 7.58 (2H, d), 9.01 & 9.08(1H, brs) |
| 74 | 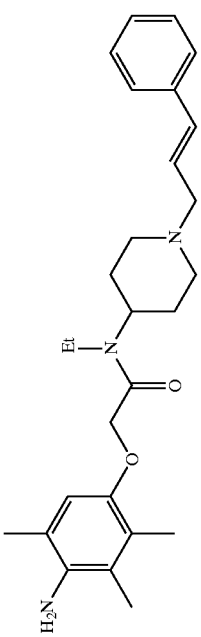 | colorless cryst. (HCl salt) 170–172 (MeOH/Et₂O) | 3406, 2938, 2596, 1650, 1485, 1460, 1324, 1284, 1215, 1133, 1111, 1033, 977, 945 | 1.15 & 1.20(3H, m), 1.66–2.24(6H, m), 2.10(3H, s), 2.15(3H, s), 2.17 & 2.20(3H, each s), 3.05(2H, m), 3.14 (2H, m), 3.25–3.43(4H, m), 3.42 & 3.83(1H, m), 4.58(2H, each s), 6.26(1H, m), 6.51(1H, m), 6.54 & 6.60 (1H, each s), 7.22(1H, t), 7.30(2H, t), 7.37(2H, d) |

| | | | |
|---|---|---|---|
| 75 | 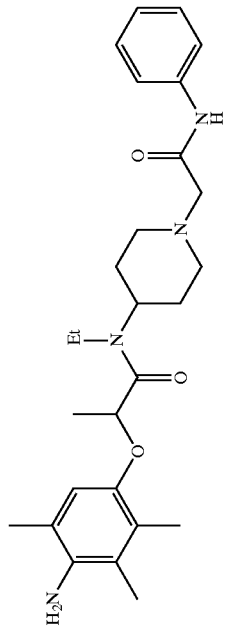 | colorless cryst. (HCl salt) 173–174 (MeOH/Et₂O) | 3405, 3193, 2974, 1695, 1623, 1556, 1489, 1448, 1315, 1259, 1215, 1109, 1030, 949 | 1.15 & 1.16(3H, each t), 1.37–1.94(7H, m), 1.95–2.44(2H, m), 2.09(3H, s), 2.13(3H, s), 2.17 & 2.18(3H, each s), 2.85–3.02(2H, m), 3.09 & 3.13(2H, each s), 3.20–3.52(4H, m), 4.05–4.24(1H, m), 4.73 & 4.80(1H, each q), 6.51 & 6.53 (1H, each s), 7.11(1H, brs), 7.33(2H, t), 7.55(2H, m), 8.91 & 9.07(1H, brs) |
| 76 | 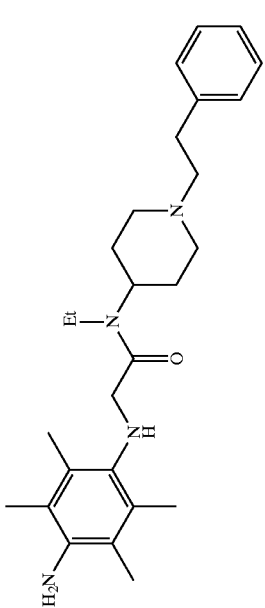 | colorless cryst. (HCl salt) 162–164 (MeOH/Et₂O) | 3402, 2945, 2736, 2558, 1643, 1584, 1460, 1384, 1290, 1112, 1072, 954, 754, 702 | 1.08–1.24(3H, m), 1.58–2.02(4H, m), 2.06–2.23(2H, m), 2.12 & 2.14(6H, each s), 2.29(6H, s), 2.53–2.67(2H, m), 2.78(2H, m), 3.07(2H, m), 3.20 & 3.38(2H, each q), 3.27–3.57 & 4.49(3H, m), 3.61(2H, s), 7.15–7.34(5H, m) |
| 77 | 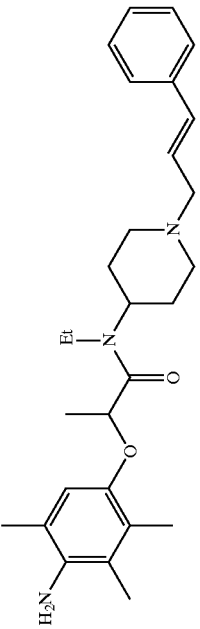 | pale yellow cryst. (HCl salt) 177–179 (MeOH/Et₂O) | 3410, 2937, 2592, 1642, 1485, 1460, 1431, 1377, 1323, 1285, 1215, 1132, 1112, 1028, 976, 946 | 1.05–1.16(3H, m), 1.33–2.26(6H, m), 1.52 & 1.55(3H, each d), 2.09(3H, s), 2.11 & 2.12(3H, s), 2.18(3H, s), 2.90–3.53 (6H, m), 3.11 & 3.15(2H, each d), 4.11 & 4.42(1H, m), 4.72 & 4.79(1H, each q), 6.25(1H, m), 6.43–6.62(2H, m), 7.23(1H, t), 7.27–7.40(4H, m) |
| 78 | 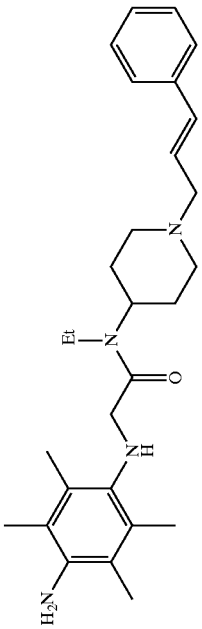 | colorless cryst. (HCl salt) 185–187 (MeOH/Et₂O) | 3406, 2939, 2710, 2555, 1646, 1580, 1450, 1384, 1278, 1211, 1113, 1072, 980, 946 | 1.16(3H, m), 1.45–2.20(6H, m), 2.12 & 2.14(6H, each s), 2.28(6H, s), 3.05(2H, m), 3.10–3.23(2H, m), 3.27–3.63 & 4.50(4H, m), 3.37 & 3.48(2H, each q), 3.61 (2H, s), 6.16–6.33(1H, m), 6.50 & 6.52(1H, each d), 7.22(1H, t), 7.31(2H, t), 7.37(2H, d) |

| | | | |
|---|---|---|---|
| 79 | 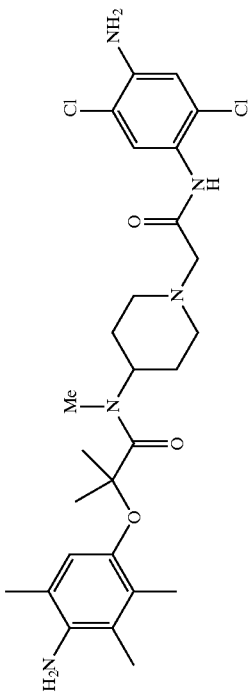 | colorless cryst. (HCl salt) | 3442, 2941, 1684, 1618, 1534, 1489, 1399, 1156, 1081 | 1.56(6H, s), 1.40–1.75(2H, m), 1.75–1.95(2H, m), 2.06, 2.08, 2.09, 2.10, 2.14 & 2.16(9H, each s), 2.28 & 2.49 (2H, m), 2.86 & 2.88(2H, each s), 2.95 & 3.15(3H, s), 2.95–3.15(2H, m), 3.20–3.45(2H, m), 3.85–4.10(2H, m), 4.61 & 4.76(1H, m), 6.32 & 6.37(1H, s), 6.79(1H, s), 8.35 & 8.36(1H, s), 9.59 & 9.64(1H, s) |
| 80 | 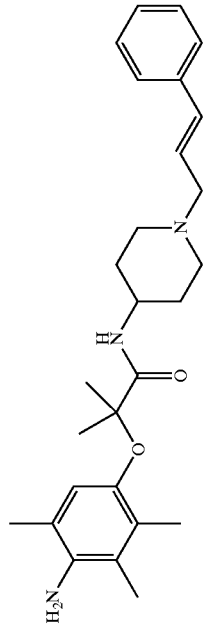 | colorless cryst. (HCl salt) | 3418, 2936, 2587, 1654, 1522, 1480, 1312, 1156, 1094, 945, 749, 695 | 1.42(6H, s), 1.45–1.70(2H, m), 1.95–2.10(2H, m), 2.09(3H, s), 2.11(3H, s), 2.14(3H, s), 2.15–2.30(2H, m), 2.85–2.95(2H, s), 3.15(2H, d), 3.42(2H, s), 3.87(1H, m), 6.26(1H, d), 6.51(1H, d), 6.56(1H, s), 6.91(1H, d), 7.22(1H, t), 7.30(2H, t), 7.37(2H, d) |
| 81 | 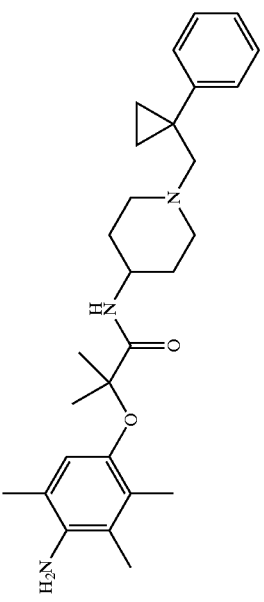 | pale yellow cryst. (HCl salt) 205–208 (MeOH/Et$_2$O) | 3418, 2932, 2580, 1668, 1532, 1482, 1157, 1107, 701 | 0.70–0.73(2H, m), 0.84–0.88(2H, m), 1.41(6H, s), 1.35–1.50(2H, m), 1.80–1.90(2H, m), 2.10(3H, s), 2.11(3H, s), 2.14(3H, s), 2.04–2.20(2H, m), 2.55(2H, s), 2.75–2.95(2H, m), 3.41(2H, brs), 3.79(1H, m), 6.54(1H, s), 6.83(1H, d), 7.16(1H, t), 7.25(2H, t), 7.32(2H, d) |
| 82 | 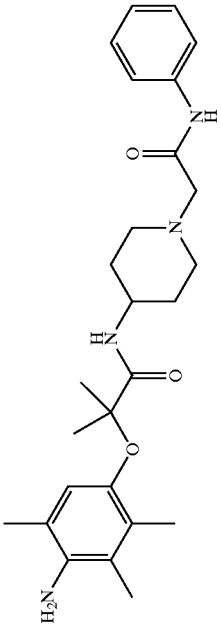 | colorless cryst. (HCl salt) | 3360, 2968, 2607, 1687, 1654, 1560, 1534, 1500, 1448, 1316, 1157, 1098, 950, 762, 692 | 1.44(6H, s), 1.45–1.70(2H, m), 2.00–2.25(2H, m), 2.11(3H, s), 2.12(3H, s), 2.17(3H, s), 2.40–2.55(2H, m), 2.80–3.05(2H, m), 3.13(2H, s), 3.35–3.55(2H, brs), 3.85–4.00(1H, m), 6.55(1H, s), 6.92(1H, d), 7.10 (1H, t), 7.33(2H, t), 7.55(2H, d) |

| | | | |
|---|---|---|---|
| 83 | 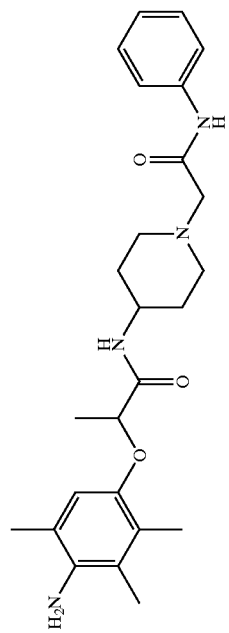 | colorless cryst. (HCl salt) 186–190 (EtOH/Et₂O) | 3424, 2936, 2495, 1684, 1601, 1556, 1500, 1448, 1316, 1148, 1116 | 1.45–1.63(2H, m), 1.51(3H, d), 2.00(2H, m), 2.13(3H, s), 2.14(3H, s), 2.21(3H, s), 2.44(2H, m), 2.83(2H, m), 3.11(2H, s), 3.41(2H, brs), 3.90(1H, m), 4.45(1H, q), 6.48(1H, s), 6.57 & 6.59(1H, brs), 7.10 (1H, t), 7.33(2H, t), 7.55(2H, d), 9.04(1H, brs) |
| 84 | 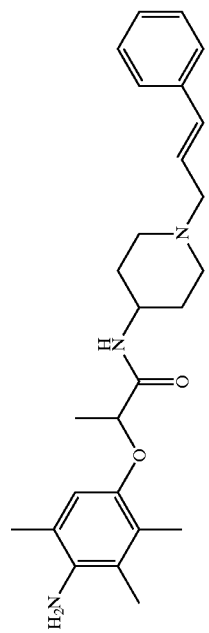 | pale yellow cryst. (HCl salt) 232–235 (EtOH/Et₂O) | 3424, 3193, 2938, 2806, 2594, 1680, 1590, 1552, 1486, 1153, 1118 | 1.41–1.51(2H, m), 1.50(3H, d), 1.94(2H, m), 2.06–2.23(2H, m), 2.11(3H, s), 2.13(3H, s), 2.18(3H, s), 2.85(2H, m), 3.13(2H, s), 3.38(2H, brs), 3.86(1H, m), 4.44(1H, q), 6.24(1H, dt), 6.48(1H, brs), 6.50(1H, d), 6.54(1H, d), 7.20–7.23(1H, m), 7.30(2H, t), 7.35–7.37 (2H, m) |
| 85 | 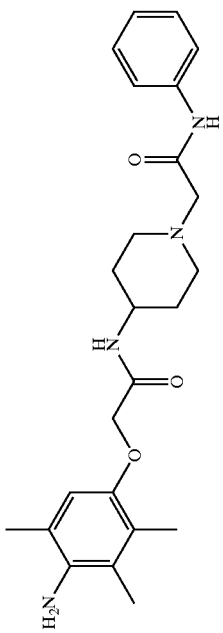 | colorless cryst. (HCl salt) 178–181 (MeOH/Et₂O) | 3402, 3247, 2946, 2592, 1688, 1600, 1556, 1491, 1448, 1315, 1128, 949 | 1.48–1.66(2H, m), 2.00–2.09(2H, m), 2.13(3H, s), 2.16(3H, s), 2.21(3H, s), 2.38–2.57(2H, m), 2.86(2H, m), 3.13(2H, s), 3.41(2H, brs), 3.97(1H, m), 4.38(2H, s), 6.50(1H, s), 6.60(1H, brs), 7.11(1H, t), 7.33(2H, m), 7.58(2H, d), 9.04(1H, brs) |
| 86 | 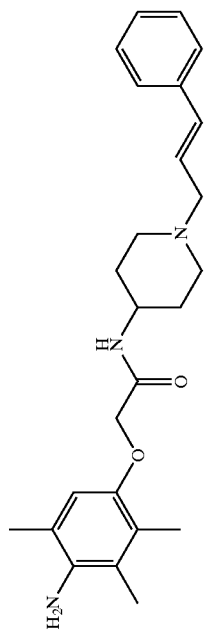 | pale yellow cryst. (HCl salt) 196–198 (MeOH/Et₂O) | 3326, 2934, 2518, 1662, 1547, 1486, 1451, 1326, 1285, 1238, 1214, 1130, 976, 942 | 1.46–1.75(2H, m), 1.94–2.03(2H, m), 2.09–2.25(2H, m), 2.11(3H, s), 2.15(3H, s), 2.17(3H, s), 2.78–2.99 (2H, m), 3.15(2H, d), 3.39(2H, brs), 3.93(1H, m), 4.36(2H, s), 6.26(1H, dt), 6.47–6.63(2H, m), 6.49 (1H, s), 7.22(1H, t), 7.30(2H, m), 7.37(2H, d) |

| | | | |
|---|---|---|---|
| 87 | 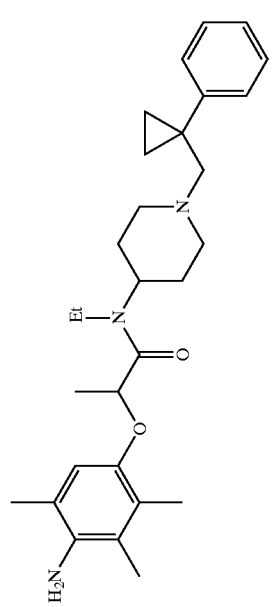 | colorless cryst. (HCl salt) 184–187 (MeOH/Et$_2$O) | 3404, 2936, 2579, 1642, 1485, 1461, 1432, 1376, 1322, 1286, 1245, 1215, 1112, 1027 | 0.64–0.74 & 0.81–0.90(4H, m), 1.06(3H, m), 1.19–1.28(1H, m), 1.44–1.77(2H, m), 1.50 & 1.52(3H, each d), 1.82–1.91(2H, m), 1.97–2.23(1H, m), 2.08 & 2.09(3H, each s), 2.10 & 2.11(3H, each s), 2.16(3H, s), 2.51 & 2.55(2H, each s), 2.87–3.05(2H, m), 3.09–3.55(4H, m), 3.98 & 4.29(1H, m), 4.69 & 4.76(1H, each q), 6.48 & 6.50(1H, each s), 7.13–7.20(1H, m), 7.22–7.38(4H, m) |
| 88 | 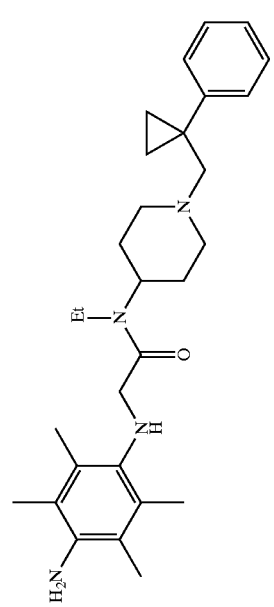 | colorless cryst. (HCl salt) 183–186 (MeOH/Et$_2$O) | 3403, 2944, 2728, 2563, 1646, 1581, 1460, 1432, 1296, 1113, 1069, 1028, 943 | 0.66–0.76 & 0.82–0.88(4H, m), 1.06–1.16(3H, m), 1.44–1.76, 1.81–1.92 & 1.97–2.30(6H, m), 2.12 & 2.14(6H, each s), 2.24 & 2.27(6H, each s), 2.52 & 2.56(2H, each s), 2.96–3.05(2H, m), 3.11 & 3.30(2H, each q), 3.24 & 4.37(1H, m), 3.34–3.65(2H, brs), 3.57(2H, s), 7.13–7.22(1H, m), 7.23–7.36(4H, m) |
| 89 | 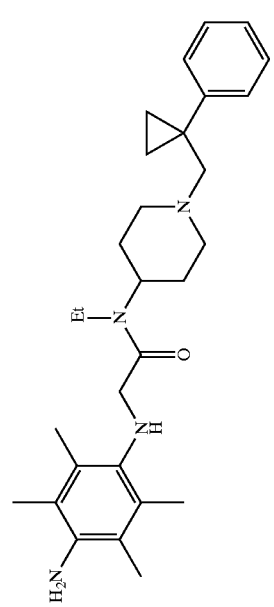 | colorless cryst. (HCl salt) 183–186 (MeOH/Et$_2$O) | 3402, 2944, 2591, 1692, 1640, 1530, 1486, 1385, 1302, 1285, 1132, 1100 | 1.65–1.77(2H, m), 1.78–1.90(1H, m), 1.90–2.03(1H, m), 2.10 (3H, s), 2.16 & 2.20(6H, each s), 2.33–2.55(2H, m), 2.88 & 2.95(3H, each s), 2.92–3.03(2H, m), 3.15 & 3.18(2H, each s), 3.36(2H, brs), 3.94 & 4.51(1H, m), 3.99(2H, brs), 4.58 & 4.61 (2H, each s), 6.55 & 6.59(1H, each s), 6.81(1H, s), 8.36 & 8.37(1H, each s), 9.56 & 9.64(1H, brs) |
| 90 | 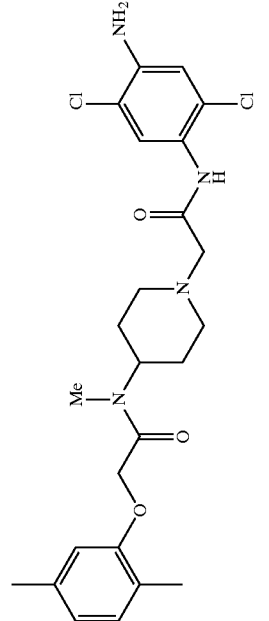 | colorless cryst. (HCl salt) 172–175 (iso-PrOH/Et$_2$O) | 3416, 2939, 2600, 1634, 1486, 1416, 1323, 1112, 1028, 763, 704 | 0.68–0.72 & 0.83–0.86(4H, m), 1.24–1.26 & 1.39–1.42 (2H, m), 1.51 & 1.53(3H, each d), 1.56–1.77(2H, m), 1.89 & 2.04(2H, m), 2.09(3H, s), 2.11 & 2.12(3H, each s), 2.15(3H, s), 2.52 & 2.55(2H, each s), 2.76 & 2.84(3H, each s), 2.97(2H, m), 3.31(2H, brs), 4.00 & 4.38(1H, m), 4.76 & 4.79(1H, each q), 6.43 & 6.49(1H, each s), 7.14–7.21(1H, m), 7.23–7.32(4H, m) |

| | Structure | Properties | NMR |
|---|---|---|---|
| 91 | (2,6-dimethyl-4-amino-3-chlorophenoxy)acetyl-[1-(phenylcarbamoylmethyl)piperidin-4-yl]amine | colorless cryst. (HCl salt) 221–224 (MeOH/Et₂O) | 3258, 1657, 1601, 1556, 1500, 1448, 1408, 1315, 1106, 953, 756, 694 | 1.69(2H, m), 2.09–2.10(2H, m), 2.22(3H, s), 2.25(3H, s), 2.49(2H, m), 2.91(2H, m), 3.15(2H, s), 3.59(2H, brs), 4.01(1H, m), 4.27(2H, s), 7.00(1H, brs), 7.11(1H, t), 7.34(2H, d), 7.57(2H, d), 9.09(1H, brs) |
| 92 | (2,6-dichloro-4-aminophenyl)...N-methyl | pale brown cryst. (HCl salt) 216–219 (EtOH/Et₂O) | 3424, 2948, 1692, 1634, 1534, 1497, 1456, 1398, 1319, 1304, 1101, 1049, 950 | 1.73–1.84(4H, m), 2.08(3H, s), 2.25(6H, s), 2.49(2H, m), 2.92 & 3.03(3H, each s), 2.99–3.03(2H, m), 3.16(2H, s), 3.55(2H, brs), 3.99(2H, brs), 4.27 & 4.55(1H, m), 4.47(2H, s), 6.81(1H, s), 8.38(1H, s), 9.63 & 9.66(1H, brs) |
| 93 | N-ethyl, 4-hydroxy | colorless cryst. (HCl salt) 193–197 (MeOH/Et₂O) | 3208, 2972, 1632, 1549, 1520, 1463, 1412, 1320, 1104, 952 | 1.24(3H, m), 1.85–2.03(4H, m), 2.07(3H, s), 2.21(6H, s), 2.25(3H, s), 2.26(3H, s), 2.45(2H, m), 3.03(2H, m), 3.16(2H, s), 3.39 & 3.44(2H, each s), 3.56(2H, brs), 4.25(1H, m), 4.46(2H, s), 4.70(1H, s), 6.62(1H, s), 7.61(1H, s), 8.88 & 8.95(1H, brs) |
| 94 | N-ethyl, phenylcyclopropylmethyl | colorless cryst. (HCl salt) 178–181 (MeOH/Et₂O) | 3402, 2944, 2726, 2554, 1643, 1464, 1426, 1391, 1290, 1073 | 0.77–0.86, 0.92–1.01 & 1.10–1.28(3H, m), 1.14 & 1.16(3H, each t), 1.42–2.02(5H, m), 2.04–2.42(3H, m), 2.12 & 2.14(6H, each s), 2.24 & 2.28(6H, each s), 2.50 & 2.53(1H, each dd), 3.04–3.16(2H, m), 3.18 & 3.36(2H, each q), 3.23–3.52(2H, brs), 3.29 & 4.46(1H, m), 3.60(2H, s), 7.01–7.07(2H, m), 7.14(1H, t), 7.20–7.29(2H, m) |

| | | | |
|---|---|---|---|
| 95 | 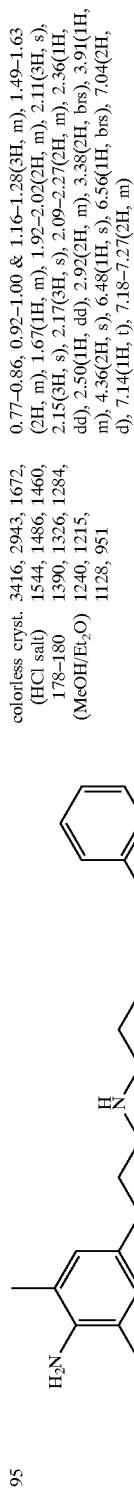 | colorless cryst. (HCl salt) 178–180 (MeOH/Et₂O) | 3416, 2943, 1672, 1544, 1486, 1460, 1390, 1326, 1284, 1240, 1215, 1128, 951 | 0.77–0.86, 0.92–1.00 & 1.16–1.28(3H, m), 1.49–1.63 (2H, m), 1.67(1H, m), 1.92–2.02(2H, m), 2.11(3H, s), 2.15(3H, s), 2.17(3H, s), 2.09–2.27(2H, m), 2.36(1H, dd), 2.50(1H, dd), 2.92(2H, m), 3.38(2H, brs), 3.91(1H, m), 4.36(2H, s), 6.48(1H, s), 6.56(1H, brs), 7.04(2H, d), 7.14(1H, t), 7.18–7.27(2H, m) |
| 96 | 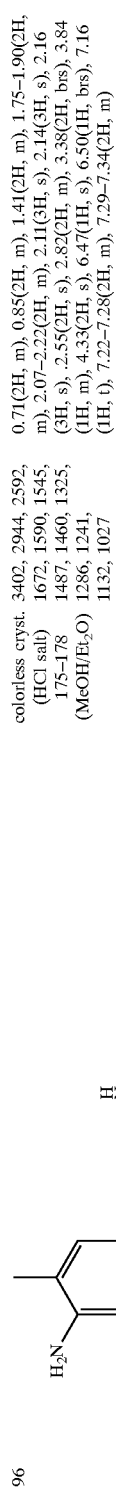 | colorless cryst. (HCl salt) 175–178 (MeOH/Et₂O) | 3402, 2944, 2592, 1672, 1590, 1545, 1487, 1460, 1325, 1286, 1241, 1132, 1027 | 0.71(2H, m), 0.85(2H, m), 1.41(2H, m), 1.75–1.90(2H, m), 2.07–2.22(2H, m), 2.11(3H, s), 2.14(3H, s), 2.16 (3H, s), 2.55(2H, s), 2.82(2H, m), 3.38(2H, brs), 3.84 (1H, m), 4.33(2H, s), 6.47(1H, s), 6.50(1H, brs), 7.16 (1H, t), 7.22–7.28(2H, m), 7.29–7.34(2H, m) |
| 97 | 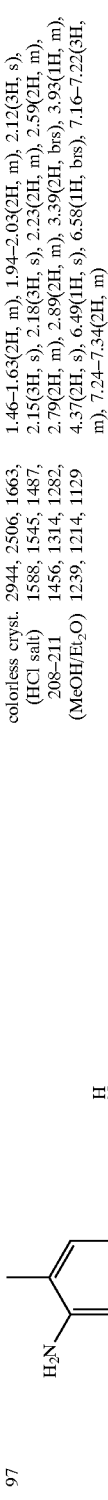 | colorless cryst. (HCl salt) 208–211 (MeOH/Et₂O) | 2944, 2506, 1663, 1588, 1545, 1487, 1456, 1314, 1282, 1239, 1214, 1129 | 1.46–1.63(2H, m), 1.94–2.03(2H, m), 2.12(3H, s), 2.15(3H, s), 2.18(3H, s), 2.23(2H, m), 2.59(2H, m), 2.79(2H, m), 2.89(2H, m), 3.39(2H, brs), 3.93(1H, m), 4.37(2H, s), 6.49(1H, s), 6.58(1H, brs), 7.16–7.22(3H, m), 7.24–7.34(2H, m) |
| 98 | 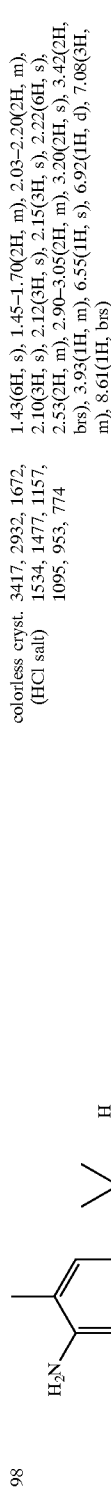 | colorless cryst. (HCl salt) | 3417, 2932, 1672, 1534, 1477, 1157, 1095, 953, 774 | 1.43(6H, s), 1.45–1.70(2H, m), 2.03–2.20(2H, m), 2.10(3H, s), 2.12(3H, s), 2.15(3H, s), 2.22(6H, s), 2.53(2H, s), 2.90–3.05(2H, m), 3.20(2H, s), 3.42(2H, brs), 3.93(1H, m), 6.55(1H, s), 6.92(1H, d), 7.08(3H, m), 8.61(1H, brs) |

| | | | |
|---|---|---|---|
| 99 | 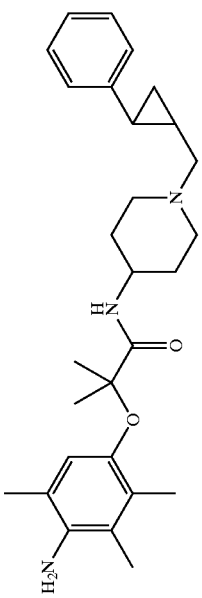 | colorless cryst. (HCl salt) | 3416, 2934, 2586, 1654, 1522, 1477, 1155, 1094, 700 | 0.78–0.85(1H, m), 0.93–0.98(1H, m), 1.18–1.28(1H, m), 1.41 (3H, s), 1.42(3H, s), 1.45–1.63(2H, m), 1.67(1H, m), 1.92–2.02(2H, m), 2.09(3H, s), 2.10(3H, s), 2.14(3H, s), 2.15–2.28(2H, m), 2.37(1H, dd), 2.50(1H, dd), 2.85–3.05(2H, m), 3.35–3.50(2H, brs), 3.84(1H, s), 6.56(1H, s), 6.89 (1H, d), 7.04(2H, d), 7.13(1H, t), 7.20–7.31(2H, m) |
| 100 | 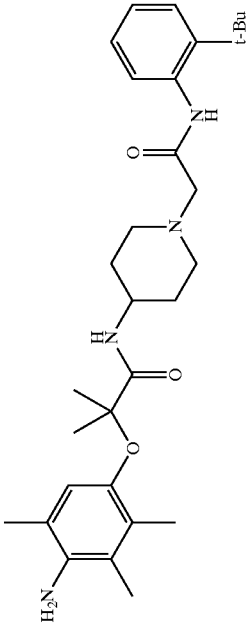 | colorless cryst. (HCl salt) | 3424, 2968, 1676, 1534, 1482, 1157, 1091, 953, 764 | 1.43 & 1.44(15H, each s), 1.45–1.65(2H, m), 1.95–2.10(2H, m), 2.10 & 2.12(6H, s), 2.16(3H, s), 2.45–2.65(2H, m), 2.85–3.00(2H, m), 3.19(2H, s), 3.35–3.50(2H, brs), 3.85–4.00(1H, m), 6.56(1H, s), 6.93(1H, d), 7.11(1H, t), 7.20–7.30(1H, m), 7.38(1H, d), 7.95(1H, d), 9.36(1H, brs) |
| 101 | 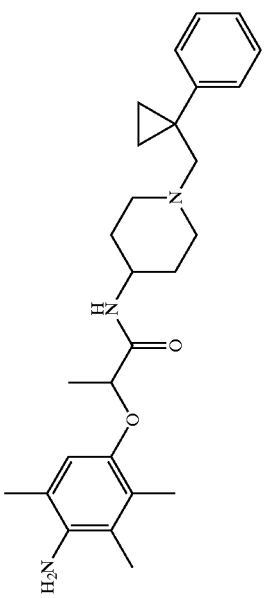 | colorless cryst. (HCl salt) 200–203 (EtOH/Et$_2$O) | 3419, 2942, 2580, 1691, 1666, 1592, 1487, 1459, 1428, 1152, 1118, 1040, 760, 701 | 0.70, 0.84 & 1.35(6H, m), 1.47(3H, d), 1.80(2H, m), 2.05–2.16(2H, m), 2.10(3H, s), 2.12(3H, s), 2.16(3H, s), 2.52(2H, s), 2.75–2.83(2H, m), 3.37(2H, brs), 3.76 (1H, m), 4.40(1H, q), 6.45(1H, s), 6.45–6.47(1H, brs), 7.17(1H, t), 7.22–7.26(2H, m), 7.30–7.32(2H, m) |
| 102 | 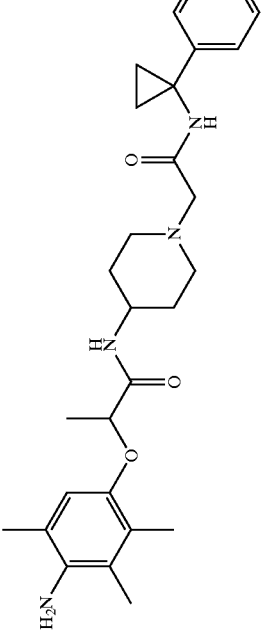 | colorless cryst. (HCl salt) 190–194 (EtOH/Et$_2$O) | 3418, 1684, 1541, 1498, 1486, 1460, 1324, 1149, 1116, 1030, 956 | 1.21–1.30(4H, m), 1.41–1.55(2H, m), 1.50(3H, d), 1.94(2H, m), 2.12(3H, s), 2.14(3H, s), 2.19(3H, s), 2.33(2H, m), 2.65–2.73(2H, m), 2.97(2H, s), 3.40(2H, brs), 3.85(1H, m), 4.43(1H, q), 6.46(1H, s), 6.53 (1H, brs), 7.18–7.31(5H, m), 7.67(1H, brs) |

| # | Structure | Form / mp / solvent | IR | NMR |
|---|---|---|---|---|
| 103 | (structure) | colorless cryst. (HCl salt) 143–147 (iso-PrOH/Et₂O) | 2938, 1634, 1599, 1492, 1417, 1114, 1040, 759, 694 | 1.54(3H, d), 1.56–1.88(4H, m), 2.10(3H, s), 2.13 & 2.14 (3H, each s), 2.17(3H, s), 2.24(2H, m), 2.53(2H, m), 2.83 & 2.92(3H, each s), 3.06(2H, m), 3.34(2H, brs), 3.97(2H, d), 4.03–4.06(1H, m), 4.15 & 4.47–4.53(1H, m), 4.77–4.85 (1H, m), 6.45 & 6.51(1H, each s), 6.91–6.97(3H, m), 7.26–7.31(2H, m) |
| 104 | (structure) | colorless cryst. (HCl salt) 180–183 (MeOH/Et₂O) | 3402, 3217, 2945, 1680, 1540, 1487, 1458, 1324, 1283, 1127, 1030, 956 | 1.25, 1.28, 1.46–1.64 & 1.93–2.03(8H, m), 2.12(3H, s), 2.15(3H, s), 2.19(3H, s), 2.36(2H, m), 2.73(2H, m), 2.99(2H, s), 3.40(2H, m), 3.92(1H, m), 4.36(2H, s), 6.49(1H, s), 6.57(1H, brs), 7.14–7.22(1H, m), 7.23–7.32(4H, m), 7.69(1H, brs) |
| 105 | (structure) | colorless cryst. (HCl salt) 178–180 (MeOH/Et₂O) | 3417, 2944, 2592, 1664, 1595, 1496, 1418, 1371, 1321, 1285, 1142, 1129, 1103, 1033 | 1.46–1.62(2H, m), 1.70–1.95(2H, m), 2.01–2.22(2H, m), 2.09(3H, s), 2.14(3H, s), 2.18(3H, s), 2.76–3.01(2H, m), 2.83 & 2.90(3H, each s), 2.92(2H, s), 3.27(3H, s), 3.33 (2H, brs), 3.74 & 4.39(1H, m), 4.54 & 4.56(2H, each s), 6.52 & 6.56(1H, each s), 7.19(2H, t), 7.29–7.37(1H, m), 7.41(2H, t) |
| 106 | (structure) | colorless cryst. (HCl salt) 173–176 (iso-PrOH/Et₂O) | 3423, 1664, 1605, 1544, 1485, 1462, 1386, 1324, 1116, 1034, 953 | 0.81, 0.95 & 1.20(3H, m), 1.50(3H, d), 1.58(2H, m), 1.66(1H, m), 1.92(2H, m), 2.11(3H, s), 2.12 & 2.13(3H, s), 2.17(3H, s), 2.19(3H, s), 2.33–2.37(1H, m), 2.46–2.51 (1H, m), 2.90(2H, m), 3.38(2H, brs), 3.83(1H, m), 4.44 (1H, q), 6.47(1H, s), 6.52(1H, m), 7.03(2H, d), 7.13 (1H, t), 7.21–7.26(2H, m) |

| No. | Chemical Structure | Properties m.p.(° C.) (solvent) | IR(KBr): cm$^{-1}$ (HCl salt) | $^1$H-NMR(DMSO-d$_6$): HCl salt |
|---|---|---|---|---|
| 107 | (structure: 4-amino-2,5-dimethylphenyl bonded via O-C(Me)$_2$-C(O)-N(Me) to piperidine, piperidine-CH$_2$-C(O)-NH-phenyl-4-OH with 2,5-dimethyl) | colorless cryst. (HCl salt) | 3426, 2943, 1684, 1619, 1552, 1518, 1466, 1411, 1157, 1089, 872 | 1.40–1.88(4H, m), 1.56 & 1.57(6H, each s), 2.00–2.32(1H, m), 2.07, 2.08, 2.10, 2.15 & 2.17(15H, each s), 2.47(1H, t), 2.86 & 3.14(3H, each s), 2.85–3.10(2H, m), 3.10 & 3.16(2H, each s), 3.34(2H, brs), 4.57 & 4.77(1H, m), 5.35(1H, brs), 6.32 & 6.37(1H, each s), 6.55(1H, s), 7.48 & 7.50(1H, each s), 8.85(1H, brs) |
| 108 | (structure: 4-amino-2,3,6-trimethylphenyl-O-CH$_2$-C(O)-NH-piperidine-CH$_2$-C(O)-N(Me)-phenyl) | colorless cryst. 176–178 (MeOH/Et$_2$O) (HCl salt) | 3417, 2934, 1668, 1595, 1544, 1496, 1454, 1372, 1285, 1240, 1129, 961 | 1.45–1.65(2H, m), 1.84–1.93(2H, m), 2.08–2.23(2H, m), 2.11(3H, s), 2.15(3H, s), 2.16(3H, s), 2.77(2H, m), 2.92(2H, s), 3.27(3H, s), 3.39(2H, brs), 3.85(1H, m), 4.34(2H, s), 6.48(1H, s), 6.53(1H, brs), 7.19(2H, d), 7.30–7.37(1H, m), 7.41(2H, m) |
| 109 | (structure: 4-amino-2,3,5,6-tetramethylphenyl-NH-CH$_2$-C(O)-N(Me)-piperidine-CH$_2$-CH(COOH)-phenyl) | foamy substance (HCl salt) | 2565, 1720, 1650, 1498, 1456, 1422, 1396, 1201, 1007, 949, 799 | HCl salt in DMSO-d$_6$ & CDCl$_3$: 1.78(2H, m), 2.08–2.44(2H, m), 2.14(6H, s), 2.28(6H, s), 2.77–3.04(2H, m), 2.81 & 2.90 (3H, each s), 3.25(1H, dd), 3.44–3.69(2H, m), 3.77–3.90 (1H, m), 3.82(2H, s), 4.26(1H, dd), 4.72(1H, m), 7.32 (5H, m) |
| 110 | (structure: 4-amino-2,3,5,6-tetramethylphenyl-NH-CH$_2$-C(O)-N(Me)-piperidine-N-CH$_2$-phenyl) | white amorphous (HCl salt) | 1646, 1497, 1456, 1418, 1309, 1118, 1005, 945, 752, 704 | 1.67 & 1.78(2H, d), 2.10–2.50(16H, m), 2.77 & 2.80 (3H, each s), 2.96(1H, m), 3.06(1H, m), 3.34(2H, m), 3.79 & 4.57(1H, m), 3.98 & 4.13(2H, each s), 4.26(2H, m), 7.45(3H, m), 7.65(2H, m), 11.4 & 11.5(1H, s) |

| | | | |
|---|---|---|---|
| 111 | 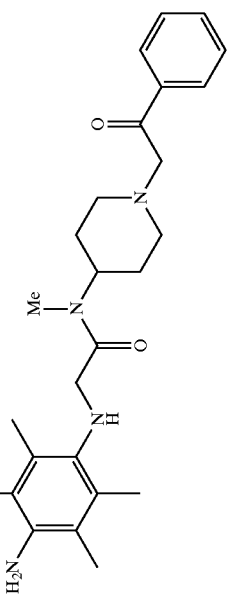 | pale yellow powder (HCl salt) 218–220 (EtOH/Et₂O) | 3426, 2940, 1692, 1651, 1597, 1450, 1392, 1307, 1263, 1233, 1153, 1109 | 1.75 & 1.83(2H, m), 2.20(6H, s), 2.24(6H, s), 2.20–2.32 (2H, m), 2.81 & 2.84(3H, each s), 3.27–3.43(2H, m), 3.60(2H, m), 3.93 & 4.51(2H, m), 4.60(1H, m), 5.03 & 5.07(2H, each s), 7.63(2H, m), 8.00(2H, m) |
| 112 | 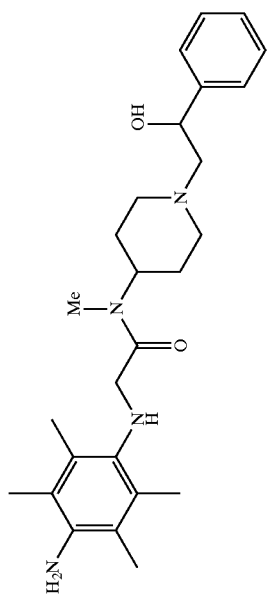 | white cryst. (HCl salt) 188–190 (MeOH/Et₂O) | 3418, 2947, 1650, 1500, 1454, 1415, 1312, 1201, 1153, 1106, 1069, 1029 | 1.71 & 1.83(2H, m), 2.18(6H, s), 2.22(6H, s), 2.18–2.23 (2H, m), 2.79 & 2.81(3H, each s), 3.09–3,19(4H, m), 3.72(2H, m), 3.90 & 4.08(2H, each s), 4.59(1H, m), 5.18(1H, m), 7.32–7.43(5H, m) |
| 113 | 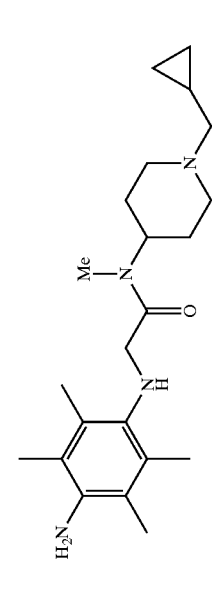 | white amorphous (HCl salt) | 3418, 2948, 1647, 1458, 1420, 1311, 1280, 1202, 1100, 1064, 1031, 950 | 0.40(2H, m), 0.63(2H, m), 1.11(1H, m), 1.69 & 1.81(2H, d), 2.10–2.40(4H, m), 2.79 & 2.81(3H, each s), 3.15–3.80 (4H, m), 3.55(2H, t), 3.82 & 4.58(1H, m), 3.94 & 4.10 (2H, each s), 10.87(1H, brs) |
| 114 | 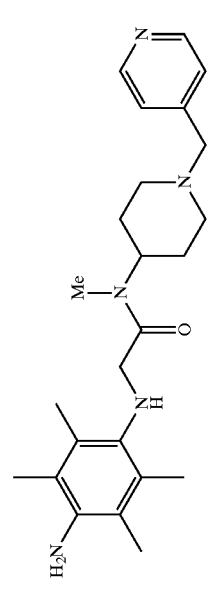 | pale yellow cryst. (HCl salt) >250 (MeOH/EtOH) | 3448, 1638, 1603, 1508, 1373, 1308, 1263, 1193, 1110, 1070, 1008, 949, 798 | 1.67 & 1.80(2H, d), 2.19 & 2.22(12H, s), 2.30–2.50(2H, m), 2.77 & 2.80(3H, each s), 2.90–3.30(2H, m), 3.42(2H, d), 3.82 & 4.59(1H, m), 3.92 & 4.08(2H, each s), 4.47 & 4.50(2H, each s), 11.95(1H, brs) |

-continued

| | Structure | Appearance | IR | NMR |
|---|---|---|---|---|
| 115 | (4-aminomesityl-NH-CH2-C(O)-N(Me)-piperidine-CH2-C6H4-COOH) | pale yellow amorphous (HCl salt) | 1708, 1654, 1418, 1272, 1182, 1108, 1067, 1020, 1005, 944, 871, 755 | 1.67 & 1.78(2H, d), 2.10–2.40(14H, m), 2.77 & 2.80(3H, each s), 2.90–3.10(1H, m), 3.10–3.30(1H, m), 3.30–3.50 (2H, m), 3.77 & 4.57(1H, m), 3.97 & 4.12(2H, each s), 4.30–4.60(2H, m), 7.77(2H, t), 7.90–8.10(2H, m), 11.42 & 11.52(1H, brs) |
| 116 | (4-aminomesityl-NH-CH2-C(O)-N(Me)-piperidine-CH2-C6H4-C(O)NH2) | pale yellow solid (HCl salt) | 3412, 2937, 1652, 1568, 1422, 1394, 1308, 1118, 1104, 943, 869 | free base in CDCl3: 1.50–2.20(6H, m), 2.12(6H, s), 2.27 (6H, s), 2.75 & 2.90(3H, each s), 2.85–2.95(2H, m), 3.32 & 4.54(1H, m), 3.53(2H, d), 3.59(2H, d), 7.40(2H, t), 7.76(2H, d) |
| 117 | (4-aminomesityl-NH-CH2-C(O)-N(Me)-piperidine-CH2CH2-OH) | white amorphous (HCl salt) | 3397, 2951, 2748, 1648, 1584, 1460, 1422, 1310, 1155, 1080, 960 | 1.68 & 1.80(2H, d), 2.00–2.40(12H, m), 2.77 & 2.80 (3H, each s), 3.00–3.50(4H, m), 3.55(2H, t), 3.78(2H, q), 3.83 & 4.59(1H, m), 3.95 & 4.12(2H, each s), 10.47(1H, brs) |
| 118 | (4-aminomesityl-NH-CH2-C(O)-N(Me)-piperidine-CH2CH2-COOH) | pale yellow amorphous (HCl salt) | 1730, 1659, 1643, 1581, 1496, 1424, 1378, 1312, 1221, 1071, 1035, 950, 866, 801 | 1.68 & 1.80(2H, d), 2.00–2.04(14H, m), 2.78 & 2.80 (3H, each s), 2.85(2H, m), 2.98 & 3.17(2H, m), 3.23 (2H, brs), 3.48(2H, brs), 3.83 & 4.58(1H, m), 4.03 & 4.20 (2H, each s), 11.12(1H, brs) |

| No. | Chemical Structure | Properties m.p.(° C.) (solvent) | IR(KBr): cm⁻¹ (HCl salt) | ¹H-NMR(CDCl₃) |
|---|---|---|---|---|
| 119 | 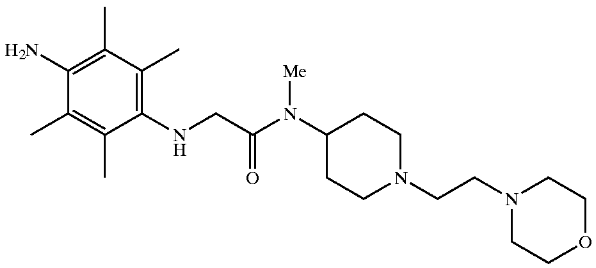 | colorless cryst. (HCl salt) >240 (MeOH/Et₂O) | 1646, 1629, 1496, 1456, 1361, 1308, 1277, 1092, 960, 917 | 1.75 & 1.87(2H, d), 2.10–2.40(14H, m), 2.77 & 2.79 (3H, each s), 3.40–4.10(12H, m), 4.62(1H, m), 11.01 & 11.36(2H, s) |
| 120 | 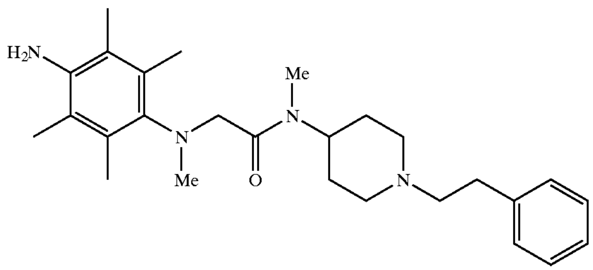 | white amorphous (HCl salt) | 3424, 2940, 1652, 1456, 1366, 1298, 1245, 1160, 1105, 1066 | 1.63–1.73(2H, m), 2.11–2.33(2H, m), 2.21(6H, s), 2.24 (6H, s), 2.70 & 2.72(3H, each s), 2.76 & 2.79(3H, each s), 2.96–3.09(4H, m), 3.23(2H, m), 3.57(2H, m), 3.80(2H, s), 4.55(1H, m), 7.24–7.29(3H, m), 7.33–7.37(2H, m) |
| 121 | 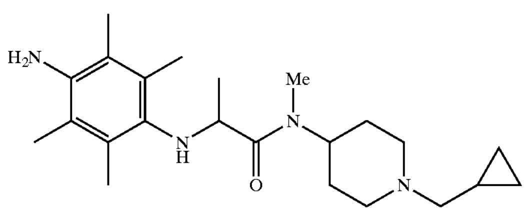 | white amorphous (HCl salt) | 2942, 2710, 1656, 1642, 1462, 1453, 1416, 1311, 1250, 1075, 1033, 948 | free base in CDCl₃: 0.09(2H, m), 0.51(2H, m), 0.85(1H, m), 1.20 & 1.27(3H, each d), 1.42–2.30(8H, m), 2.09(3H, s), 2.10(3H, s), 2.23(3H, s), 2.25(3H, s), 2.69 & 2.77(3H, each s), 2.96 & 3.11(2H, m), 3.19 & 4.48(1H, m), 3.40(2H, brs), 3.94(1H, m) |

-continued

| # | Structure | Form | IR | NMR |
|---|---|---|---|---|
| 122 | (4-aminophenyl with 2,3,5,6-tetramethyl)-NH-CH(Me)-C(=O)-N(Me)-(1-phenethylpiperidin-4-yl) | colorless cryst. (HCl salt) 205–209 (MeOH/Et₂O) | 2937, 2690, 1646, 1493, 1456, 1314, 1247, 1072, 1031, 1015 | 1.21 & 1.28(3H, each d), 1.45–1.98(4H, m), 2.05–2.23 (2H, m), 2.09(3H, s), 2.11(3H, s), 2.23(3H, s), 2.25(3H, s), 2.50–2.65(2H, m), 2.70 & 2.78(3H, each s), 2.72–2.92 (2H, m), 3.05(2H, m), 3.24 & 4.50(1H, m), 3.40(2H, brs), 3.94(1H, m), 7.13–7.36(5H, m) |
| 123 | (4-aminophenyl with 2,3,5,6-tetramethyl)-NH-CH₂-C(=O)-NH-(1-phenethylpiperidin-4-yl) | white amorphous (HCl salt) | 3376, 2936, 2714, 1675, 1560, 1456, 1316, 1282, 1252, 1142, 1115, 1067, 956 | 1.48–1.64(2H, m), 1.97–2.06(2H, m), 2.11(6H, s), 2.19–2.29(2H, m), 2.23(6H, s), 2.57–2.65(2H, m), 2.76–2.90 (2H, m), 2.93(2H, s), 3.45(2H, s), 3.49(2H, brs), 3.92 (1H, m), 7.17–7.33(5H, m) |
| 124 | (4-dimethylaminophenyl with 2,3,5,6-tetramethyl)-NH-CH₂-C(=O)-N(Me)-(1-phenethylpiperidin-4-yl) | white amorphous (HCl salt) | 3443, 2959, 2716, 1652, 1456, 1364, 1313, 1283, 1162, 1018, 758, 705 | 1.60–2.10(4H, m), 2.10–2.30(2H, m), 2.19(6H, s), 2.24(6H, s), 2.50–2.70(2H, m), 2.70–2.80(2H, m), 2.76 & 2.80 & 2.90(9H, each s), 3.06 & 3.09(2H, d), 3.32 & 4.55(1H, m), 3.68 & 3.71(2H, each s) |
| 125 | (3-amino-2,4,6-trimethylphenyl)-NH-CH₂-C(=O)-N(Me)-(1-cinnamylpiperidin-4-yl) | colorless cryst. (HCl salt) 174–176 (MeOH/Et₂O) | 2937, 2717, 1646, 1577, 1489, 1451, 1334, 1306, 1284, 1153, 1109, 1029, 978, 944 | 1.42–2.06(6H, m), 2.12(3H, s), 2.18(3H, s), 2.25(3H, s), 2.77 & 2.90(3H, each s), 2.98–3.62(6H, m), 3.32 & 4.58 (1H, m), 3.69 & 3.72(2H, each s), 6.20–6.38(1H, m), 6.53(1H, m), 6.74 & 6.75(1H, each s), 7.20–7.28(1H, m), 7.32(2H, m), 7.35–7.42(2H, m) |

| | | | |
|---|---|---|---|
| 126 | 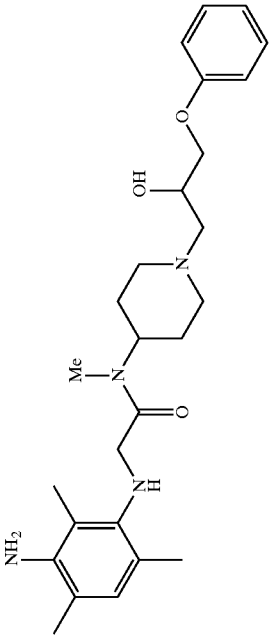 | colorless cryst. (HCl salt) 163–165 (MeOH/Et₂O) | 2946, 2751, 1650, 1599, 1491, 1242, 1154, 1110, 1079, 1042, 947, 762 | 1.47–2.35(6H, m), 2.12(3H, s), 2.19(3H, s), 2.24 & 2.25 (3H, each s), 2.28–2.44(2H, m), 2.77 & 2.90(3H, each s), 2.94–3.20(2H, m), 3.33 & 4.57(1H, m), 3.49(2H, brs), 3.70 & 3.73(2H, each s), 3.98(2H, d), 4.03–4.18(1H, m), 6.74 & 6.76(1H, each s), 6.89–7.00(3H, m), 7.24–7.33 (2H, m) |
| 127 | 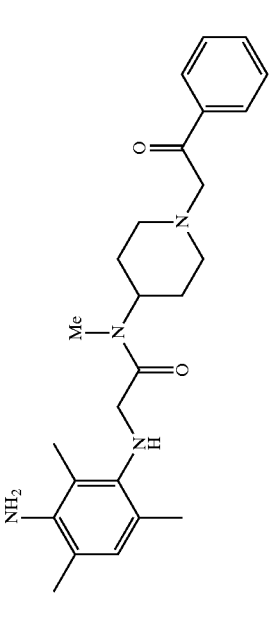 | colorless cryst. (HCl salt) 182–183 (MeOH/Et₂O) | 3425, 2935, 2562, 1693, 1648, 1597, 1488, 1451, 1394, 1306, 1262, 1232, 1107, 1078, 952, 759 | 1.38–2.35(6H, m), 2.12(3H, s), 2.19(3H, s), 2.24 & 2.25 (3H, each s), 2.77 & 2.90(3H, each s), 3.03–3.15(2H, m), 3.34 & 4.57(1H, m), 3.38–3.62(2H, brs), 3.70 & 3.73(2H, each s), 3.84 & 3.85(2H, each s), 6.74 & 6.76(1H, each s), 7.47(2H, m), 7.58(1H, m), 7.98(2H, m) |
| 128 | 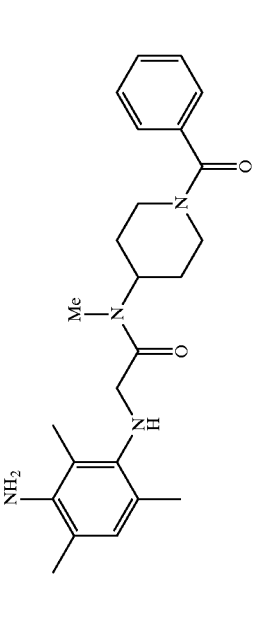 | colorless cryst. (HCl salt) 166–168 (MeOH/Et₂O) | 2936, 2573, 1646, 1618, 1575, 1469, 1448, 1324, 1279, 1130, 1022, 788 | 1.45–1.83(4H, m), 2.12(3H, s), 2.17 & 2.18(3H, each s), 2.23 & 2.25(3H, each s), 2.76 & 2.89(3H, each s), 3.14 (1H, m), 3.49(2H, brs), 3.56 & 4.78(1H, m), 3.71 & 3.75 (2H, each s), 3.89(1H, m), 4.49(1H, m), 4.85(1H, m), 6.74(1H, s), 7.41(5H, m) |
| 129 | 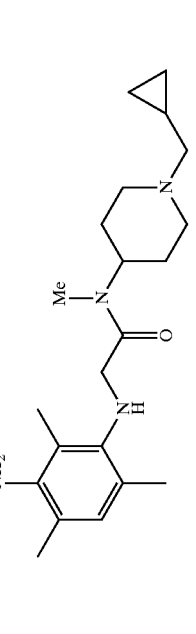 | colorless cryst. (HCl salt) 173–175 (MeOH/Et₂O) | 3424, 2593, 1638, 1573, 1490, 1404, 1360, 1312, 1281, 1201, 1107, 1031, 948 | 0.02–0.17(2H, m), 0.45–0.56(2H, m), 0.85(1H, m), 1.46–1.82 (4H, m), 1.84–2.31(4H, m), 2.12(3H, s), 2.19(3H, s), 2.25 & 2.26(3H, each s), 2.76 & 2.90(3H, each s), 3.07–3.21 (2H, each s), 3.29 & 4.51(1H, m), 3.49(2H, brs), 3.69 & 3.72 (2H, each s), 4.37–4.61(1H, m), 6.74 & 6.75(1H, each s) |

| | | | | |
|---|---|---|---|---|
| 130 | [structure: NH2-trimethylphenyl-NH-CH2-C(O)-N(Me)-piperidine-N-SO2-phenyl] | white amorphous (HCl salt) | 2933, 2852, 1656, 1648, 1584, 1486, 1447, 1333, 1307, 1167, 1094, 1024, 936, 740 | 1.46–1.70(2H, m), 1.72–1.85(2H, m), 2.11(3H, s), 2.15(3H, s), 2.21(3H, s), 2.72 & 2.84(3H, each s), 3.38–3.54(2.5H, m), 3.59 & 3.67(2H, each s), 3.91(2H, m), 4.42(1.5H, m), 6.71 & 6.72(1H, each s), 7.55(2H, t), 7.63(1H, t), 7.70(2H, d) |
| 131 | [structure: NH2-trimethylphenyl-NH-CH2-C(O)-N(Me)-piperidine-N-benzyl] | colorless cryst. (HCl salt) 176–178 (MeOH/Et₂O) | 2937, 2727, 1648, 1489, 1455, 1420, 1309, 1105, 1031, 946 | 1.48–2.28(6H, m), 2.11(3H, s), 2.18(3H, s), 2.23 & 2.24 (3H, each s), 2.75 & 2.89(3H, each s), 2.94(2H, m), 3.29 & 4.38–4.60(2H, m), 3.50(4H, m), 3.68 & 3.71(2H, each s), 6.73 & 6.75(1H, each s), 7.20–7.35(5H, m) |
| 132 | [structure: NH2-trimethylphenyl-NH-CH2-C(O)-N(Me)-piperidine-N-butyl] | colorless cryst. (HCl salt) 172–174 (MeOH/Et₂O) | 3444, 2938, 2878, 1638, 1572, 1484, 1424, 1406, 1361, 1317, 1202, 1094, 1015, 946 | 0.91(3H, t), 1.23–1.38(2H, m), 1.40–1.51(2H, m), 1.64–1.95 (2H, m), 1.98–2.38(4H, m), 2.12(3H, s), 2.18(3H, s), 2.24 & 2.25(3H, each s), 2.75 & 2.86(3H, each s), 2.93–3.06(2H, m), 3.28 & 4.39–4.59(2H, m), 3.49(2H, m), 3.69 & 3.72(2H, each s), 6.74 & 6.75(1H, each s) |
| 133 | [structure: NH2-trimethylphenyl-NH-CH2-C(O)-N(Me)-piperidine-N-CH2-naphthyl] | pale yellow cryst. (HCl salt) 186–189 (MeOH/Et₂O) | 2936, 2726, 1646, 1571, 1486, 1420, 1337, 1306, 1106, 1030, 942, 826 | 1.47–1.63(2H, m), 1.67–1.81(2H, m), 1.82–2.07(2H, m), 2.11(3H, s), 2.18(3H, s), 2.23 & 2.24(3H, each s), 2.76 & 2.90(3H, each s), 2.99(2H, m), 3.31 & 4.36–4.62(2H, m), 3.47(2H, brs), 3.65(2H, s), 3.68 & 3.71(2H, each s), 6.73 & 6.74(1H, each s), 7.42–7.52(3H, m), 7.73–7.80 (1H, m), 7.81(3H, m) |

| | | | |
|---|---|---|---|
| 134 | 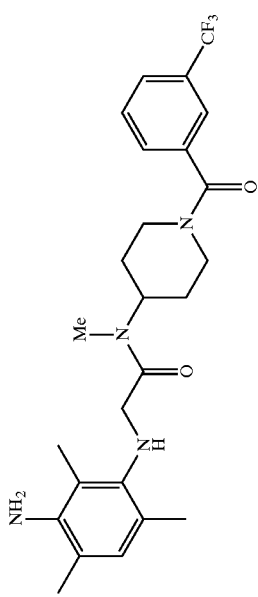 | colorless cryst. (HCl salt) 160–163 (MeOH/Et₂O) | 2942, 2818, 1634, 1488, 1430, 1332, 1273, 1252, 1168, 1128, 1073, 1023, 816 | 1.45–1.88(4H, m), 2.12(3H, s), 2.17 & 2.18(3H, each s), 2.25(3H, s), 2.77 & 2.89(3H, each s), 3.17 & 4.47(1H, m), 3.38–3.85(4H, m), 3.71 & 3.75(2H, each s), 4.79(2H, m), 6.72 & 6.74(1H, each s), 7.59(2H, m), 7.69(2H, m) |
| 135 | 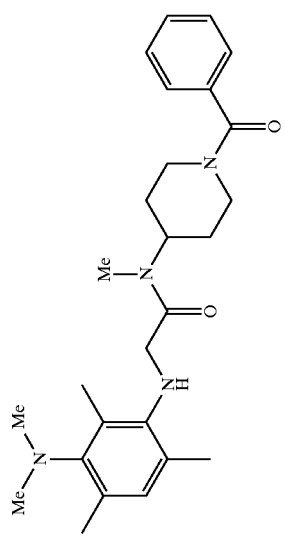 | pale yellow cryst. (HCl salt) 156–158 (MeOH/Et₂O) | 3440, 2954, 1618, 1576, 1448, 1371, 1323, 1280, 1129, 1115, 1021, 790 | 1.44–1.84(4H, m), 2.21(3H, s), 2.26(3H, s), 2.27(3H, s), 2.72–2.93(2H, m), 2.78 & 2.79(3H, each s), 2.81(6H, s), 3.13 & 4.57(1H, m), 3.40–3.64(2H, brs), 3.68–3.93(2H, m), 4.78(2H, m), 6.78(1H, s), 7.41(5H, brs) |
| 136 | 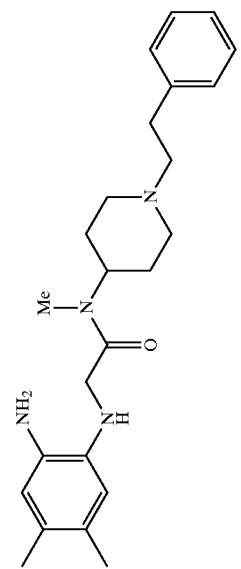 | pale brown amorphous | 3426, 2940, 1654, 1514, 1454, 1415, 1390, 1310, 1246, 1221, 1101 | HCl salt in DMSO-d₆: 1.71 & 1.90(2H, m), 2.09 & 2.11(3H, each s), 2.18(3H, s), 2.28(2H, m), 2.79 & 2.93(3H, each s), 3.07–3.17(4H, m), 3.26(2H, m), 3.57–3.63(2H, m), 3.97 & 4.08(2H, each s), 4.60(1H, m), 6.65 & 8.69(1H, each s), 7.03(1H, s), 7.27–7.35(5H, m) |

| No. | Chemical Structure | Properties m.p.(° C.) (solvent) | IR(KBr): cm⁻¹ (HCl salt) | ¹H-NMR(DMSO-D₆): HCl salt |
|---|---|---|---|---|
| 137 | (structure: 2-amino-4,5-dimethylphenyl-NH-C(O)-CH₂-N(Me)-piperidine-N-CH₂-(phenylcyclopropyl)) | pale brown amorphous | 3426, 2940, 1639, 1514, 1498, 1461, 1414, 1303, 1248, 1095, 1030 | HCl salt in DMSO-d₆; 1.09–1.17(2H, m), 1.45(1H, m), 1.69 & 1.89(2H, m), 2.11(3H, s), 2.17 & 2.18(3H, each s), 2.24–2.40(3H, m), 2.78 & 2.92(3H, each s), 3.05–3.17 (4H, m), 3.54(2H, m), 3.96 & 4.07(2H, each s), 4.58(1H, m), 6.65 & 6.68(1H, each s), 7.01(1H, s), 7.17(3H, m), 7.28(2H, m) |
| 138 | (structure: 4-amino-2,5-dichlorophenyl-NH-CH₂-C(O)-N(Me)-piperidine-N-CH₂CH₂-phenyl) | pale yellow cryst. (HCl salt) 206–210 (MeOH/Et₂O) | 3378, 2936, 2630, 1641, 1518, 1413, 1308, 1202, 1098, 1074, 755 | 1.67–1.97(2H, m), 2.20(2H, m), 2.78 & 2.90(3H, each s), 3.08(4H, m), 3.28(2H, m), 3.40–3.57 & 4.56(1H, m), 3.65(2H, m), 3.95 & 4.05(2H, each s), 6.79 & 6.84(1H, each s), 7.14 & 7.15(1H, each s), 7.21–7.41(5H, m), 10.43(1H, brs) |
| 139 | (structure: 4-amino-2,6-dichlorophenyl-NH-CH₂-C(O)-N(Me)-piperidine-N-CH₂-C(O)-NH-phenyl) | pale brown powder 178–181 (MeOH/ iso-Pr₂O) | 3444, 2942, 2596, 1692, 1637, 1556, 1488, 1448, 1405, 1346, 1302, 1153 | 1.72 & 1.86(2H, m), 2.18(2H, m), 2.78 & 2.80(3H, each s), 3.29(2H, m), 3.59(2H, m), 4.09 & 4.16(4H, each s), 4.58 (1H, m), 7.08–7.15(3H, m), 7.36(2H, t), 7.62(2H, m) |

The effects, such as cytoprotective effect against glutamate induced cell death using neuron of cerebral cortex, calbindin D28Kd inducing effect by the western blot technique, and cerebral edema suppressing effect of aminophenoxyacetic acid derivatives, of the formula (I) have been evaluated by following biological testing methods.

Biological Test 1: Cytoprotective Effet Agaist Glutamate Induced Cell Death

In accordance with the method of M. P. Mattoson [M. P. Mattoson, *Brain Res. Rev.*, 13, 179 (1988)], brain of 18-days fetus rats of Wister strain were taken out. Then, cells of cerebral cortex ($4 \times 10^5$ cells/ml) were seeded on poly-L-lysine coated 96 wells flat bottom plate (Sumitomo Bakelite Co., Ltd.) in concentration of $4 \times 10^4$ cells/each well. After 48 hours of incubation, 1 μM of test compounds were added, then after further 24 hours, 1 mM of glutamate were further added for inducing the cell injury. 12 hours after adding glutamate, MTT [3-(4,5-dimethylthiazol)-2,5-diphenyltetrazolium bromide] was added and incubated for 6 hours.

After incubation, 200 μl of dimethy sulfoxide was added to each wells, and the amounts of reduced MTT were colorimetrically analyzed by Micro ELISA Reader using 570 nm of main-wavelength and 650 nm of sub-wavelength.

The effect of the test compounds was determined as the survival rate of living cells (%) according to the following equation:

Survival rate of living cells (%)=[(test compound group−glutamate treated group)÷(control group−glutamate treated group)]×100

That is, the survival rate of living cells after incubation of the control group was converted to 100%, and the survival rata of living cells of the tested compounds was shown in Table II.

TABLE II

| Compound No. | Survival Rate (%) (Compound: 1 μM) |
|---|---|
| 38 | 114 |
| 40 | 108 |
| 41 | 86 |
| 42 | 131 |
| 44 | 93 |
| 45 | 190 |
| 46 | 101 |
| 48 | 207 |
| 49 | 193 |
| 50 | 54 |
| 53 | 144 |
| 60 | 60 |
| 61 | 58 |
| 62 | 63 |
| 65 | 73 |
| 66 | 60 |
| 67 | 69 |
| 68 | 75 |
| 69 | 68 |
| 70 | 88 |
| 71 | 89 |
| 74 | 87 |
| 75 | 96 |
| 76 | 106 |
| 77 | 111 |
| 78 | 96 |
| 79 | 79 |
| 80 | 99 |
| 81 | 97 |
| 82 | 149 |
| 83 | 65 |
| 84 | 87 |

TABLE II-continued

| Compound No. | Survival Rate (%) (Compound: 1 μM) |
|---|---|
| 85 | 98 |
| 86 | 127 |
| 87 | 81 |
| 88 | 81 |
| 89 | 126 |
| 90 | 149 |
| 91 | 203 |
| 92 | 66 |
| 93 | 171 |
| 94 | 198 |
| 95 | 61 |
| 96 | 91 |
| 97 | 119 |
| 98 | 120 |
| 99 | 151 |
| 100 | 138 |
| 101 | 138 |
| 102 | 89 |
| 103 | 180 |
| 104 | 117 |
| 105 | 86 |
| 106 | 151 |
| 107 | 227 |
| 109 | 76 |
| 110 | 61 |
| 111 | 84 |
| 112 | 76 |
| 113 | 74 |
| 114 | 50 |
| 116 | 59 |
| 119 | 115 |
| 120 | 88 |
| 121 | 82 |
| 124 | 86 |
| 125 | 52 |
| 126 | 47 |
| 127 | 72 |
| 128 | 81 |
| 129 | 64 |
| 130 | 60 |
| 131 | 65 |
| 132 | 60 |
| 133 | 101 |
| 134 | 79 |
| 135 | 76 |
| 136 | 81 |
| 137 | 71 |
| 138 | 42 |
| 139 | 53 |

Biological Test 2: Calbindin D28Kd Inducing Effect

In accordance with the method of M. P. Mattoson [M. P. Mattoson, *Brain Res. Rev.*, 13, 179 (1988)], brain of 18-days fetus rats of Wister strain were taken out. Then, cells of cerebral cortex (5,500 cells/mm$^2$) were seeded on poly-L-lysine coated 6 wells plate (Falcon) (3.5 mm, Sumilon) and incubated for 7 days.

Test compounds were added on culture day 5, and after 7 days of incubation, the protein was extracted with homogenized buffer solution [containing 20 mM of Tris-HCl (pH=7.4), 1 mM of EDTA, and 0.1 mM of phenylmethylsulfonyl fluoride].

The effect of the test compounds was determined by the western blot technique using polyclonal anti calbindine D28K (Swant Co., Ltd.) as antibody.

Table III shows the test results. In the table, the amount of induced calbindine D28Kd of the control group (none-treated group) was indicated as 100 percents.

TABLE III

| Compound No. | Amount of induced Calbindine D28Kd (% vs. control) (Compound: 1 μM) |
|---|---|
| 29 | 122 |
| 40 | 150 |
| 111 | 167 |
| 128 | 171 |
| Control | 100 |

Biological Test 3: Cerebral Edema Suppressing Effect 8-week-old rats of slc: Wister strain were used. Rats were anesthetized by intraperitoneal administration of 50 mg/kg of Nembutal (Trade Name), and then, fixed on brain fixactor. The sterile metal screw (3.75 mm in length/1.0 mm in diameter/0.75 mm in length of screw thread) was plugged in the 1.5 mm right and 0.8 mm rear side of the bregma to press frontparietal cortex organ to cause brain injury.

6 days after the operation, the whole brain was taken out and right cerebral hemisphere (injured side) was isolated. After measurement of the wet weight of the cerebral hemisphere, it was dried at 110° C. for 24 hours on aluminum foil. The dry weight of the cerebral hemisphere was measured, and the water content was calculated by using the following formula:

Water content (%)=[(wet weight of hemisphere−dry weight of hemisphere)/wet weight of hemisphere] ×100

The test compounds were intravenously administered just after the operation via tail vein of the rats.

Table IV shows the test results.

TABLE IV

| Compound No. (administration amount) | Cerebral edema suppressing rate (%) |
|---|---|
| 29 (3 mg/kg) | 30.9 |
| 40 (1 mg/kg) | 31.1 |
| 40 (3 mg/kg) | 20.5 |
| 42 (1 mg/kg) | 24.5 |
| 42 (3 mg/kg) | 31.0 |
| 104 (3 mg/kg) | 18.9 |
| 105 (3 mg/kg) | 23.2 |
| 108 (3 mg/kg) | 20.3 |
| 109 (3 mg/kg) | 24.7 |
| 111 (3 mg/kg) | 25.0 |
| 112 (3 mg/kg) | 20.7 |
| 113 (3 mg/kg) | 20.0 |
| 119 (1 mg/kg) | 21.6 |
| 128 (3 mg/kg) | 20.3 |
| 132 (1 mg/kg) | 30.4 |
| 134 (1 mg/kg) | 27.9 |
| 134 (3 mg/kg) | 35.0 |

INDUSTRIAL APPLICABILITY

As described above, the present invention provides lower molecular weight compounds, especially aminophenoxyacetic acid derivatives of the formula (I), which is capable of inducing the calbindin D28Kd, one of $Ca^{2+}$-binding proteins, and can be easily administrated. Since the induction of calbindin D28Kd caused by the administration of the compound provided by the present invention cause neuroprotective effect and cerebral functional and organic disorder improving and treating effect, it can be understood that the agent of the present invention is highly applicable in pharmaceutical field.

What is claimed is:

1. A compound which is 4-({4-[[(4-Amino-2,3,5,6-tetramethylanilino)acetyl]-(methyl)amino]-1-piperidino}methyl)benzamide or a pharmaceutically acceptable salt thereof.

2. A compound which is 2-(4-Amino-2,3,5,6-tetramethylanilino)-N-[1-(cyclo-propylmethyl)-4-piperidinyl]-N-methylpropamide or a pharmaceutically acceptable salt thereof.

3. A compound which is 2-(4-Amino-2,3,5,6-tetramethylanilino)-N-methyl-[1-(2-phenyl-2-oxyethyl)-4-piperidinyl]acetamide or a pharmaceutically acceptable salt thereof.

4. A compound which is 2-(4-Amino-2,3,5,6-tetramethylanilino)-N-[l-[1-(2-hydroxy-2-phenylethyl)-4-piperidinyl]-N-methylacetamide or a pharmaceutically acceptable salt thereof.

5. A compound which is 2-(4-Amino-2,5-dichloroanilino)-N-[1-(2-phenethyl)-4-piperidinyl]acetamide or a pharmaceutically acceptable salt thereof.

6. A compound which is 2-(3-Amino-2,4,6-trimethylanilino)-N-(1-benzoyl-4-piperidinyl)-N-methylacetamide or a pharmaceutically acceptable salt thereof.

* * * * *